(12) United States Patent
Metz et al.

(10) Patent No.: US 7,700,320 B2
(45) Date of Patent: Apr. 20, 2010

(54) SCHIZOCHYTRIUM FATTY ACID SYNTHASE (FAS) AND PRODUCTS AND METHODS RELATED THERETO

(75) Inventors: James G. Metz, Longmont, CO (US);
Craig A. Weaver, Boulder, CO (US);
Jerry Kuner, Longmont, CO (US)

(73) Assignee: Martek Biosciences Corporation, Columbia, MD (US)

( * ) Notice: Subject to any disclaimer, the term of this patent is extended or adjusted under 35 U.S.C. 154(b) by 875 days.

(21) Appl. No.: 11/058,046

(22) Filed: Feb. 14, 2005

(65) Prior Publication Data

US 2005/0191679 A1 Sep. 1, 2005

Related U.S. Application Data

(60) Provisional application No. 60/544,692, filed on Feb. 13, 2004.

(51) Int. Cl.
*C12Q 1/68* (2006.01)
*C07H 2/04* (2006.01)
*C12P 7/64* (2006.01)
*C12N 9/80* (2006.01)

(52) U.S. Cl. .................. 435/69.1; 435/193; 435/183; 435/134; 435/320; 435/258.1; 536/23.226

(58) Field of Classification Search .................. None
See application file for complete search history.

(56) References Cited

FOREIGN PATENT DOCUMENTS

| WO | WO 97/13845 | 4/1997 |
|---|---|---|
| WO | WO 00/61729 | 10/2000 |
| WO | WO 03/072602 | 9/2003 |

OTHER PUBLICATIONS

International Search Report and Written Opinion for International Application No. PCT/US05/046111, dated Feb. 27, 2007.
Hauvermale A., et al. The characterization of Fatty Acids Synthesis in Schizochytrium sp. American Society of Plant Biologists Meeting. Jul. 26, 2004, Abtract #307. http://abstracts.aspb.org/pb2004/public/p45/7521.html.
Metz G.J. Production of Polyunsaturated Fatty Acids by Polyketide Synthethases in Both Prokaryotes and Eukaryotes. Science. Jul. 13, 2001., vol. 293, pp. 290-293.
SIGMA Chemical Company. Bioactive Peptides, 1993, pp. 1067 and 1089.
International Preliminary Report on Patentability for International (PCT) Patent Application No. PCT/US2005/004611, mailed Mar. 22, 2007, 7 pages.
Kajiwara et al. "Cloning of a fatty acid synthase component FAS1 gene from *Saccharomyces kluyveri* and its functional complementation of *S. cerevisiae* fas1 mutant", Yeast 2001; 18: 1339-1345.
GenPept Accession AAB41493, fatty acid syntase, alpha subunit [*Emericella nidulans*], Jan. 28, 1997, 3 pages.
TrEMBL Accession P78615_EMENI, May 1, 1997, 3 pages.
GenPept Accession AAA34345, "fatty acid synthase alpha subunit", Feb. 24, 1994, 3 pages.
GenPept Accession JC4086 gi|1076938|pir||JC4086, May 5, 2000, 3 pages.
GenPept Accession S01787 "gi|83735|pir||S01787", May 5, 2000, 2 pages.

*Primary Examiner*—Andrew Wang
*Assistant Examiner*—Kagnew H Gebreyesus
(74) *Attorney, Agent, or Firm*—Sheridan Ross P.C.

(57) ABSTRACT

Disclosed are a fatty acid synthase (FAS) from *Schizochytrium*, biologically active fragments and homologues thereof, a nucleic acid sequence encoding such FAS, fragments and homologues thereof, the gene encoding *Schizochytrium* FAS, host cells and organisms that recombinantly express the FAS, host cells and organisms in which the expression and/or activity of the endogenous FAS has been attenuated, and various methods for making and using any of these proteins, nucleic acid molecules, genes, host cells or organisms.

10 Claims, 4 Drawing Sheets

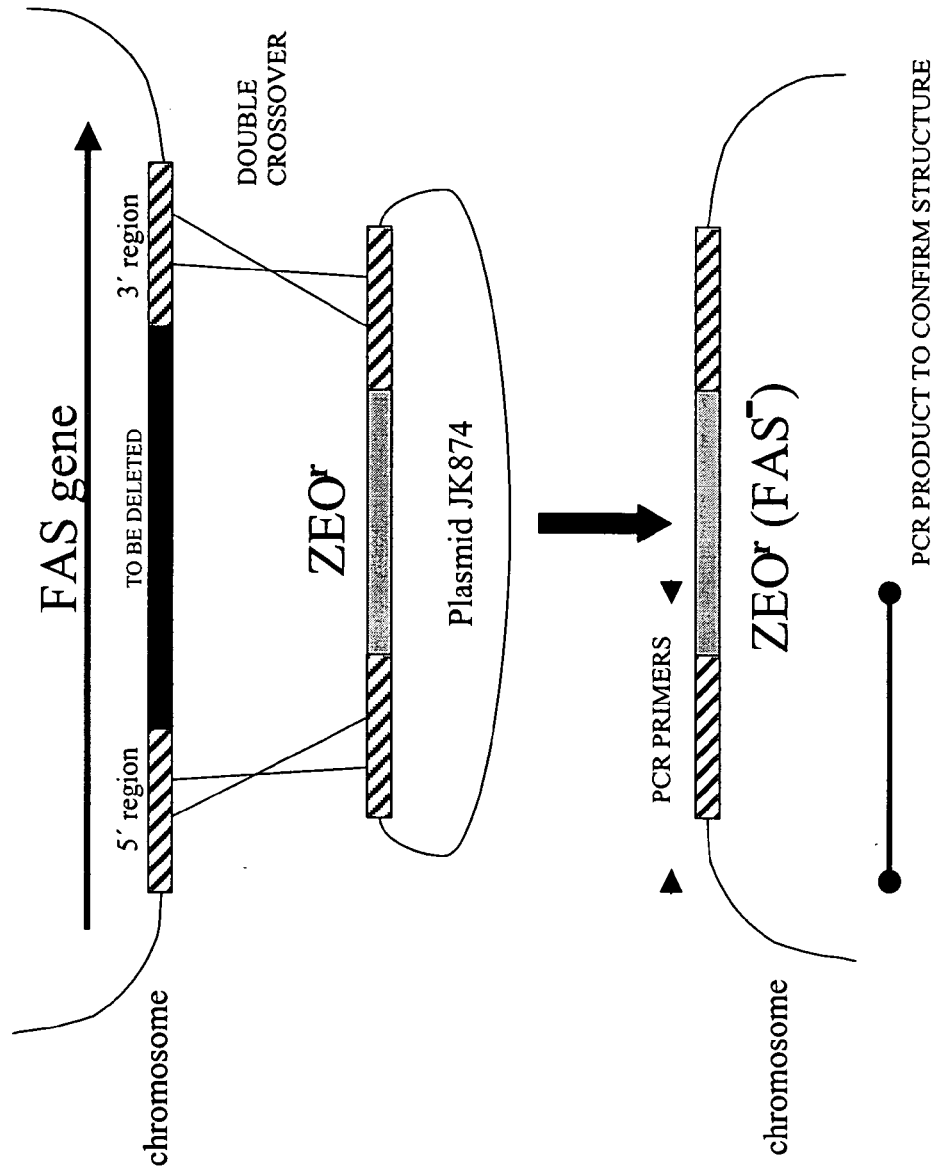

In vitro Fatty Acid Synthesis Assays

SEQUENCE LISTING

```
<160> NUMBER OF SEQ ID NOS: 13

<210> SEQ ID NO 1
<211> LENGTH: 12411
<212> TYPE: DNA
<213> ORGANISM: Schizochytrium sp.
<220> FEATURE:
<221> NAME/KEY: CDS
<222> LOCATION: (1)..(12411)

<400> SEQUENCE: 1 atg gcg cag ccc gag tcg acg acg ccg acc atg acg ccc gag gaa ggc     48
Met Ala Gln Pro Glu Ser Thr Thr Pro Thr Met Thr Pro Glu Glu Gly
1               5                   10                  15 cag atg gag ggg gcg ccg cag cag gat aat gcc cag gtg aag aag cac     96
Gln Met Glu Gly Ala Pro Gln Gln Asp Asn Ala Gln Val Lys Lys His
            20                  25                  30 tgc ttc gcc gac gcc gat gtg gca acc tgc atc gcc gcc ttt ggc ggt    144
Cys Phe Ala Asp Ala Asp Val Ala Thr Cys Ile Ala Ala Phe Gly Gly
        35                  40                  45 cag gga agc gac tgg ctc agt gag ctg cgc tcc ctc cag gaa aag ggc    192
Gln Gly Ser Asp Trp Leu Ser Glu Leu Arg Ser Leu Gln Glu Lys Gly
    50                  55                  60 cag acc aac gtg cga gaa acc atc gaa ctc gca ctc gac aaa ctc gag    240
Gln Thr Asn Val Arg Glu Thr Ile Glu Leu Ala Leu Asp Lys Leu Glu
65                  70                  75                  80 gat ctt gtc aag gcc gag ccc tgg tac gag gag cac gga gga tgc gat    288
Asp Leu Val Lys Ala Glu Pro Trp Tyr Glu Glu His Gly Gly Cys Asp
                85                  90                  95 atc cgc gcc tgg ctc gag agc gac gac aat gtc ccc aac ttc gac ctc    336
Ile Arg Ala Trp Leu Glu Ser Asp Asp Asn Val Pro Asn Phe Asp Leu
            100                 105                 110 ctc cgc tac gcg ccc gtc tcc ttc ccc ctc atc ttc ctc acc caa atg    384
Leu Arg Tyr Ala Pro Val Ser Phe Pro Leu Ile Phe Leu Thr Gln Met
        115                 120                 125
```

-continued

| | |
|---|---|
| tgc aat tac atg cgt gtc ctc gag aaa ctc ggc acc tgc cat gaa gac<br>Cys Asn Tyr Met Arg Val Leu Glu Lys Leu Gly Thr Cys His Glu Asp<br>130                      135                      140 | 432 |
| gcc ctc caa aag ggc tgg gtc aag gcc tcg ctc gga cac agc cag ggc<br>Ala Leu Gln Lys Gly Trp Val Lys Ala Ser Leu Gly His Ser Gln Gly<br>145                      150                      155                      160 | 480 |
| gtc gtc tcc gcc gcc gtc gtt gcc gca gcc aac acc gac cgc gag ctg<br>Val Val Ser Ala Ala Val Val Ala Ala Ala Asn Thr Asp Arg Glu Leu<br>                      165                      170                      175 | 528 |
| cgc aac ctc gtg gtc tcc ggc ctc gaa tac atg tca aaa gtc ggc atc<br>Arg Asn Leu Val Val Ser Gly Leu Glu Tyr Met Ser Lys Val Gly Ile<br>                  180                      185                      190 | 576 |
| gcc gcc cag cgc acg ctc gac tac gag ctc gga cgc gcc aac gcc ggc<br>Ala Ala Gln Arg Thr Leu Asp Tyr Glu Leu Gly Arg Arg Asn Ala Gly<br>195                      200                      205 | 624 |
| ccg gag acc ccg atg ctc gct gta cag gga atg gac gaa aaa gtc ctt<br>Pro Glu Thr Pro Met Leu Ala Val Gln Gly Met Asp Glu Lys Val Leu<br>210                      215                      220 | 672 |
| acc aag gcc ttc aag gcc gcc gtc tcg ctc tcc aac gag aag cag gcc<br>Thr Lys Ala Phe Lys Ala Ala Val Ser Leu Ser Asn Glu Lys Gln Ala<br>225                      230                      235                      240 | 720 |
| atg atg gcc aaa atc tcc ccc acg gcc gcc gcc gcc acc gcc gcc ccg<br>Met Met Ala Lys Ile Ser Pro Thr Ala Ala Ala Ala Thr Ala Ala Pro<br>                      245                      250                      255 | 768 |
| gcc gcc gtt agc gac gaa gat cgc ttc tcc atc gcc ctc cgc aac ggc<br>Ala Ala Val Ser Asp Glu Asp Arg Phe Ser Ile Ala Leu Arg Asn Gly<br>                      260                      265                      270 | 816 |
| cac gac gac ttt gtc gtc tgc ggc gag ccc aag gac ctg cgc gtc ctc<br>His Asp Asp Phe Val Val Cys Gly Glu Pro Lys Asp Leu Arg Val Leu<br>                  275                      280                      285 | 864 |
| cgc aag gtc atc gag aaa cag agc gcc gag ccc ggc aag gag gca cag<br>Arg Lys Val Ile Glu Lys Gln Ser Ala Glu Pro Gly Lys Glu Ala Gln<br>290                      295                      300 | 912 |
| gcg cgc acg ccc ttt tcc aag cgc aag ccc gtc acc cag acc acc ttc<br>Ala Arg Thr Pro Phe Ser Lys Arg Lys Pro Val Thr Gln Thr Thr Phe<br>305                      310                      315                      320 | 960 |
| ctc cgc atg acg gcc gtc ttc cac agc gct ctc aac aag gac gcc ctc<br>Leu Arg Met Thr Ala Val Phe His Ser Ala Leu Asn Lys Asp Ala Leu<br>                      325                      330                      335 | 1008 |
| gcc cag atc aac aca tgg gcc ccg gag tcc gcc ttt agc aag gcc ttc<br>Ala Gln Ile Asn Thr Trp Ala Pro Glu Ser Ala Phe Ser Lys Ala Phe<br>                      340                      345                      350 | 1056 |
| gcc cag gcc tcg ctc cgt gtt ccc gtc ttt gac acc aag tct ggc gct<br>Ala Gln Ala Ser Leu Arg Val Pro Val Phe Asp Thr Lys Ser Gly Ala<br>                  355                      360                      365 | 1104 |
| aat ctg caa gat gtt ccc gcc gcc gat gtt gtc gcc cat ctt acc acc<br>Asn Leu Gln Asp Val Pro Ala Ala Asp Val Val Ala His Leu Thr Thr<br>370                      375                      380 | 1152 |
| aac atg ctc act gag cgc gcc gac gtt ctc gtc tcc ctc cgt gcc gcc<br>Asn Met Leu Thr Glu Arg Ala Asp Val Leu Val Ser Leu Arg Ala Ala<br>385                      390                      395                      400 | 1200 |
| gag acc aag acc gac gcc agc cac ctc ctc tgt ttc ggc cct ggc cgc<br>Glu Thr Lys Thr Asp Ala Ser His Leu Leu Cys Phe Gly Pro Gly Arg<br>                      405                      410                      415 | 1248 |
| gtc gcc ggc cac ctc atg gcc cac gcc ctc gtg ggc acg ggg atc cag<br>Val Ala Gly His Leu Met Ala His Ala Leu Val Gly Thr Gly Ile Gln<br>                      420                      425                      430 | 1296 |
| gtc gtc cag gcc gcc gac ccg gac acc ccc aac gac tcc aag cga tcc<br>Val Val Gln Ala Ala Asp Pro Asp Thr Pro Asn Asp Ser Lys Arg Ser<br>435                      440                      445 | 1344 |

-continued

| | | |
|---|---|---|
| tcg gcc gtc tcc att ggc tcc gtc atc gag gcc cag tcc ccc gag gcc<br>Ser Ala Val Ser Ile Gly Ser Val Ile Glu Ala Gln Ser Pro Glu Ala<br>450                             455                       460 | 1392 |
| gtg ccc acg gcg ccc gag tgg gcc aag aag ttc gcc ccg cgc att gcc<br>Val Pro Thr Ala Pro Glu Trp Ala Lys Lys Phe Ala Pro Arg Ile Ala<br>465                           470                       475                  480 | 1440 |
| gtg cgc gcc ggt gac ggc gag cgc gtg ctc atg acc aag ttc acc tcg<br>Val Arg Ala Gly Asp Gly Glu Arg Val Leu Met Thr Lys Phe Thr Ser<br>                       485                     490                    495 | 1488 |
| acc ctt ggc cgc gcc ccg gtc ctc atg tcc ggc atg acg ccc acg acc<br>Thr Leu Gly Arg Ala Pro Val Leu Met Ser Gly Met Thr Pro Thr Thr<br>            500                     505                      510 | 1536 |
| tcg ttc cac ggc gtc gat ctc gtg gcc gcc gcc tcc aac gcc ggc ttc<br>Ser Phe His Gly Val Asp Leu Val Ala Ala Ala Ser Asn Ala Gly Phe<br>                 515                     520                    525 | 1584 |
| aac gcc gag cta gct gcc ggt ggt ctc ccc acg ccc gac atc ttc aag<br>Asn Ala Glu Leu Ala Ala Gly Gly Leu Pro Thr Pro Asp Ile Phe Lys<br>530                           535                     540 | 1632 |
| tcc aag gtc ctc gag ctc gcc agc aag ctc aac ccg ggc gtc ggc atc<br>Ser Lys Val Leu Glu Leu Ala Ser Lys Leu Asn Pro Gly Val Gly Ile<br>545                           550                     555                  560 | 1680 |
| tcc atc aac atg ctc tac ctg aac gcc tac cag tgg ggg ttc cag ttt<br>Ser Ile Asn Met Leu Tyr Leu Asn Ala Tyr Gln Trp Gly Phe Gln Phe<br>                 565                     570                    575 | 1728 |
| ccg ctc gtg gtt gag ctc gcc aag cag ggc gtc ccc atc gag tcc atc<br>Pro Leu Val Val Glu Leu Ala Lys Gln Gly Val Pro Ile Glu Ser Ile<br>            580                     585                    590 | 1776 |
| acc att ggc gct ggt gtt ccc tcc gag gac aag gcc ggc gac atc ttt<br>Thr Ile Gly Ala Gly Val Pro Ser Glu Asp Lys Ala Gly Asp Ile Phe<br>               595                     600                    605 | 1824 |
| gac ggc ctc cag agc gcc ggc atc aac ctc atc gcc ttc aag ccg ggt<br>Asp Gly Leu Gln Ser Ala Gly Ile Asn Leu Ile Ala Phe Lys Pro Gly<br>610                           615                     620 | 1872 |
| tcc aag cag gcc atc aag gac gtc tgt gcc ctt gcc gcc ctg cgt ccc<br>Ser Lys Gln Ala Ile Lys Asp Val Cys Ala Leu Ala Ala Leu Arg Pro<br>625                           630                     635                  640 | 1920 |
| agc atg aac gtc atg ctc cag tgg acc tcg ggc cgc ggc ggt ggc cac<br>Ser Met Asn Val Met Leu Gln Trp Thr Ser Gly Arg Gly Gly His<br>                 645                     650                    655 | 1968 |
| cac tcg ttt gag gac ttc cac gag ccc ctc ctc tcg acc tac gag gag<br>His Ser Phe Glu Asp Phe His Glu Pro Leu Leu Ser Thr Tyr Glu Glu<br>            660                     665                    670 | 2016 |
| atc cgc agc cac gac aac att gtc ctt gtc att ggc tcc ggc ttt ggt<br>Ile Arg Ser His Asp Asn Ile Val Leu Val Ile Gly Ser Gly Phe Gly<br>               675                     680                    685 | 2064 |
| gat gcc cag agc gtg ctc acc tac ctc gat ggc tca tgg tcc cag aac<br>Asp Ala Gln Ser Val Leu Thr Tyr Leu Asp Gly Ser Trp Ser Gln Asn<br>690                           695                     700 | 2112 |
| gag atc ttt ggc cgt ctg gcc aag atg ccc gtc gat ggt gtc ctc ttt<br>Glu Ile Phe Gly Arg Leu Ala Lys Met Pro Val Asp Gly Val Leu Phe<br>705                           710                     715                  720 | 2160 |
| ggc tcg cgc tgc atg gtc gcc tta gaa gcc gcc acc gca ccg gag gtc<br>Gly Ser Arg Cys Met Val Ala Leu Glu Ala Ala Thr Ala Pro Glu Val<br>                     725                     730                    735 | 2208 |
| aag cag ctc atc gtc gac gcc gag ggc ctc gag gac gag ctc tcc tgg<br>Lys Gln Leu Ile Val Asp Ala Glu Gly Leu Glu Asp Glu Leu Ser Trp<br>            740                     745                    750 | 2256 |
| gaa aag tcc tac gag gag gtc gct gga ggc gtc gtc acc gtc aag tcc<br>Glu Lys Ser Tyr Glu Glu Val Ala Gly Gly Val Val Thr Val Lys Ser | 2304 |

-continued

```
                755                 760                 765
gag ctc ggc gag ccc atc cac aag att gcc acg cgc ggc atc ttg ctc    2352
Glu Leu Gly Glu Pro Ile His Lys Ile Ala Thr Arg Gly Ile Leu Leu
        770                 775                 780 tgg cgc gag ttc gac aag cgc ttc ttc gac cag cct cgt ggc gag aag    2400
Trp Arg Glu Phe Asp Lys Arg Phe Phe Asp Gln Pro Arg Gly Glu Lys
785                 790                 795                 800 cgt cgc aac gcc atc atg tcc gcc aag gac gag atc att gcg cgc ctc    2448
Arg Arg Asn Ala Ile Met Ser Ala Lys Asp Glu Ile Ile Ala Arg Leu
                805                 810                 815 aac gct gac ttc caa aaa ccc tac ttt ggc cgc aag agc gac ggc tcc    2496
Asn Ala Asp Phe Gln Lys Pro Tyr Phe Gly Arg Lys Ser Asp Gly Ser
    820                 825                 830 acc tgc gac gtc gag gag atg acc tat gcc gag gtc ctc gag cgc atg    2544
Thr Cys Asp Val Glu Glu Met Thr Tyr Ala Glu Val Leu Glu Arg Met
            835                 840                 845 gtc gag ctc atg cat gta aag aac ggc ggc gac aag gcc ggc cgc ctc    2592
Val Glu Leu Met His Val Lys Asn Gly Gly Asp Lys Ala Gly Arg Leu
        850                 855                 860 gcg ccc acg cgc tgg atc gac ccc acc ttt tgc tcg cgt gtc ctt ctc    2640
Ala Pro Thr Arg Trp Ile Asp Pro Thr Phe Cys Ser Arg Val Leu Leu
865                 870                 875                 880 atg atg cag cgc gcc gcc gct cgc ttt gcg ccc aag ggc aag aag acg    2688
Met Met Gln Arg Ala Ala Ala Arg Phe Ala Pro Lys Gly Lys Lys Thr
                885                 890                 895 gcc gtg gtc gtt ccg gac aac aag ctt ctc aag gag gac ccg gac gcg    2736
Ala Val Val Val Pro Asp Asn Lys Leu Leu Lys Glu Asp Pro Asp Ala
    900                 905                 910 gcc att gcc aag ttc ctt gac gct atc ccc gcc ctg cgc gag tcc ctc    2784
Ala Ile Ala Lys Phe Leu Asp Ala Ile Pro Ala Leu Arg Glu Ser Leu
            915                 920                 925 atg gcc gac gac gat gta acc tac ttt ctc gat ctc tgc aag gtc ccg    2832
Met Ala Asp Asp Asp Val Thr Tyr Phe Leu Asp Leu Cys Lys Val Pro
        930                 935                 940 acg cgc ggc aag ccc gtc aac ttc atc ccc gtc gtc gac gag gac ctc    2880
Thr Arg Gly Lys Pro Val Asn Phe Ile Pro Val Val Asp Glu Asp Leu
945                 950                 955                 960 ggc ttc tgg ctc aag aag gat tcg ctc tgg tac tcg gag cag ctc gac    2928
Gly Phe Trp Leu Lys Lys Asp Ser Leu Trp Tyr Ser Glu Gln Leu Asp
                965                 970                 975 gct gtg ccg ggc cgc gat ccc ggc cgc gtg tgc atc ctc cac ggc cct    2976
Ala Val Pro Gly Arg Asp Pro Gly Arg Val Cys Ile Leu His Gly Pro
    980                 985                 990 gtg gcc gcg cgc ttc tcc acc aag  gtc gac gag ccc atc  gcc gac att    3024
Val Ala Ala Arg Phe Ser Thr Lys  Val Asp Glu Pro Ile  Ala Asp Ile
            995                 1000                1005 ctt ggc  ggc atc cac gcc gat  atc gtc aag tcc atc  aag tgc gat    3069
Leu Gly  Gly Ile His Ala Asp  Ile Val Lys Ser Ile  Lys Cys Asp
        1010                1015                1020 gag atc  aag gtc agc gtg ctc  tcg cct cag tct ctc  cac gat gcc    3114
Glu Ile  Lys Val Ser Val Leu  Ser Pro Gln Ser Leu  His Asp Ala
    1025                1030                1035 tcg gtc  ctg cgc atc atc tcg  gag acg ccc ttt ttg  gtg cgt ggc    3159
Ser Val  Leu Arg Ile Ile Ser  Glu Thr Pro Phe Leu  Val Arg Gly
        1040                1045                1050 aaa tcc  ttt gtg ccc aac ccc  att ggc cgc gtc gtc  aag cgc gag    3204
Lys Ser  Phe Val Pro Asn Pro  Ile Gly Arg Val Val  Lys Arg Glu
    1055                1060                1065 ggc ttt  gag cac tct tcc ttt  ggc gag gac ggc atc  acc gtt cag    3249
Gly Phe  Glu His Ser Ser Phe  Gly Glu Asp Gly Ile  Thr Val Gln
```

```
                Gly Phe Glu His Ser Ser Phe Gly Glu Asp Gly Ile Thr Val Gln
                    1070            1075            1080 gac ccg gag cgc ggt ctt acc gtc gcc acc gtg tcc cag gtt ggc           3294
Asp Pro Glu Arg Gly Leu Thr Val Ala Thr Val Ser Gln Val Gly
    1085            1090            1095 agc tcc ggc acc gag atc gag ttc aag gtc ttt gac aag gag gct           3339
Ser Ser Gly Thr Glu Ile Glu Phe Lys Val Phe Asp Lys Glu Ala
1100            1105            1110 ggc gcc gtc ctc aag cag acc ttt acc gtc gac ctg acc tcg ccc           3384
Gly Ala Val Leu Lys Gln Thr Phe Thr Val Asp Leu Thr Ser Pro
    1115            1120            1125 cgc ccg ctc ttc cag acc gag gag aac aac ctt gcg gcc acc aag           3429
Arg Pro Leu Phe Gln Thr Glu Glu Asn Asn Leu Ala Ala Thr Lys
    1130            1135            1140 cag ctc tac cgc gcc gca tgg gac tgc cag gac gag tac cac gcc           3474
Gln Leu Tyr Arg Ala Ala Trp Asp Cys Gln Asp Glu Tyr His Ala
    1145            1150            1155 gga gac acc ttt acc gac gag atc acc gtc acg gcc gac aac atc           3519
Gly Asp Thr Phe Thr Asp Glu Ile Thr Val Thr Ala Asp Asn Ile
    1160            1165            1170 gag gcc ttc aac ctt ggc acg tcg gat gag tac tcg ggc agc gcc           3564
Glu Ala Phe Asn Leu Gly Thr Ser Asp Glu Tyr Ser Gly Ser Ala
    1175            1180            1185 gag gcg ccg acc gac att tcc atc atg gcc ggc tgg cgc ccg ctg           3609
Glu Ala Pro Thr Asp Ile Ser Ile Met Ala Gly Trp Arg Pro Leu
    1190            1195            1200 gcg cgc gcg ctc ttt gtc gag gag ctc aag agc aac ctc ctc aag           3654
Ala Arg Ala Leu Phe Val Glu Glu Leu Lys Ser Asn Leu Leu Lys
    1205            1210            1215 ctc gtg cac ctt acc aac ggc att cgt ctc ccc aac ccg gcg acg           3699
Leu Val His Leu Thr Asn Gly Ile Arg Leu Pro Asn Pro Ala Thr
    1220            1225            1230 cgc acc ccg gtc aag gct ggc gag gtc atc cgc tcc gag gct cgc           3744
Arg Thr Pro Val Lys Ala Gly Glu Val Ile Arg Ser Glu Ala Arg
    1235            1240            1245 atc acg ggt atc acc atc cag ccc aag gtc ggc aag aag gtg cag           3789
Ile Thr Gly Ile Thr Ile Gln Pro Lys Val Gly Lys Lys Val Gln
    1250            1255            1260 gtc aag ggt cgc att acg cgc gcc aag gac agc acc tcg gag ccg           3834
Val Lys Gly Arg Ile Thr Arg Ala Lys Asp Ser Thr Ser Glu Pro
    1265            1270            1275 cag atg tgg gtc gag atg aac tcg gag ttc ctc att cgc ggc atc           3879
Gln Met Trp Val Glu Met Asn Ser Glu Phe Leu Ile Arg Gly Ile
    1280            1285            1290 aac gag acc ccg gaa gag tac gcc acc acg ttc gag gag acc ccc           3924
Asn Glu Thr Pro Glu Glu Tyr Ala Thr Thr Phe Glu Glu Thr Pro
    1295            1300            1305 gcc gag cgc cat atc att gag gtc aag gac gag acc gtt gcc gag           3969
Ala Glu Arg His Ile Ile Glu Val Lys Asp Glu Thr Val Ala Glu
    1310            1315            1320 ctc ctc atg tcc cgc gct tgg atc aag ctc gag tcc ggc gtc aag           4014
Leu Leu Met Ser Arg Ala Trp Ile Lys Leu Glu Ser Gly Val Lys
    1325            1330            1335 atc cac gag ggc gat cgc gtc acg att gac ctt ggc acc atc tcg           4059
Ile His Glu Gly Asp Arg Val Thr Ile Asp Leu Gly Thr Ile Ser
    1340            1345            1350 aac cgc ttt gcc ggc cct ggc cgt ctt gtt gac atc aag gcc tca           4104
Asn Arg Phe Ala Gly Pro Gly Arg Leu Val Asp Ile Lys Ala Ser
    1355            1360            1365
```

| | |
|---|---|
| ggt aac gtc ttt atc gag acc acc gcc aag tcg ccg cgc cag ttc<br>Gly Asn Val Phe Ile Glu Thr Thr Ala Lys Ser Pro Arg Gln Phe<br>1370                      1375                      1380 | 4149 |
| cct gct tcg ccg tcg cac tcg gcc ggc agc gtg ccg agc gac gac<br>Pro Ala Ser Pro Ser His Ser Ala Gly Ser Val Pro Ser Asp Asp<br>1385                      1390                      1395 | 4194 |
| ttt atc aac gtg gac tcc agc tcg ggt acc tcg aag gtt ggc gtt<br>Phe Ile Asn Val Asp Ser Ser Ser Gly Thr Ser Lys Val Gly Val<br>1400                      1405                      1410 | 4239 |
| gtt gac ttt gcc act tcg gac ggc cag gag ttc cag gtg aac cct<br>Val Asp Phe Ala Thr Ser Asp Gly Gln Glu Phe Gln Val Asn Pro<br>1415                      1420                      1425 | 4284 |
| gtg ctt tcc ttt ctc gaa aag tac agc gaa gcc aag aac ttg ggc<br>Val Leu Ser Phe Leu Glu Lys Tyr Ser Glu Ala Lys Asn Leu Gly<br>1430                      1435                      1440 | 4329 |
| cat gtt gcc gag aac ggc ggc tac gag ctc ttt gac gag ccg gcc<br>His Val Ala Glu Asn Gly Gly Tyr Glu Leu Phe Asp Glu Pro Ala<br>1445                      1450                      1455 | 4374 |
| gtt gtc aag gcc cct gcc gac tgc acg acc tat gct cgt ggc tcg<br>Val Val Lys Ala Pro Ala Asp Cys Thr Thr Tyr Ala Arg Gly Ser<br>1460                      1465                      1470 | 4419 |
| cgg gac gcc aac ccg att cat cgc gag gag gca ttt gca gtc ctc<br>Arg Asp Ala Asn Pro Ile His Arg Glu Glu Ala Phe Ala Val Leu<br>1475                      1480                      1485 | 4464 |
| gcg gac ctt ccg gat ggc aag ccc att gtt cac ggc atg tgg acc<br>Ala Asp Leu Pro Asp Gly Lys Pro Ile Val His Gly Met Trp Thr<br>1490                      1495                      1500 | 4509 |
| gcc tgc atg gcc cgt gct cgt ctc gaa gag atc gcc gcc aag ggt<br>Ala Cys Met Ala Arg Ala Arg Leu Glu Glu Ile Ala Ala Lys Gly<br>1505                      1510                      1515 | 4554 |
| gac ctc aag cgc atc gtc tcg tac gag gcc tcc ttt gtg gac atg<br>Asp Leu Lys Arg Ile Val Ser Tyr Glu Ala Ser Phe Val Asp Met<br>1520                      1525                      1530 | 4599 |
| gtg cac tgc agc gac gag ctc gtc gtg acg gcc aag cag acg ggc<br>Val His Cys Ser Asp Glu Leu Val Val Thr Ala Lys Gln Thr Gly<br>1535                      1540                      1545 | 4644 |
| gtc aag aac ggc ctc atg ctt gtc acg gtc agc gtg aac cgc acc<br>Val Lys Asn Gly Leu Met Leu Val Thr Val Ser Val Asn Arg Thr<br>1550                      1555                      1560 | 4689 |
| tcg gac cgc gcc ctg gtc atg acg gcg cgc gct gag ctc gag cag<br>Ser Asp Arg Ala Leu Val Met Thr Ala Arg Ala Glu Leu Glu Gln<br>1565                      1570                      1575 | 4734 |
| ccg tcg acg gct tac ctg ttc acc ggc cag ggt tcg gcg tcc aag<br>Pro Ser Thr Ala Tyr Leu Phe Thr Gly Gln Gly Ser Ala Ser Lys<br>1580                      1585                      1590 | 4779 |
| ggc atg ggc atg gac cgc tac gcg gcc agc gcg acc gtg cgc aac<br>Gly Met Gly Met Asp Arg Tyr Ala Ala Ser Ala Thr Val Arg Asn<br>1595                      1600                      1605 | 4824 |
| gtc tgg gac cgt gcc gag gac tac ctc cgc gct cgc ttt ggc ttt<br>Val Trp Asp Arg Ala Glu Asp Tyr Leu Arg Ala Arg Phe Gly Phe<br>1610                      1615                      1620 | 4869 |
| tct atc ctg cag att gtc cgc gag aac ccc aag tcg ttc acg gtg<br>Ser Ile Leu Gln Ile Val Arg Glu Asn Pro Lys Ser Phe Thr Val<br>1625                      1630                      1635 | 4914 |
| cac ttt ggt ggc ccg cgt ggc aag gcc att cgc gag aac ctg cgc<br>His Phe Gly Gly Pro Arg Gly Lys Ala Ile Arg Glu Asn Leu Arg<br>1640                      1645                      1650 | 4959 |
| aac ctc acg gcg cag gac cca agc acg ggc cag aac gtg cct ctc<br>Asn Leu Thr Ala Gln Asp Pro Ser Thr Gly Gln Asn Val Pro Leu<br>1655                      1660                      1665 | 5004 |

-continued

| | | |
|---|---|---|
| ctc ccg gag atc tcg gcg acg acc aag tcc ttt acg ttc aac tcg<br>Leu Pro Glu Ile Ser Ala Thr Thr Lys Ser Phe Thr Phe Asn Ser<br>1670                     1675                     1680 | 5049 |
| ccc acc ggt ctg ctc ttt gcc acg cag ttc tcg cag ccc gct ctc<br>Pro Thr Gly Leu Leu Phe Ala Thr Gln Phe Ser Gln Pro Ala Leu<br>1685                     1690                     1695 | 5094 |
| gtg ctc gtg caa aag gcc gcc ttt gag gag ctc cgc gag gcc ggc<br>Val Leu Val Gln Lys Ala Ala Phe Glu Glu Leu Arg Glu Ala Gly<br>1700                     1705                     1710 | 5139 |
| ctc gtg cct gag aag gcc ctg ttt gcg ggt cat tcg ctc ggt gag<br>Leu Val Pro Glu Lys Ala Leu Phe Ala Gly His Ser Leu Gly Glu<br>1715                     1720                     1725 | 5184 |
| tac gcc gct ctt gcc ggc tat gcc gat tcg ctg acc atc gag gac<br>Tyr Ala Ala Leu Ala Gly Tyr Ala Asp Ser Leu Thr Ile Glu Asp<br>1730                     1735                     1740 | 5229 |
| ctc gtc gag acg gtc ttc ctg cgt ggt atg gtc atg cag aac gcc<br>Leu Val Glu Thr Val Phe Leu Arg Gly Met Val Met Gln Asn Ala<br>1745                     1750                     1755 | 5274 |
| gtc ccc cgc gac agc gag ggt cgc tcg aac tac gcc atg gtt gcc<br>Val Pro Arg Asp Ser Glu Gly Arg Ser Asn Tyr Ala Met Val Ala<br>1760                     1765                     1770 | 5319 |
| gcg aac ccg ctc cgc gtc ggc cgc ggc ttc acg ccg gag atg ctc<br>Ala Asn Pro Leu Arg Val Gly Arg Gly Phe Thr Pro Glu Met Leu<br>1775                     1780                     1785 | 5364 |
| agc gag att gtg gat ctc atc acc gag aac gag gag atg ggc aag<br>Ser Glu Ile Val Asp Leu Ile Thr Glu Asn Glu Glu Met Gly Lys<br>1790                     1795                     1800 | 5409 |
| ccg ctg ctg cag att gtc aac ttt aac gtc cgc ttc acg cag tac<br>Pro Leu Leu Gln Ile Val Asn Phe Asn Val Arg Phe Thr Gln Tyr<br>1805                     1810                     1815 | 5454 |
| gtt gtg gcc ggt gag ctg ctg gcc ctc gat gcg ctt gcg gag gcc<br>Val Val Ala Gly Glu Leu Leu Ala Leu Asp Ala Leu Ala Glu Ala<br>1820                     1825                     1830 | 5499 |
| ctg aac ctg gcc ttt gcc aag ggc gtt cgc gac gtg gcc gct ctg<br>Leu Asn Leu Ala Phe Ala Lys Gly Val Arg Asp Val Ala Ala Leu<br>1835                     1840                     1845 | 5544 |
| gcc gag cac ggc gcc aag acg gcc cag gcc agt ctt gcc aag cgc<br>Ala Glu His Gly Ala Lys Thr Ala Gln Ala Ser Leu Ala Lys Arg<br>1850                     1855                     1860 | 5589 |
| aat ggc cgc gcc gag ccc ctc aag cgc ggc aag gcg acc atc cct<br>Asn Gly Arg Ala Glu Pro Leu Lys Arg Gly Lys Ala Thr Ile Pro<br>1865                     1870                     1875 | 5634 |
| ctt ccc ggc atc gat gtg ccc ttc cac tcg cgc aag ctc ctc ccc<br>Leu Pro Gly Ile Asp Val Pro Phe His Ser Arg Lys Leu Leu Pro<br>1880                     1885                     1890 | 5679 |
| ggc gtc ggc gcc ttc cgc aag ctg ctc gcg ccg cgt ttc agc ctc<br>Gly Val Gly Ala Phe Arg Lys Leu Leu Ala Pro Arg Phe Ser Leu<br>1895                     1900                     1905 | 5724 |
| cag acc atg gag aag atc atc gat cgc ctt gtc ggc aac tac att<br>Gln Thr Met Glu Lys Ile Ile Asp Arg Leu Val Gly Asn Tyr Ile<br>1910                     1915                     1920 | 5769 |
| ccc aac gtc acg gcc gag gtg ctc agt ctc gac cgc gcc tat gcc<br>Pro Asn Val Thr Ala Glu Val Leu Ser Leu Asp Arg Ala Tyr Ala<br>1925                     1930                     1935 | 5814 |
| gaa aag gtt caa aag gtg acg ggc tcg cag ccg atg gcg gag ctc<br>Glu Lys Val Gln Lys Val Thr Gly Ser Gln Pro Met Ala Glu Leu<br>1940                     1945                     1950 | 5859 |
| ctc gag gac ttt gac act gcc aca gac gcc gaa aag gtg cgc act<br>Leu Glu Asp Phe Asp Thr Ala Thr Asp Ala Glu Lys Val Arg Thr | 5904 |

-continued

```
            1955                1960                1965
ctt gtg att gag ctc ctc gct cac cag ttc gcc atg ccg gtg cgc     5949
Leu Val Ile Glu Leu Leu Ala His Gln Phe Ala Met Pro Val Arg
    1970                1975                1980 tgg atc gag acg cag gac ctt atg ttc ggc tcg cat gtc gag cgt     5994
Trp Ile Glu Thr Gln Asp Leu Met Phe Gly Ser His Val Glu Arg
    1985                1990                1995 gtt atc gag atg ggc cct tcc gcg acg ctc acg gcc atg gcg aag     6039
Val Ile Glu Met Gly Pro Ser Ala Thr Leu Thr Ala Met Ala Lys
    2000                2005                2010 cag acg gtc aag tcg ggc gcc tac ggc gat gcc gag gag tac agc     6084
Gln Thr Val Lys Ser Gly Ala Tyr Gly Asp Ala Glu Glu Tyr Ser
    2015                2020                2025 ccg gag att atg tgg tgg aag cag gac cgc gac tcc gtg tac tac     6129
Pro Glu Ile Met Trp Trp Lys Gln Asp Arg Asp Ser Val Tyr Tyr
    2030                2035                2040 gaa gtc gag aac gtt ggc ccg tcc ttt ggc gac tac atg gac gag     6174
Glu Val Glu Asn Val Gly Pro Ser Phe Gly Asp Tyr Met Asp Glu
    2045                2050                2055 cgc gcc gct ctc gag gag gag ctc gcc gcg gcc aag gct gcc aag     6219
Arg Ala Ala Leu Glu Glu Glu Leu Ala Ala Ala Lys Ala Ala Lys
    2060                2065                2070 gcc gag ccc aag gcg gag gcg gct tcc aag gcc gag gcc gct cct     6264
Ala Glu Pro Lys Ala Glu Ala Ala Ser Lys Ala Glu Ala Ala Pro
    2075                2080                2085 gcg ccc aag gcc gcc gcg ccc gcg ccc aag gcg gct gcc ccg gcc     6309
Ala Pro Lys Ala Ala Ala Pro Ala Pro Lys Ala Ala Ala Pro Ala
    2090                2095                2100 cct gcc gca ccc gct ccc gct ccc gca gcg ccc gct cct gct ccg     6354
Pro Ala Ala Pro Ala Pro Ala Pro Ala Ala Pro Ala Pro Ala Pro
    2105                2110                2115 gct gcg ggt ggc tcc gtt gcg gat gcc ccg ccc gac gcc aag cac     6399
Ala Ala Gly Gly Ser Val Ala Asp Ala Pro Pro Asp Ala Lys His
    2120                2125                2130 gtc ctc cgc gcc ctg ctc gcg gcc aag ctc aag aag tca atg ggc     6444
Val Leu Arg Ala Leu Leu Ala Ala Lys Leu Lys Lys Ser Met Gly
    2135                2140                2145 gac gtc cct gcg tcc acc acg gtc cag gcc ctc agc gcc ggt cgt     6489
Asp Val Pro Ala Ser Thr Thr Val Gln Ala Leu Ser Ala Gly Arg
    2150                2155                2160 agt gcc gtg cag aac gag gtc atg ggc gag ctc tcg gcc gag ttc     6534
Ser Ala Val Gln Asn Glu Val Met Gly Glu Leu Ser Ala Glu Phe
    2165                2170                2175 aag ggt gcc atc cct gac aac gcc ggc gag atg ccc ctt gcc gag     6579
Lys Gly Ala Ile Pro Asp Asn Ala Gly Glu Met Pro Leu Ala Glu
    2180                2185                2190 ctc ggt ggc aac ctt tcg agc tac aag gac ccc ggt ccg gtg acg     6624
Leu Gly Gly Asn Leu Ser Ser Tyr Lys Asp Pro Gly Pro Val Thr
    2195                2200                2205 caa aag ctc gtg gcc cgc acc cta agc gcg gcg ctg ccc ggt ggc     6669
Gln Lys Leu Val Ala Arg Thr Leu Ser Ala Ala Leu Pro Gly Gly
    2210                2215                2220 ttt ggc gcc aac gct gcc aag gac tac ctc ggc cag cac tgg ggt     6714
Phe Gly Ala Asn Ala Ala Lys Asp Tyr Leu Gly Gln His Trp Gly
    2225                2230                2235 ctc ggc gcc ggt cgc acg ttc tcc gtg ctt ctc cat gcc acg act     6759
Leu Gly Ala Gly Arg Thr Phe Ser Val Leu Leu His Ala Thr Thr
    2240                2245                2250 atg gcc ccg gag aag cgc ctc aag tcg gag gag gag ggc aag cag     6804
```

```
                Met Ala Pro Glu Lys Arg Leu Lys Ser Glu Glu Glu Gly Lys Gln
                    2255                2260                2265 tgg ctc gac gac gtg tgc aag tcg tac ggc cag gat gcc ggt gtc                6849
Trp Leu Asp Asp Val Cys Lys Ser Tyr Gly Gln Asp Ala Gly Val
    2270                2275                2280 tcg ctg tct cct ggt ggt ggc agc gcc ggc gcc gcc gca gcc gcg                6894
Ser Leu Ser Pro Gly Gly Gly Ser Ala Gly Ala Ala Ala Ala Ala
    2285                2290                2295 ccc atg atg atg atg cag cag tct ggt ccc gct gcg gcg cct ccc                6939
Pro Met Met Met Met Gln Gln Ser Gly Pro Ala Ala Ala Pro Pro
    2300                2305                2310 ccc gat gcc ccc gtg tcg gct ctt cac gcg atg cgc gtc atg ctt                6984
Pro Asp Ala Pro Val Ser Ala Leu His Ala Met Arg Val Met Leu
    2315                2320                2325 gcg gcc aaa ttc gaa aag ggc ttt gcc gac gtc gcg gat tcg gct                7029
Ala Ala Lys Phe Glu Lys Gly Phe Ala Asp Val Ala Asp Ser Ala
    2330                2335                2340 acg gtt gct gct ctg agc aac ggc aag agt gct gtc cag aac gag                7074
Thr Val Ala Ala Leu Ser Asn Gly Lys Ser Ala Val Gln Asn Glu
    2345                2350                2355 gtc gcc ggt gac ttt ggc gcc gag ttt ggc gag gtc gag gag gct                7119
Val Ala Gly Asp Phe Gly Ala Glu Phe Gly Glu Val Glu Glu Ala
    2360                2365                2370 gcg cag acg ccg ctc tcc gag ctt gcc ggc aag gtc cag gga agc                7164
Ala Gln Thr Pro Leu Ser Glu Leu Ala Gly Lys Val Gln Gly Ser
    2375                2380                2385 tac aac ggc cct ggc aag gtc ctc acg cgc gat gtc aac aag ctc                7209
Tyr Asn Gly Pro Gly Lys Val Leu Thr Arg Asp Val Asn Lys Leu
    2390                2395                2400 ctc ggc cag tgc ctc ccc ggt ggc ttt ggt gcc agc gcc gcg cgc                7254
Leu Gly Gln Cys Leu Pro Gly Gly Phe Gly Ala Ser Ala Ala Arg
    2405                2410                2415 tcg tac ctg tct ggc gac cgc atg ctg ccc gct gga cgt gtc gag                7299
Ser Tyr Leu Ser Gly Asp Arg Met Leu Pro Ala Gly Arg Val Glu
    2420                2425                2430 tct gtg ctc att cat ggt ctg tgc atg gct ccc aag ggc cgt ctg                7344
Ser Val Leu Ile His Gly Leu Cys Met Ala Pro Lys Gly Arg Leu
    2435                2440                2445 ggc tcc ccc gag gat gcc aag gcc tgg ctc gac agc ctc tgc tcc                7389
Gly Ser Pro Glu Asp Ala Lys Ala Trp Leu Asp Ser Leu Cys Ser
    2450                2455                2460 gcg tac ggt agc ttt gca ggc atc acc atc ccg acg ccc ggc tcg                7434
Ala Tyr Gly Ser Phe Ala Gly Ile Thr Ile Pro Thr Pro Gly Ser
    2465                2470                2475 ggc ggc ggt ggc gcc gct atg ggc ttt gcc ggc ggc ccg cag gtc                7479
Gly Gly Gly Gly Ala Ala Met Gly Phe Ala Gly Gly Pro Gln Val
    2480                2485                2490 tct tcg gcc gag ttg agc gcc ctc aag tcc gac gtg cag gcc atg                7524
Ser Ser Ala Glu Leu Ser Ala Leu Lys Ser Asp Val Gln Ala Met
    2495                2500                2505 gtg gag tcc cag ctc gat gcc ctg cgc cgc ttc ctg gac att gac                7569
Val Glu Ser Gln Leu Asp Ala Leu Arg Arg Phe Leu Asp Ile Asp
    2510                2515                2520 ccg ctt cat gcc gac aag ctt ctc gag ctt gag aag cag gtg cgc                7614
Pro Leu His Ala Asp Lys Leu Leu Glu Leu Glu Lys Gln Val Arg
    2525                2530                2535 gcg gag acc gag tcg aag ctg gac tcg atc cac gcc gag atg acg                7659
Ala Glu Thr Glu Ser Lys Leu Asp Ser Ile His Ala Glu Met Thr
    2540                2545                2550
```

| | |
|---|---|
| gtg gac ttt tgc gag cgg gtc cag ccc cag ttc gac gag aac cgt<br>Val Asp Phe Cys Glu Arg Val Gln Pro Gln Phe Asp Glu Asn Arg<br>2555                     2560                     2565 | 7704 |
| gtc cgc gtc tac gac tcg ttc tgg aac tgg gtc gtc cag gac gcc<br>Val Arg Val Tyr Asp Ser Phe Trp Asn Trp Val Val Gln Asp Ala<br>2570                     2575                     2580 | 7749 |
| atg cag atg cac ctc cac gtg ctc ggc cgc ctc gag gcc gcg cgc<br>Met Gln Met His Leu His Val Leu Gly Arg Leu Glu Ala Ala Arg<br>2585                     2590                     2595 | 7794 |
| cag ggc aag gag gtt aac gcc tcg gcg gac tcg aac ccg cac ttt<br>Gln Gly Lys Glu Val Asn Ala Ser Ala Asp Ser Asn Pro His Phe<br>2600                     2605                     2610 | 7839 |
| gac gag atg tcc aag tgg ctc ttg ggc tcc agc tct tcg gac gcg<br>Asp Glu Met Ser Lys Trp Leu Leu Gly Ser Ser Ser Ser Asp Ala<br>2615                     2620                     2625 | 7884 |
| ccc ccc att gcc tgg ttc cgc aac ttt ttg tgc aac cgt gcg acc<br>Pro Pro Ile Ala Trp Phe Arg Asn Phe Leu Cys Asn Arg Ala Thr<br>2630                     2635                     2640 | 7929 |
| ccg cag ctc ctg cag gcg gtc aag ttc ttt gcc aac tca atg cac<br>Pro Gln Leu Leu Gln Ala Val Lys Phe Phe Ala Asn Ser Met His<br>2645                     2650                     2655 | 7974 |
| gat gct ggc tac gtc gac tac gcc cag gcc att tcg ctc ctt gct<br>Asp Ala Gly Tyr Val Asp Tyr Ala Gln Ala Ile Ser Leu Leu Ala<br>2660                     2665                     2670 | 8019 |
| gag cag gtc aag aac tgg ctc aac aat gtc ccc gtg cat gtt gcc<br>Glu Gln Val Lys Asn Trp Leu Asn Asn Val Pro Val His Val Ala<br>2675                     2680                     2685 | 8064 |
| aac ttt gag ccc aag gcg ccc cag gtc cgc gtg ctc gac gat ggc<br>Asn Phe Glu Pro Lys Ala Pro Gln Val Arg Val Leu Asp Asp Gly<br>2690                     2695                     2700 | 8109 |
| gtc gtc gac tac ttt gag atc gac cgc gac ggc gtc aac gat gcg<br>Val Val Asp Tyr Phe Glu Ile Asp Arg Asp Gly Val Asn Asp Ala<br>2705                     2710                     2715 | 8154 |
| gcc cgc tac gtt gcc gag atg agc cgt ggc ctc tac tac aag cgc<br>Ala Arg Tyr Val Ala Glu Met Ser Arg Gly Leu Tyr Tyr Lys Arg<br>2720                     2725                     2730 | 8199 |
| acg ggc ccg tcc cgc gtg gag aac ccc tcg cag acg gtc aat gtt<br>Thr Gly Pro Ser Arg Val Glu Asn Pro Ser Gln Thr Val Asn Val<br>2735                     2740                     2745 | 8244 |
| gcc ggc gac ggt cgc ctc acg ctt ttg gag ctg ccg cct tcg cag<br>Ala Gly Asp Gly Arg Leu Thr Leu Leu Glu Leu Pro Pro Ser Gln<br>2750                     2755                     2760 | 8289 |
| agc gag atc gag gcg gtt gcg ggc gct ggc tgg cgt ttg cct cga<br>Ser Glu Ile Glu Ala Val Ala Gly Ala Gly Trp Arg Leu Pro Arg<br>2765                     2770                     2775 | 8334 |
| tcg gag gcc gag ctt gcg cgc gag ctc acg ggc gag cct ctt tct<br>Ser Glu Ala Glu Leu Ala Arg Glu Leu Thr Gly Glu Pro Leu Ser<br>2780                     2785                     2790 | 8379 |
| ctg gac act agc gag acg agc agc gag gag ggc gac ctt ccc gat<br>Leu Asp Thr Ser Glu Thr Ser Ser Glu Glu Gly Asp Leu Pro Asp<br>2795                     2800                     2805 | 8424 |
| ggc ccg acg ctc gat cgc ctc cgc gcc tcg gtg aac cgt ggc gtg<br>Gly Pro Thr Leu Asp Arg Leu Arg Ala Ser Val Asn Arg Gly Val<br>2810                     2815                     2820 | 8469 |
| ggc ggc gac gag gcc gag ggt ggc gag ggc aag atc tcg acg gcc<br>Gly Gly Asp Glu Ala Glu Gly Gly Glu Gly Lys Ile Ser Thr Ala<br>2825                     2830                     2835 | 8514 |
| tcg ctc aag aac ggc tac gag agc atc cac gtg tcc aag cag gtg<br>Ser Leu Lys Asn Gly Tyr Glu Ser Ile His Val Ser Lys Gln Val<br>2840                     2845                     2850 | 8559 |

| | | |
|---|---|---|
| ccc tac gtg cac ctc aag tcg ctc tcg ggt gtc gac aag tct gtt<br>Pro Tyr Val His Leu Lys Ser Leu Ser Gly Val Asp Lys Ser Val<br>2855                      2860                 2865 | 8604 |
| cgc atc ctc aac gag cag ctc act tcc gag tac ttt tcg tgc atg<br>Arg Ile Leu Asn Glu Gln Leu Thr Ser Glu Tyr Phe Ser Cys Met<br>2870                      2875                 2880 | 8649 |
| gat gag att gcc acc agc ggt gtg agc ttt gcc ggc cag gtt gct<br>Asp Glu Ile Ala Thr Ser Gly Val Ser Phe Ala Gly Gln Val Ala<br>2885                      2890                 2895 | 8694 |
| ctc gtc acg ggt gcc ggt tcg ggc tca atc ggt gct gag ctg gtc<br>Leu Val Thr Gly Ala Gly Ser Gly Ser Ile Gly Ala Glu Leu Val<br>2900                      2905                 2910 | 8739 |
| aag tcg ctc ctc gag ggt ggc gcg acg gtc ttg gca gcc atc cgc<br>Lys Ser Leu Leu Glu Gly Gly Ala Thr Val Leu Ala Ala Ile Arg<br>2915                      2920                 2925 | 8784 |
| acg gcg cgg tcc gag gcg gcg ctc acc aag gag tac gct cgc ttc<br>Thr Ala Arg Ser Glu Ala Ala Leu Thr Lys Glu Tyr Ala Arg Phe<br>2930                      2935                 2940 | 8829 |
| cag agc att tac aag gag ttt ggc gcc aag gac agc aag ctg tac<br>Gln Ser Ile Tyr Lys Glu Phe Gly Ala Lys Asp Ser Lys Leu Tyr<br>2945                      2950                 2955 | 8874 |
| ctt gtc cct tgc aac tgt gcc tcg cag cag gac atg aag tcg ctt<br>Leu Val Pro Cys Asn Cys Ala Ser Gln Gln Asp Met Lys Ser Leu<br>2960                      2965                 2970 | 8919 |
| gtc tct tat acg tac gac aag ctc ggt ctg gac gtg gac ttt gtt<br>Val Ser Tyr Thr Tyr Asp Lys Leu Gly Leu Asp Val Asp Phe Val<br>2975                      2980                 2985 | 8964 |
| gtg cct ttt gcg gct gcc gcg cag cag ggc aag gac att tcc tcg<br>Val Pro Phe Ala Ala Ala Ala Gln Gln Gly Lys Asp Ile Ser Ser<br>2990                      2995                 3000 | 9009 |
| atc gac gct tcg tca gag gtc tcg cac cgc atg atg atg acc aac<br>Ile Asp Ala Ser Ser Glu Val Ser His Arg Met Met Met Thr Asn<br>3005                      3010                 3015 | 9054 |
| gtg gtc cgt ctt ctc ggc gcc ctc aag gac gcc aag acg tcg cgt<br>Val Val Arg Leu Leu Gly Ala Leu Lys Asp Ala Lys Thr Ser Arg<br>3020                      3025                 3030 | 9099 |
| gac atc acc acg cgc cct gct atg gtt ctc att ccg tgc tcc ccg<br>Asp Ile Thr Thr Arg Pro Ala Met Val Leu Ile Pro Cys Ser Pro<br>3035                      3040                 3045 | 9144 |
| aac cac ggt gag ttt ggc cag gat ggc ctt tac gcc gag tcc aag<br>Asn His Gly Glu Phe Gly Gln Asp Gly Leu Tyr Ala Glu Ser Lys<br>3050                      3055                 3060 | 9189 |
| ctt gga tgc gag gcc ctg ctc aac aag tgg tcg agc gag ggc tgg<br>Leu Gly Cys Glu Ala Leu Leu Asn Lys Trp Ser Ser Glu Gly Trp<br>3065                      3070                 3075 | 9234 |
| ggc gac tac ctc agt ctt gcg gcg tgc gtc att ggc tgg acg cgt<br>Gly Asp Tyr Leu Ser Leu Ala Ala Cys Val Ile Gly Trp Thr Arg<br>3080                      3085                 3090 | 9279 |
| tct gcg ctg atg cag cac aac aac att gtg gcc ccg ggc atc gag<br>Ser Ala Leu Met Gln His Asn Asn Ile Val Ala Pro Gly Ile Glu<br>3095                      3100                 3105 | 9324 |
| aag ctt ggt tgc cgc act ttt gcc ccc gag gag acg aac ttt aac<br>Lys Leu Gly Cys Arg Thr Phe Ala Pro Glu Glu Thr Asn Phe Asn<br>3110                      3115                 3120 | 9369 |
| ctt gtg ggc ctc ctg cac ccg cgc atg gtc acc ctt gct gcg gag<br>Leu Val Gly Leu Leu His Pro Arg Met Val Thr Leu Ala Ala Glu<br>3125                      3130                 3135 | 9414 |
| gag ccg ctg tgg gcc gat ctc acg ggc tgc tgg aca gtc atc ccg<br>Glu Pro Leu Trp Ala Asp Leu Thr Gly Cys Trp Thr Val Ile Pro | 9459 |

|         |         |         |         |         |         |         |         |         |         |         |         |         |         |         |       |
|---------|---------|---------|---------|---------|---------|---------|---------|---------|---------|---------|---------|---------|---------|---------|-------|
|         | 3140    |         |         |         | 3145    |         |         |         | 3150    |         |         |         |         |         |       |
| aac     | atg     | aag     | gat     | gcc     | gct     | gac     | agc     | ctt     | cgt     | agc     | ggt     | ctc     | atg     | tca     | 9504  |
| Asn     | Met     | Lys     | Asp     | Ala     | Ala     | Asp     | Ser     | Leu     | Arg     | Ser     | Gly     | Leu     | Met     | Ser     |       |
|         | 3155    |         |         |         | 3160    |         |         |         | 3165    |         |         |         |         |         |       |
| aag     | tcg     | cgc     | gtc     | gcg     | cgc     | gcc     | att     | gcc     | gcg     | agc     | aac     | cag     | ctc     | gag     | 9549  |
| Lys     | Ser     | Arg     | Val     | Ala     | Arg     | Ala     | Ile     | Ala     | Ala     | Ser     | Asn     | Gln     | Leu     | Glu     |       |
|         | 3170    |         |         |         | 3175    |         |         |         | 3180    |         |         |         |         |         |       |
| gag     | gcc     | aag     | tcg     | gcc     | gat     | gtc     | tcg     | cac     | gtg     | ctg     | ccg     | ccg     | ccc     | gag     | 9594  |
| Glu     | Ala     | Lys     | Ser     | Ala     | Asp     | Val     | Ser     | His     | Val     | Leu     | Pro     | Pro     | Pro     | Glu     |       |
|         | 3185    |         |         |         | 3190    |         |         |         | 3195    |         |         |         |         |         |       |
| tcg     | tct     | ggc     | ccg     | ctt     | gcc     | agc     | acg     | cag     | ttg     | ggc     | atg     | acg     | ccc     | ttc     | 9639  |
| Ser     | Ser     | Gly     | Pro     | Leu     | Ala     | Ser     | Thr     | Gln     | Leu     | Gly     | Met     | Thr     | Pro     | Phe     |       |
|         | 3200    |         |         |         | 3205    |         |         |         | 3210    |         |         |         |         |         |       |
| ccg     | gcg     | ctt     | ccg     | tcc     | gag     | gag     | gca     | cgc     | aaa     | tcg     | ctc     | agt     | gcg     | ctc     | 9684  |
| Pro     | Ala     | Leu     | Pro     | Ser     | Glu     | Glu     | Ala     | Arg     | Lys     | Ser     | Leu     | Ser     | Ala     | Leu     |       |
|         | 3215    |         |         |         | 3220    |         |         |         | 3225    |         |         |         |         |         |       |
| gag     | ggc     | atg     | gtt     | gac     | ctc     | cgc     | aag     | gtt     | gtg     | gtc     | gtg     | gtg     | ggc     | tac     | 9729  |
| Glu     | Gly     | Met     | Val     | Asp     | Leu     | Arg     | Lys     | Val     | Val     | Val     | Val     | Val     | Gly     | Tyr     |       |
|         | 3230    |         |         |         | 3235    |         |         |         | 3240    |         |         |         |         |         |       |
| ggt     | gag     | gtc     | ggc     | cct     | tgg     | ggt     | aac     | gcc     | cgc     | acg     | cgc     | tgg     | gag     | atg     | 9774  |
| Gly     | Glu     | Val     | Gly     | Pro     | Trp     | Gly     | Asn     | Ala     | Arg     | Thr     | Arg     | Trp     | Glu     | Met     |       |
|         | 3245    |         |         |         | 3250    |         |         |         | 3255    |         |         |         |         |         |       |
| gag     | agc     | tat     | ggc     | gag     | ttt     | tcg     | ctc     | gag     | ggc     | tcg     | atc     | gag     | ctc     | gct     | 9819  |
| Glu     | Ser     | Tyr     | Gly     | Glu     | Phe     | Ser     | Leu     | Glu     | Gly     | Ser     | Ile     | Glu     | Leu     | Ala     |       |
|         | 3260    |         |         |         | 3265    |         |         |         | 3270    |         |         |         |         |         |       |
| tgg     | atg     | gtc     | ggt     | ctc     | atc     | aag     | cac     | cat     | gat     | ggt     | ccg     | ctc     | ccc     | tcg     | 9864  |
| Trp     | Met     | Val     | Gly     | Leu     | Ile     | Lys     | His     | His     | Asp     | Gly     | Pro     | Leu     | Pro     | Ser     |       |
|         | 3275    |         |         |         | 3280    |         |         |         | 3285    |         |         |         |         |         |       |
| ggc     | ccg     | ccg     | cgg     | tcc     | aag     | tac     | acg     | ggc     | tgg     | gtg     | gac     | gcc     | gct     | tcg     | 9909  |
| Gly     | Pro     | Pro     | Arg     | Ser     | Lys     | Tyr     | Thr     | Gly     | Trp     | Val     | Asp     | Ala     | Ala     | Ser     |       |
|         | 3290    |         |         |         | 3295    |         |         |         | 3300    |         |         |         |         |         |       |
| ggc     | gag     | cct     | gtg     | gcc     | gac     | aac     | gag     | atc     | aag     | cgc     | cgt     | tac     | gag     | gag     | 9954  |
| Gly     | Glu     | Pro     | Val     | Ala     | Asp     | Asn     | Glu     | Ile     | Lys     | Arg     | Arg     | Tyr     | Glu     | Glu     |       |
|         | 3305    |         |         |         | 3310    |         |         |         | 3315    |         |         |         |         |         |       |
| cac     | atg     | ctc     | aag     | agc     | tgc     | ggt     | atc     | cgc     | atc     | gtt     | gag     | ccc     | gag     | ctc     | 9999  |
| His     | Met     | Leu     | Lys     | Ser     | Cys     | Gly     | Ile     | Arg     | Ile     | Val     | Glu     | Pro     | Glu     | Leu     |       |
|         | 3320    |         |         |         | 3325    |         |         |         | 3330    |         |         |         |         |         |       |
| ttt     | gag     | ggt     | tac     | aac     | ccg     | gag     | gcc     | aag     | cgc     | ttc     | ctg     | cat     | tcg     | gtc     | 10044 |
| Phe     | Glu     | Gly     | Tyr     | Asn     | Pro     | Glu     | Ala     | Lys     | Arg     | Phe     | Leu     | His     | Ser     | Val     |       |
|         | 3335    |         |         |         | 3340    |         |         |         | 3345    |         |         |         |         |         |       |
| gtt     | ctc     | gac     | cgc     | gac     | atg     | ccc     | cct     | gtc     | gag     | ctc     | tcg     | ggt     | ctc     | gag     | 10089 |
| Val     | Leu     | Asp     | Arg     | Asp     | Met     | Pro     | Pro     | Val     | Glu     | Leu     | Ser     | Gly     | Leu     | Glu     |       |
|         | 3350    |         |         |         | 3355    |         |         |         | 3360    |         |         |         |         |         |       |
| gag     | ggt     | ctt     | cag     | tac     | cgc     | aac     | gag     | ctc     | ggt     | gcg     | gac     | tgc     | tgc     | gac     | 10134 |
| Glu     | Gly     | Leu     | Gln     | Tyr     | Arg     | Asn     | Glu     | Leu     | Gly     | Ala     | Asp     | Cys     | Cys     | Asp     |       |
|         | 3365    |         |         |         | 3370    |         |         |         | 3375    |         |         |         |         |         |       |
| gtg     | tgg     | cag     | aag     | cct     | tcc     | gac     | ggc     | cag     | tgg     | atg     | atg     | cga     | gtc     | aag     | 10179 |
| Val     | Trp     | Gln     | Lys     | Pro     | Ser     | Asp     | Gly     | Gln     | Trp     | Met     | Met     | Arg     | Val     | Lys     |       |
|         | 3380    |         |         |         | 3385    |         |         |         | 3390    |         |         |         |         |         |       |
| aag     | ggc     | gcc     | gag     | gtg     | tcg     | atc     | gcc     | aag     | gcg     | ctc     | aag     | ttc     | aac     | cgc     | 10224 |
| Lys     | Gly     | Ala     | Glu     | Val     | Ser     | Ile     | Ala     | Lys     | Ala     | Leu     | Lys     | Phe     | Asn     | Arg     |       |
|         | 3395    |         |         |         | 3400    |         |         |         | 3405    |         |         |         |         |         |       |
| aac     | att     | gcg     | ggc     | cag     | atc     | ccg     | acc     | gga     | tgg     | gac     | gcg     | cgt     | cgc     | ttc     | 10269 |
| Asn     | Ile     | Ala     | Gly     | Gln     | Ile     | Pro     | Thr     | Gly     | Trp     | Asp     | Ala     | Arg     | Arg     | Phe     |       |
|         | 3410    |         |         |         | 3415    |         |         |         | 3420    |         |         |         |         |         |       |
| ggc     | ctc     | ccc     | gag     | gac     | att     | gcc     | acg     | ggt     | gtc     | gac     | ccc     | gtg     | acg     | ctg     | 10314 |
| Gly     | Leu     | Pro     | Glu     | Asp     | Ile     | Ala     | Thr     | Gly     | Val     | Asp     | Pro     | Val     | Thr     | Leu     |       |
|         | 3425    |         |         |         | 3430    |         |         |         | 3435    |         |         |         |         |         |       |
| tac     | acg     | ttg     | gtg     | agt     | act     | gtg     | gag     | gcc     | ctc     | atg     | gcc     | gcc     | ggt     | ctt     | 10359 |

```
Tyr Thr Leu Val Ser Thr Val Glu Ala Leu Met Ala Ala Gly Leu
    3440            3445                3450 tcg gac ccg tac gag ctt tac cag tac gtg cat gtc agc gag gtg    10404
Ser Asp Pro Tyr Glu Leu Tyr Gln Tyr Val His Val Ser Glu Val
    3455            3460                3465 ggt aac acc tcg ggt ggt ggc atg ggc ggc atg cgc tcg ctc aag    10449
Gly Asn Thr Ser Gly Gly Gly Met Gly Gly Met Arg Ser Leu Lys
    3470            3475                3480 cgt ctc ttc cac cag cgt gcg ctc gac gag gac atc ccg agc gac    10494
Arg Leu Phe His Gln Arg Ala Leu Asp Glu Asp Ile Pro Ser Asp
    3485            3490                3495 acg ctt gcg gag tcg ttc atc aac acc atg cct gcg tgg gtg aac    10539
Thr Leu Ala Glu Ser Phe Ile Asn Thr Met Pro Ala Trp Val Asn
    3500            3505                3510 atg ctc ttg atg agc agc tcg ggt ccg atc aag acc cca gtc ggt    10584
Met Leu Leu Met Ser Ser Ser Gly Pro Ile Lys Thr Pro Val Gly
    3515            3520                3525 gct tgc gcc acg gcc gcc gag tcg ctc gac att ggt atg gag acg    10629
Ala Cys Ala Thr Ala Ala Glu Ser Leu Asp Ile Gly Met Glu Thr
    3530            3535                3540 att ctc agt ggc aag gcc cgc gtc gtc att gct ggt ggc tac gat    10674
Ile Leu Ser Gly Lys Ala Arg Val Val Ile Ala Gly Gly Tyr Asp
    3545            3550                3555 gac ttt ggc gag gag ggc agc tac gag ttc gcg caa atg ggc gcg    10719
Asp Phe Gly Glu Glu Gly Ser Tyr Glu Phe Ala Gln Met Gly Ala
    3560            3565                3570 acc aac aac acg gac ctc gat tcg ggc cgt ggt cgc act gtc cgc    10764
Thr Asn Asn Thr Asp Leu Asp Ser Gly Arg Gly Arg Thr Val Arg
    3575            3580                3585 gag agc tcg cgc ccc atg tcg agc tcg cgt gct gga ttt gtg gag    10809
Glu Ser Ser Arg Pro Met Ser Ser Ser Arg Ala Gly Phe Val Glu
    3590            3595                3600 tcc cag ggt gcc ggt atg cag gtc ctc atg gat gct gag ctt gct    10854
Ser Gln Gly Ala Gly Met Gln Val Leu Met Asp Ala Glu Leu Ala
    3605            3610                3615 ctc gag atg ggt gct ccc atc ttt gcg gtg ctc gca ctc acg agc    10899
Leu Glu Met Gly Ala Pro Ile Phe Ala Val Leu Ala Leu Thr Ser
    3620            3625                3630 acg gcc acg gat aag caa ggc cgt tcg att ccg gcg ccg ggt cgc    10944
Thr Ala Thr Asp Lys Gln Gly Arg Ser Ile Pro Ala Pro Gly Arg
    3635            3640                3645 ggt att ctc acc tcg gcc cgc gag agc agc tct ggt gct gcg cct    10989
Gly Ile Leu Thr Ser Ala Arg Glu Ser Ser Ser Gly Ala Ala Pro
    3650            3655                3660 tcg ccg ctt ctt tcg ctg gag cgt cgc cgt gcg ggt ctc aag atg    11034
Ser Pro Leu Leu Ser Leu Glu Arg Arg Arg Ala Gly Leu Lys Met
    3665            3670                3675 gag ctc gag gcg ctc gag agc ctg aac aag caa aag tcg gac gcc    11079
Glu Leu Glu Ala Leu Glu Ser Leu Asn Lys Gln Lys Ser Asp Ala
    3680            3685                3690 gag ggc gag gat gcg gcc ttt ttc gag cgt ctt atc cag cgt cgc    11124
Glu Gly Glu Asp Ala Ala Phe Phe Glu Arg Leu Ile Gln Arg Arg
    3695            3700                3705 cgc gcc gct gcg ctc gag acc tgg ggc cag ggc ttt ttc aag aat    11169
Arg Ala Ala Ala Leu Glu Thr Trp Gly Gln Gly Phe Phe Lys Asn
    3710            3715                3720 gac ccg agc att gcg cct ctg cgt ggc gct ctg gct gtg tac ggc    11214
Asp Pro Ser Ile Ala Pro Leu Arg Gly Ala Leu Ala Val Tyr Gly
    3725            3730                3735
```

| | | | | | | | | | | | | | |
|---|---|---|---|---|---|---|---|---|---|---|---|---|---|
| ctt | ggc | gtc | gat | gac | ctc | ggt | gtg | gcc | agc | ttc | cac | ggc acc tcg | 11259 |
| Leu | Gly | Val | Asp | Asp | Leu | Gly | Val | Ala | Ser | Phe | His | Gly Thr Ser | |
| 3740 | | | | | 3745 | | | | | 3750 | | | |
| acc | aag | ctc | aat | gac | acg | aac | gaa | tct | ggc | gtg | ctc | aac aag cag | 11304 |
| Thr | Lys | Leu | Asn | Asp | Thr | Asn | Glu | Ser | Gly | Val | Leu | Asn Lys Gln | |
| 3755 | | | | | 3760 | | | | | 3765 | | | |
| atg | gag | cac | ctt | ggt | cgc | tcc | aag | ggt | aac | gtg | ctc | ttt gtt gtg | 11349 |
| Met | Glu | His | Leu | Gly | Arg | Ser | Lys | Gly | Asn | Val | Leu | Phe Val Val | |
| 3770 | | | | | 3775 | | | | | 3780 | | | |
| gcg | caa | aag | tac | ctg | acg | ggc | cac | ccc | aag | ggt | gcg | gcc tgc gcc | 11394 |
| Ala | Gln | Lys | Tyr | Leu | Thr | Gly | His | Pro | Lys | Gly | Ala | Ala Cys Ala | |
| 3785 | | | | | 3790 | | | | | 3795 | | | |
| tgg | atg | ttg | aac | ggc | ctg | atc | cag | tgc | atg | aac | gat | gct cgt gtg | 11439 |
| Trp | Met | Leu | Asn | Gly | Leu | Ile | Gln | Cys | Met | Asn | Asp | Ala Arg Val | |
| 3800 | | | | | 3805 | | | | | 3810 | | | |
| ccg | ggc | aac | cgc | aac | ctt | gac | aac | gtc | gat | gtc | aag | ttg cag aag | 11484 |
| Pro | Gly | Asn | Arg | Asn | Leu | Asp | Asn | Val | Asp | Val | Lys | Leu Gln Lys | |
| 3815 | | | | | 3820 | | | | | 3825 | | | |
| aac | tcg | tac | ctc | gtg | tac | ccg | aac | gag | ccc | gtg | gag | ctg ccc aag | 11529 |
| Asn | Ser | Tyr | Leu | Val | Tyr | Pro | Asn | Glu | Pro | Val | Glu | Leu Pro Lys | |
| 3830 | | | | | 3835 | | | | | 3840 | | | |
| atc | gag | gct | gcc | ctg | ctc | aag | agc | ttt | ggc | ttt | ggc | cag gcc ggt | 11574 |
| Ile | Glu | Ala | Ala | Leu | Leu | Lys | Ser | Phe | Gly | Phe | Gly | Gln Ala Gly | |
| 3845 | | | | | 3850 | | | | | 3855 | | | |
| gcc | gag | gtc | gtc | att | gtg | cac | ccg | gac | cgc | ctg | ctc | gcg acg ctc | 11619 |
| Ala | Glu | Val | Val | Ile | Val | His | Pro | Asp | Arg | Leu | Leu | Ala Thr Leu | |
| 3860 | | | | | 3865 | | | | | 3870 | | | |
| tcc | aag | gac | gtc | ttt | gac | aag | tac | gcc | gag | acg | cgc | agc ctg cgc | 11664 |
| Ser | Lys | Asp | Val | Phe | Asp | Lys | Tyr | Ala | Glu | Thr | Arg | Ser Leu Arg | |
| 3875 | | | | | 3880 | | | | | 3885 | | | |
| gag | cgc | cgt | acc | ttc | cgt | act | tcg | cag | aat | gtc | atg | act ggc gtg | 11709 |
| Glu | Arg | Arg | Thr | Phe | Arg | Thr | Ser | Gln | Asn | Val | Met | Thr Gly Val | |
| 3890 | | | | | 3895 | | | | | 3900 | | | |
| cgc | aag | tac | gtt | gtg | gtc | aag | gag | gct | cct | cct | tac | ccg gag gag | 11754 |
| Arg | Lys | Tyr | Val | Val | Val | Lys | Glu | Ala | Pro | Pro | Tyr | Pro Glu Glu | |
| 3905 | | | | | 3910 | | | | | 3915 | | | |
| ctc | gag | gag | gcc | gtg | tac | ctg | gat | cct | ctt | gcg | cgc | gcc acg tac | 11799 |
| Leu | Glu | Glu | Ala | Val | Tyr | Leu | Asp | Pro | Leu | Ala | Arg | Ala Thr Tyr | |
| 3920 | | | | | 3925 | | | | | 3930 | | | |
| agc | gct | gcc | tct | ggc | acc | tgg | gag | ttc | cgc | tcg | gcc | gcc ggc ctc | 11844 |
| Ser | Ala | Ala | Ser | Gly | Thr | Trp | Glu | Phe | Arg | Ser | Ala | Ala Gly Leu | |
| 3935 | | | | | 3940 | | | | | 3945 | | | |
| acg | tcg | agc | ggc | atg | ccg | cgt | atc | gcc | gcg | cag | gca | tct ggg gcc | 11889 |
| Thr | Ser | Ser | Gly | Met | Pro | Arg | Ile | Ala | Ala | Gln | Ala | Ser Gly Ala | |
| 3950 | | | | | 3955 | | | | | 3960 | | | |
| gcg | cag | gtg | ccc | gcg | ggc | ccc | acc | gag | acg | gtt | gcc | cct cag ggt | 11934 |
| Ala | Gln | Val | Pro | Ala | Gly | Pro | Thr | Glu | Thr | Val | Ala | Pro Gln Gly | |
| 3965 | | | | | 3970 | | | | | 3975 | | | |
| ctt | cag | gtt | tcg | gcc | aag | gac | cgt | ctc | cgc | atg | acg | ctg cag gag | 11979 |
| Leu | Gln | Val | Ser | Ala | Lys | Asp | Arg | Leu | Arg | Met | Thr | Leu Gln Glu | |
| 3980 | | | | | 3985 | | | | | 3990 | | | |
| cag | gcg | gag | ggc | atg | tcg | tcc | aac | ttt | ggt | gga | tcc | ggt gtt ggc | 12024 |
| Gln | Ala | Glu | Gly | Met | Ser | Ser | Asn | Phe | Gly | Gly | Ser | Gly Val Gly | |
| 3995 | | | | | 4000 | | | | | 4005 | | | |
| gtc | ggt | gtt | gat | gtc | gag | aac | gtc | agc | acc | ttt | gcc | gac ttt gcc | 12069 |
| Val | Gly | Val | Asp | Val | Glu | Asn | Val | Ser | Thr | Phe | Ala | Asp Phe Ala | |
| 4010 | | | | | 4015 | | | | | 4020 | | | |
| ggc | tcg | aag | cag | gac | ttt | atc | gcg | cgc | aac | ttt | acc | gag cgc gag | 12114 |
| Gly | Ser | Lys | Gln | Asp | Phe | Ile | Ala | Arg | Asn | Phe | Thr | Glu Arg Glu | |
| 4025 | | | | | 4030 | | | | | 4035 | | | |

-continued

```
att gcg tac tgc cgc gcg gct gcg gat cct gcg gcc tcg ttt gcg      12159
Ile Ala Tyr Cys Arg Ala Ala Ala Asp Pro Ala Ala Ser Phe Ala
    4040             4045             4050 ggc cgc tgg gct gcc aag gag gcg ctc gtc aag gct ctc tcg agc      12204
Gly Arg Trp Ala Ala Lys Glu Ala Leu Val Lys Ala Leu Ser Ser
4055             4060             4065 ctc gca ccg gag cag cgc ccg ctc tgg tcg ggt cac gct cct          12249
Leu Ala Pro Glu Gln Arg Pro Leu Trp Ser Gly Gly His Ala Pro
    4070             4075             4080 ctt gtg gac atc gag atc gtc ccg aac cct tcg ggc gca ccg gtg      12294
Leu Val Asp Ile Glu Ile Val Pro Asn Pro Ser Gly Ala Pro Val
    4085             4090             4095 gtc cag ctc cac ggt cac ccg cag cag gtg tcc gag atg ctc gct      12339
Val Gln Leu His Gly His Pro Gln Gln Val Ser Glu Met Leu Ala
    4100             4105             4110 gtc aac acc ctc tcg gtt tcc atc tcg cac acg gct gac gtt gcc      12384
Val Asn Thr Leu Ser Val Ser Ile Ser His Thr Ala Asp Val Ala
    4115             4120             4125 gtc gcc aac gcc gtt gtg cgc aag taa                              12411
Val Ala Asn Ala Val Val Arg Lys
    4130             4135
```

<210> SEQ ID NO 2
<211> LENGTH: 4136
<212> TYPE: PRT
<213> ORGANISM: Schizochytrium sp.

<400> SEQUENCE: 2

```
Met Ala Gln Pro Glu Ser Thr Thr Pro Thr Met Thr Pro Glu Glu Gly
1               5                   10                  15

Gln Met Glu Gly Ala Pro Gln Gln Asp Asn Ala Gln Val Lys Lys His
            20                  25                  30

Cys Phe Ala Asp Ala Asp Val Ala Thr Cys Ile Ala Ala Phe Gly Gly
        35                  40                  45

Gln Gly Ser Asp Trp Leu Ser Glu Leu Arg Ser Leu Gln Glu Lys Gly
    50                  55                  60

Gln Thr Asn Val Arg Glu Thr Ile Glu Leu Ala Leu Asp Lys Leu Glu
65                  70                  75                  80

Asp Leu Val Lys Ala Glu Pro Trp Tyr Glu Glu His Gly Gly Cys Asp
                85                  90                  95

Ile Arg Ala Trp Leu Glu Ser Asp Asp Asn Val Pro Asn Phe Asp Leu
            100                 105                 110

Leu Arg Tyr Ala Pro Val Ser Phe Pro Leu Ile Phe Leu Thr Gln Met
        115                 120                 125

Cys Asn Tyr Met Arg Val Leu Glu Lys Leu Gly Thr Cys His Glu Asp
    130                 135                 140

Ala Leu Gln Lys Gly Trp Val Lys Ala Ser Leu Gly His Ser Gln Gly
145                 150                 155                 160

Val Val Ser Ala Ala Val Ala Ala Ala Asn Thr Asp Arg Glu Leu
                165                 170                 175

Arg Asn Leu Val Val Ser Gly Leu Glu Tyr Met Ser Lys Val Gly Ile
            180                 185                 190

Ala Ala Gln Arg Thr Leu Asp Tyr Glu Leu Gly Arg Arg Asn Ala Gly
        195                 200                 205

Pro Glu Thr Pro Met Leu Ala Val Gln Gly Met Asp Glu Lys Val Leu
    210                 215                 220
```

-continued

```
Thr Lys Ala Phe Lys Ala Val Ser Leu Ser Asn Glu Lys Gln Ala
225                 230                 235                 240

Met Met Ala Lys Ile Ser Pro Thr Ala Ala Ala Thr Ala Ala Pro
                245                 250                 255

Ala Ala Val Ser Asp Glu Asp Arg Phe Ser Ile Ala Leu Arg Asn Gly
            260                 265                 270

His Asp Asp Phe Val Val Cys Gly Glu Pro Lys Asp Leu Arg Val Leu
        275                 280                 285

Arg Lys Val Ile Glu Lys Gln Ser Ala Glu Pro Gly Lys Glu Ala Gln
    290                 295                 300

Ala Arg Thr Pro Phe Ser Lys Arg Lys Pro Val Thr Gln Thr Thr Phe
305                 310                 315                 320

Leu Arg Met Thr Ala Val Phe His Ser Ala Leu Asn Lys Asp Ala Leu
                325                 330                 335

Ala Gln Ile Asn Thr Trp Ala Pro Glu Ser Ala Phe Ser Lys Ala Phe
            340                 345                 350

Ala Gln Ala Ser Leu Arg Val Pro Val Phe Asp Thr Lys Ser Gly Ala
        355                 360                 365

Asn Leu Gln Asp Val Pro Ala Ala Asp Val Val Ala His Leu Thr Thr
    370                 375                 380

Asn Met Leu Thr Glu Arg Ala Asp Val Leu Val Ser Leu Arg Ala Ala
385                 390                 395                 400

Glu Thr Lys Thr Asp Ala Ser His Leu Leu Cys Phe Gly Pro Gly Arg
                405                 410                 415

Val Ala Gly His Leu Met Ala His Ala Leu Val Gly Thr Gly Ile Gln
            420                 425                 430

Val Val Gln Ala Ala Asp Pro Asp Thr Pro Asn Asp Ser Lys Arg Ser
        435                 440                 445

Ser Ala Val Ser Ile Gly Ser Val Ile Glu Ala Gln Ser Pro Glu Ala
450                 455                 460

Val Pro Thr Ala Pro Glu Trp Ala Lys Lys Phe Ala Pro Arg Ile Ala
465                 470                 475                 480

Val Arg Ala Gly Asp Gly Glu Arg Val Leu Met Thr Lys Phe Thr Ser
                485                 490                 495

Thr Leu Gly Arg Ala Pro Val Leu Met Ser Gly Met Thr Pro Thr Thr
            500                 505                 510

Ser Phe His Gly Val Asp Leu Val Ala Ala Ser Asn Ala Gly Phe
        515                 520                 525

Asn Ala Glu Leu Ala Ala Gly Gly Leu Pro Thr Pro Asp Ile Phe Lys
    530                 535                 540

Ser Lys Val Leu Glu Leu Ala Ser Lys Leu Asn Pro Gly Val Gly Ile
545                 550                 555                 560

Ser Ile Asn Met Leu Tyr Leu Asn Ala Tyr Gln Trp Gly Phe Gln Phe
                565                 570                 575

Pro Leu Val Val Glu Leu Ala Lys Gln Gly Val Pro Ile Glu Ser Ile
            580                 585                 590

Thr Ile Gly Ala Gly Val Pro Ser Glu Asp Lys Ala Gly Asp Ile Phe
        595                 600                 605

Asp Gly Leu Gln Ser Ala Gly Ile Asn Leu Ile Ala Phe Lys Pro Gly
    610                 615                 620

Ser Lys Gln Ala Ile Lys Asp Val Cys Ala Leu Ala Ala Leu Arg Pro
625                 630                 635                 640

Ser Met Asn Val Met Leu Gln Trp Thr Ser Gly Arg Gly Gly Gly His
```

-continued

```
                645                 650                 655
His Ser Phe Glu Asp Phe His Glu Pro Leu Leu Ser Thr Tyr Glu Glu
            660                 665                 670

Ile Arg Ser His Asp Asn Ile Val Leu Val Ile Gly Ser Gly Phe Gly
            675                 680                 685

Asp Ala Gln Ser Val Leu Thr Tyr Leu Asp Gly Ser Trp Ser Gln Asn
            690                 695                 700

Glu Ile Phe Gly Arg Leu Ala Lys Met Pro Val Asp Gly Val Leu Phe
705                 710                 715                 720

Gly Ser Arg Cys Met Val Ala Leu Glu Ala Thr Ala Pro Glu Val
            725                 730                 735

Lys Gln Leu Ile Val Asp Ala Glu Gly Leu Glu Asp Glu Leu Ser Trp
            740                 745                 750

Glu Lys Ser Tyr Glu Glu Val Ala Gly Gly Val Val Thr Val Lys Ser
            755                 760                 765

Glu Leu Gly Glu Pro Ile His Lys Ile Ala Thr Arg Gly Ile Leu Leu
            770                 775                 780

Trp Arg Glu Phe Asp Lys Arg Phe Phe Asp Gln Pro Arg Gly Glu Lys
785                 790                 795                 800

Arg Arg Asn Ala Ile Met Ser Ala Lys Asp Glu Ile Ile Ala Arg Leu
            805                 810                 815

Asn Ala Asp Phe Gln Lys Pro Tyr Phe Gly Arg Lys Ser Asp Gly Ser
            820                 825                 830

Thr Cys Asp Val Glu Glu Met Thr Tyr Ala Glu Val Leu Glu Arg Met
            835                 840                 845

Val Glu Leu Met His Val Lys Asn Gly Gly Asp Lys Ala Gly Arg Leu
            850                 855                 860

Ala Pro Thr Arg Trp Ile Asp Pro Thr Phe Cys Ser Arg Val Leu Leu
865                 870                 875                 880

Met Met Gln Arg Ala Ala Ala Arg Phe Ala Pro Lys Gly Lys Lys Thr
            885                 890                 895

Ala Val Val Val Pro Asp Asn Lys Leu Leu Lys Glu Asp Pro Asp Ala
            900                 905                 910

Ala Ile Ala Lys Phe Leu Asp Ala Ile Pro Ala Leu Arg Glu Ser Leu
            915                 920                 925

Met Ala Asp Asp Asp Val Thr Tyr Phe Leu Asp Leu Cys Lys Val Pro
            930                 935                 940

Thr Arg Gly Lys Pro Val Asn Phe Ile Pro Val Val Asp Glu Asp Leu
945                 950                 955                 960

Gly Phe Trp Leu Lys Lys Asp Ser Leu Trp Tyr Ser Glu Gln Leu Asp
            965                 970                 975

Ala Val Pro Gly Arg Asp Pro Gly Arg Val Cys Ile Leu His Gly Pro
            980                 985                 990

Val Ala Ala Arg Phe Ser Thr Lys  Val Asp Glu Pro Ile  Ala Asp Ile
            995                1000                1005

Leu Gly Gly Ile His Ala Asp  Ile Val Lys Ser Ile  Lys Cys Asp
            1010               1015                1020

Glu Ile  Lys Val Ser Val Leu  Ser Pro Gln Ser Leu  His Asp Ala
            1025               1030                1035

Ser Val  Leu Arg Ile Ile Ser  Glu Thr Pro Phe Leu  Val Arg Gly
            1040               1045                1050

Lys Ser  Phe Val Pro Asn Pro  Ile Gly Arg Val Val  Lys Arg Glu
            1055               1060                1065
```

-continued

```
Gly Phe Glu His Ser Ser Phe Gly Glu Asp Gly Ile Thr Val Gln
    1070                1075                1080

Asp Pro Glu Arg Gly Leu Thr Val Ala Thr Val Ser Gln Val Gly
    1085                1090                1095

Ser Ser Gly Thr Glu Ile Glu Phe Lys Val Phe Asp Lys Glu Ala
    1100                1105                1110

Gly Ala Val Leu Lys Gln Thr Phe Thr Val Asp Leu Thr Ser Pro
    1115                1120                1125

Arg Pro Leu Phe Gln Thr Glu Glu Asn Asn Leu Ala Ala Thr Lys
    1130                1135                1140

Gln Leu Tyr Arg Ala Ala Trp Asp Cys Gln Asp Glu Tyr His Ala
    1145                1150                1155

Gly Asp Thr Phe Thr Asp Glu Ile Thr Val Thr Ala Asp Asn Ile
    1160                1165                1170

Glu Ala Phe Asn Leu Gly Thr Ser Asp Glu Tyr Ser Gly Ser Ala
    1175                1180                1185

Glu Ala Pro Thr Asp Ile Ser Ile Met Ala Gly Trp Arg Pro Leu
    1190                1195                1200

Ala Arg Ala Leu Phe Val Glu Glu Leu Lys Ser Asn Leu Leu Lys
    1205                1210                1215

Leu Val His Leu Thr Asn Gly Ile Arg Leu Pro Asn Pro Ala Thr
    1220                1225                1230

Arg Thr Pro Val Lys Ala Gly Glu Val Ile Arg Ser Glu Ala Arg
    1235                1240                1245

Ile Thr Gly Ile Thr Ile Gln Pro Lys Val Gly Lys Lys Val Gln
    1250                1255                1260

Val Lys Gly Arg Ile Thr Arg Ala Lys Asp Ser Thr Ser Glu Pro
    1265                1270                1275

Gln Met Trp Val Glu Met Asn Ser Glu Phe Leu Ile Arg Gly Ile
    1280                1285                1290

Asn Glu Thr Pro Glu Glu Tyr Ala Thr Thr Phe Glu Glu Thr Pro
    1295                1300                1305

Ala Glu Arg His Ile Ile Glu Val Lys Asp Glu Thr Val Ala Glu
    1310                1315                1320

Leu Leu Met Ser Arg Ala Trp Ile Lys Leu Glu Ser Gly Val Lys
    1325                1330                1335

Ile His Glu Gly Asp Arg Val Thr Ile Asp Leu Gly Thr Ile Ser
    1340                1345                1350

Asn Arg Phe Ala Gly Pro Gly Arg Leu Val Asp Ile Lys Ala Ser
    1355                1360                1365

Gly Asn Val Phe Ile Glu Thr Thr Ala Lys Ser Pro Arg Gln Phe
    1370                1375                1380

Pro Ala Ser Pro Ser His Ser Ala Gly Ser Val Pro Ser Asp Asp
    1385                1390                1395

Phe Ile Asn Val Asp Ser Ser Gly Thr Ser Lys Val Gly Val
    1400                1405                1410

Val Asp Phe Ala Thr Ser Asp Gly Gln Glu Phe Gln Val Asn Pro
    1415                1420                1425

Val Leu Ser Phe Leu Glu Lys Tyr Ser Glu Ala Lys Asn Leu Gly
    1430                1435                1440

His Val Ala Glu Asn Gly Gly Tyr Glu Leu Phe Asp Glu Pro Ala
    1445                1450                1455
```

-continued

Val Val Lys Ala Pro Ala Asp Cys Thr Thr Tyr Ala Arg Gly Ser
1460             1465                 1470

Arg Asp Ala Asn Pro Ile His Arg Glu Glu Ala Phe Ala Val Leu
1475             1480                 1485

Ala Asp Leu Pro Asp Gly Lys Pro Ile Val His Gly Met Trp Thr
1490             1495                 1500

Ala Cys Met Ala Arg Ala Arg Leu Glu Glu Ile Ala Ala Lys Gly
1505             1510                 1515

Asp Leu Lys Arg Ile Val Ser Tyr Glu Ala Ser Phe Val Asp Met
1520             1525                 1530

Val His Cys Ser Asp Glu Leu Val Val Thr Ala Lys Gln Thr Gly
1535             1540                 1545

Val Lys Asn Gly Leu Met Leu Val Thr Val Ser Val Asn Arg Thr
1550             1555                 1560

Ser Asp Arg Ala Leu Val Met Thr Ala Arg Ala Glu Leu Glu Gln
1565             1570                 1575

Pro Ser Thr Ala Tyr Leu Phe Thr Gly Gln Gly Ser Ala Ser Lys
1580             1585                 1590

Gly Met Gly Met Asp Arg Tyr Ala Ala Ser Ala Thr Val Arg Asn
1595             1600                 1605

Val Trp Asp Arg Ala Glu Asp Tyr Leu Arg Ala Arg Phe Gly Phe
1610             1615                 1620

Ser Ile Leu Gln Ile Val Arg Glu Asn Pro Lys Ser Phe Thr Val
1625             1630                 1635

His Phe Gly Gly Pro Arg Gly Lys Ala Ile Arg Glu Asn Leu Arg
1640             1645                 1650

Asn Leu Thr Ala Gln Asp Pro Ser Thr Gly Gln Asn Val Pro Leu
1655             1660                 1665

Leu Pro Glu Ile Ser Ala Thr Thr Lys Ser Phe Thr Phe Asn Ser
1670             1675                 1680

Pro Thr Gly Leu Leu Phe Ala Thr Gln Phe Ser Gln Pro Ala Leu
1685             1690                 1695

Val Leu Val Gln Lys Ala Ala Phe Glu Glu Leu Arg Glu Ala Gly
1700             1705                 1710

Leu Val Pro Glu Lys Ala Leu Phe Ala Gly His Ser Leu Gly Glu
1715             1720                 1725

Tyr Ala Ala Leu Ala Gly Tyr Ala Asp Ser Leu Thr Ile Glu Asp
1730             1735                 1740

Leu Val Glu Thr Val Phe Leu Arg Gly Met Val Met Gln Asn Ala
1745             1750                 1755

Val Pro Arg Asp Ser Glu Gly Arg Ser Asn Tyr Ala Met Val Ala
1760             1765                 1770

Ala Asn Pro Leu Arg Val Gly Arg Gly Phe Thr Pro Glu Met Leu
1775             1780                 1785

Ser Glu Ile Val Asp Leu Ile Thr Glu Asn Glu Glu Met Gly Lys
1790             1795                 1800

Pro Leu Leu Gln Ile Val Asn Phe Asn Val Arg Phe Thr Gln Tyr
1805             1810                 1815

Val Val Ala Gly Glu Leu Leu Ala Leu Asp Ala Leu Ala Glu Ala
1820             1825                 1830

Leu Asn Leu Ala Phe Ala Lys Gly Val Arg Asp Val Ala Ala Leu
1835             1840                 1845

Ala Glu His Gly Ala Lys Thr Ala Gln Ala Ser Leu Ala Lys Arg

-continued

```
             1850                1855                1860

Asn Gly Arg Ala Glu Pro Leu Lys Arg Gly Lys Ala  Thr Ile Pro
     1865                1870                1875

Leu Pro Gly Ile Asp Val Pro Phe His Ser Arg Lys  Leu Leu Pro
     1880                1885                1890

Gly Val Gly Ala Phe Arg Lys Leu Leu Ala Pro Arg  Phe Ser Leu
     1895                1900                1905

Gln Thr Met Glu Lys Ile Ile Asp Arg Leu Val Gly  Asn Tyr Ile
     1910                1915                1920

Pro Asn Val Thr Ala Glu Val Leu Ser Leu Asp Arg  Ala Tyr Ala
     1925                1930                1935

Glu Lys Val Gln Lys Val Thr Gly Ser Gln Pro Met  Ala Glu Leu
     1940                1945                1950

Leu Glu Asp Phe Asp Thr Ala Thr Asp Ala Glu Lys  Val Arg Thr
     1955                1960                1965

Leu Val Ile Glu Leu Leu Ala His Gln Phe Ala Met  Pro Val Arg
     1970                1975                1980

Trp Ile Glu Thr Gln Asp Leu Met Phe Gly Ser His  Val Glu Arg
     1985                1990                1995

Val Ile Glu Met Gly Pro Ser Ala Thr Leu Thr Ala  Met Ala Lys
     2000                2005                2010

Gln Thr Val Lys Ser Gly Ala Tyr Gly Asp Ala Glu  Glu Tyr Ser
     2015                2020                2025

Pro Glu Ile Met Trp Trp Lys Gln Asp Arg Asp Ser  Val Tyr Tyr
     2030                2035                2040

Glu Val Glu Asn Val Gly Pro Ser Phe Gly Asp Tyr  Met Asp Glu
     2045                2050                2055

Arg Ala Ala Leu Glu Glu Glu Leu Ala Ala Ala Lys  Ala Ala Lys
     2060                2065                2070

Ala Glu Pro Lys Ala Glu Ala Ala Ser Lys Ala Glu  Ala Ala Pro
     2075                2080                2085

Ala Pro Lys Ala Ala Ala Pro Ala Pro Lys Ala Ala  Ala Pro Ala
     2090                2095                2100

Pro Ala Ala Pro Ala Pro Ala Pro Ala Ala Pro Ala  Pro Ala Pro
     2105                2110                2115

Ala Ala Gly Gly Ser Val Ala Asp Ala Pro Pro Asp  Ala Lys His
     2120                2125                2130

Val Leu Arg Ala Leu Leu Ala Ala Lys Leu Lys Lys  Ser Met Gly
     2135                2140                2145

Asp Val Pro Ala Ser Thr Thr Val Gln Ala Leu Ser  Ala Gly Arg
     2150                2155                2160

Ser Ala Val Gln Asn Glu Val Met Gly Glu Leu Ser  Ala Glu Phe
     2165                2170                2175

Lys Gly Ala Ile Pro Asp Asn Ala Gly Glu Met Pro  Leu Ala Glu
     2180                2185                2190

Leu Gly Gly Asn Leu Ser Ser Tyr Lys Asp Pro Gly  Pro Val Thr
     2195                2200                2205

Gln Lys Leu Val Ala Arg Thr Leu Ser Ala Ala Leu  Pro Gly Gly
     2210                2215                2220

Phe Gly Ala Asn Ala Ala Lys Asp Tyr Leu Gly Gln  His Trp Gly
     2225                2230                2235

Leu Gly Ala Gly Arg Thr Phe Ser Val Leu Leu His  Ala Thr Thr
     2240                2245                2250
```

-continued

```
Met Ala Pro Glu Lys Arg Leu Lys Ser Glu Glu Gly Lys Gln
    2255                2260                2265

Trp Leu Asp Asp Val Cys Lys Ser Tyr Gly Gln Asp Ala Gly Val
    2270                2275                2280

Ser Leu Ser Pro Gly Gly Gly Ser Ala Gly Ala Ala Ala Ala Ala
    2285                2290                2295

Pro Met Met Met Met Gln Gln Ser Gly Pro Ala Ala Ala Pro Pro
    2300                2305                2310

Pro Asp Ala Pro Val Ser Ala Leu His Ala Met Arg Val Met Leu
    2315                2320                2325

Ala Ala Lys Phe Glu Lys Gly Phe Ala Asp Val Ala Asp Ser Ala
    2330                2335                2340

Thr Val Ala Ala Leu Ser Asn Gly Lys Ser Ala Val Gln Asn Glu
    2345                2350                2355

Val Ala Gly Asp Phe Gly Ala Glu Phe Gly Glu Val Glu Glu Ala
    2360                2365                2370

Ala Gln Thr Pro Leu Ser Glu Leu Ala Gly Lys Val Gln Gly Ser
    2375                2380                2385

Tyr Asn Gly Pro Gly Lys Val Leu Thr Arg Asp Val Asn Lys Leu
    2390                2395                2400

Leu Gly Gln Cys Leu Pro Gly Gly Phe Gly Ala Ser Ala Ala Arg
    2405                2410                2415

Ser Tyr Leu Ser Gly Asp Arg Met Leu Pro Ala Gly Arg Val Glu
    2420                2425                2430

Ser Val Leu Ile His Gly Leu Cys Met Ala Pro Lys Gly Arg Leu
    2435                2440                2445

Gly Ser Pro Glu Asp Ala Lys Ala Trp Leu Asp Ser Leu Cys Ser
    2450                2455                2460

Ala Tyr Gly Ser Phe Ala Gly Ile Thr Ile Pro Thr Pro Gly Ser
    2465                2470                2475

Gly Gly Gly Gly Ala Ala Met Gly Phe Ala Gly Gly Pro Gln Val
    2480                2485                2490

Ser Ser Ala Glu Leu Ser Ala Leu Lys Ser Asp Val Gln Ala Met
    2495                2500                2505

Val Glu Ser Gln Leu Asp Ala Leu Arg Arg Phe Leu Asp Ile Asp
    2510                2515                2520

Pro Leu His Ala Asp Lys Leu Leu Glu Leu Glu Lys Gln Val Arg
    2525                2530                2535

Ala Glu Thr Glu Ser Lys Leu Asp Ser Ile His Ala Glu Met Thr
    2540                2545                2550

Val Asp Phe Cys Glu Arg Val Gln Pro Gln Phe Asp Glu Asn Arg
    2555                2560                2565

Val Arg Val Tyr Asp Ser Phe Trp Asn Trp Val Val Gln Asp Ala
    2570                2575                2580

Met Gln Met His Leu His Val Leu Gly Arg Leu Glu Ala Ala Arg
    2585                2590                2595

Gln Gly Lys Glu Val Asn Ala Ser Ala Asp Ser Asn Pro His Phe
    2600                2605                2610

Asp Glu Met Ser Lys Trp Leu Leu Gly Ser Ser Ser Asp Ala
    2615                2620                2625

Pro Pro Ile Ala Trp Phe Arg Asn Phe Leu Cys Asn Arg Ala Thr
    2630                2635                2640
```

-continued

| | | | | | | | | | | | |
|---|---|---|---|---|---|---|---|---|---|---|---|
|Pro|Gln|Leu|Leu|Gln|Ala|Val|Lys|Phe|Phe|Ala|Asn|Ser|Met|His|
| |2645| | | |2650| | | |2655| | | | | |

Asp Ala Gly Tyr Val Asp Tyr Ala Gln Ala Ile Ser Leu Leu Ala
    2660            2665            2670

Glu Gln Val Lys Asn Trp Leu Asn Asn Val Pro Val His Val Ala
    2675            2680            2685

Asn Phe Glu Pro Lys Ala Pro Gln Val Arg Val Leu Asp Asp Gly
    2690            2695            2700

Val Val Asp Tyr Phe Glu Ile Asp Arg Asp Gly Val Asn Asp Ala
    2705            2710            2715

Ala Arg Tyr Val Ala Glu Met Ser Arg Gly Leu Tyr Tyr Lys Arg
    2720            2725            2730

Thr Gly Pro Ser Arg Val Glu Asn Pro Ser Gln Thr Val Asn Val
    2735            2740            2745

Ala Gly Asp Gly Arg Leu Thr Leu Leu Glu Leu Pro Pro Ser Gln
    2750            2755            2760

Ser Glu Ile Glu Ala Val Ala Gly Ala Gly Trp Arg Leu Pro Arg
    2765            2770            2775

Ser Glu Ala Glu Leu Ala Arg Glu Leu Thr Gly Glu Pro Leu Ser
    2780            2785            2790

Leu Asp Thr Ser Glu Thr Ser Ser Glu Glu Gly Asp Leu Pro Asp
    2795            2800            2805

Gly Pro Thr Leu Asp Arg Leu Arg Ala Ser Val Asn Arg Gly Val
    2810            2815            2820

Gly Gly Asp Glu Ala Glu Gly Gly Glu Gly Lys Ile Ser Thr Ala
    2825            2830            2835

Ser Leu Lys Asn Gly Tyr Glu Ser Ile His Val Ser Lys Gln Val
    2840            2845            2850

Pro Tyr Val His Leu Lys Ser Leu Ser Gly Val Asp Lys Ser Val
    2855            2860            2865

Arg Ile Leu Asn Glu Gln Leu Thr Ser Glu Tyr Phe Ser Cys Met
    2870            2875            2880

Asp Glu Ile Ala Thr Ser Gly Val Ser Phe Ala Gly Gln Val Ala
    2885            2890            2895

Leu Val Thr Gly Ala Gly Ser Gly Ser Ile Gly Ala Glu Leu Val
    2900            2905            2910

Lys Ser Leu Leu Glu Gly Gly Ala Thr Val Leu Ala Ala Ile Arg
    2915            2920            2925

Thr Ala Arg Ser Glu Ala Ala Leu Thr Lys Glu Tyr Ala Arg Phe
    2930            2935            2940

Gln Ser Ile Tyr Lys Glu Phe Gly Ala Lys Asp Ser Lys Leu Tyr
    2945            2950            2955

Leu Val Pro Cys Asn Cys Ala Ser Gln Gln Asp Met Lys Ser Leu
    2960            2965            2970

Val Ser Tyr Thr Tyr Asp Lys Leu Gly Leu Asp Val Asp Phe Val
    2975            2980            2985

Val Pro Phe Ala Ala Ala Ala Gln Gln Gly Lys Asp Ile Ser Ser
    2990            2995            3000

Ile Asp Ala Ser Ser Glu Val Ser His Arg Met Met Thr Asn
    3005            3010            3015

Val Val Arg Leu Leu Gly Ala Leu Lys Asp Ala Lys Thr Ser Arg
    3020            3025            3030

Asp Ile Thr Thr Arg Pro Ala Met Val Leu Ile Pro Cys Ser Pro

-continued

```
        3035                3040                3045
Asn His Gly Glu Phe Gly Gln Asp Gly Leu Tyr Ala Glu Ser Lys
        3050                3055                3060
Leu Gly Cys Glu Ala Leu Leu Asn Lys Trp Ser Ser Glu Gly Trp
        3065                3070                3075
Gly Asp Tyr Leu Ser Leu Ala Ala Cys Val Ile Gly Trp Thr Arg
        3080                3085                3090
Ser Ala Leu Met Gln His Asn Asn Ile Val Ala Pro Gly Ile Glu
        3095                3100                3105
Lys Leu Gly Cys Arg Thr Phe Ala Pro Glu Glu Thr Asn Phe Asn
        3110                3115                3120
Leu Val Gly Leu Leu His Pro Arg Met Val Thr Leu Ala Ala Glu
        3125                3130                3135
Glu Pro Leu Trp Ala Asp Leu Thr Gly Cys Trp Thr Val Ile Pro
        3140                3145                3150
Asn Met Lys Asp Ala Ala Asp Ser Leu Arg Ser Gly Leu Met Ser
        3155                3160                3165
Lys Ser Arg Val Ala Arg Ala Ile Ala Ala Ser Asn Gln Leu Glu
        3170                3175                3180
Glu Ala Lys Ser Ala Asp Val Ser His Val Leu Pro Pro Pro Glu
        3185                3190                3195
Ser Ser Gly Pro Leu Ala Ser Thr Gln Leu Gly Met Thr Pro Phe
        3200                3205                3210
Pro Ala Leu Pro Ser Glu Glu Ala Arg Lys Ser Leu Ser Ala Leu
        3215                3220                3225
Glu Gly Met Val Asp Leu Arg Lys Val Val Val Val Gly Tyr
        3230                3235                3240
Gly Glu Val Gly Pro Trp Gly Asn Ala Arg Thr Arg Trp Glu Met
        3245                3250                3255
Glu Ser Tyr Gly Glu Phe Ser Leu Glu Gly Ser Ile Glu Leu Ala
        3260                3265                3270
Trp Met Val Gly Leu Ile Lys His His Asp Gly Pro Leu Pro Ser
        3275                3280                3285
Gly Pro Pro Arg Ser Lys Tyr Thr Gly Trp Val Asp Ala Ala Ser
        3290                3295                3300
Gly Glu Pro Val Ala Asp Asn Glu Ile Lys Arg Arg Tyr Glu Glu
        3305                3310                3315
His Met Leu Lys Ser Cys Gly Ile Arg Ile Val Glu Pro Glu Leu
        3320                3325                3330
Phe Glu Gly Tyr Asn Pro Glu Ala Lys Arg Phe Leu His Ser Val
        3335                3340                3345
Val Leu Asp Arg Asp Met Pro Pro Val Glu Leu Ser Gly Leu Glu
        3350                3355                3360
Glu Gly Leu Gln Tyr Arg Asn Glu Leu Gly Ala Asp Cys Cys Asp
        3365                3370                3375
Val Trp Gln Lys Pro Ser Asp Gly Gln Trp Met Met Arg Val Lys
        3380                3385                3390
Lys Gly Ala Glu Val Ser Ile Ala Lys Ala Leu Lys Phe Asn Arg
        3395                3400                3405
Asn Ile Ala Gly Gln Ile Pro Thr Gly Trp Asp Ala Arg Arg Phe
        3410                3415                3420
Gly Leu Pro Glu Asp Ile Ala Thr Gly Val Asp Pro Val Thr Leu
        3425                3430                3435
```

```
Tyr Thr Leu Val Ser Thr Val Glu Ala Leu Met Ala Ala Gly Leu
    3440            3445                3450

Ser Asp Pro Tyr Glu Leu Tyr Gln Tyr Val His Val Ser Glu Val
    3455            3460                3465

Gly Asn Thr Ser Gly Gly Gly Met Gly Gly Met Arg Ser Leu Lys
    3470            3475                3480

Arg Leu Phe His Gln Arg Ala Leu Asp Glu Asp Ile Pro Ser Asp
    3485            3490                3495

Thr Leu Ala Glu Ser Phe Ile Asn Thr Met Pro Ala Trp Val Asn
    3500            3505                3510

Met Leu Leu Met Ser Ser Ser Gly Pro Ile Lys Thr Pro Val Gly
    3515            3520                3525

Ala Cys Ala Thr Ala Ala Glu Ser Leu Asp Ile Gly Met Glu Thr
    3530            3535                3540

Ile Leu Ser Gly Lys Ala Arg Val Val Ile Ala Gly Gly Tyr Asp
    3545            3550                3555

Asp Phe Gly Glu Glu Gly Ser Tyr Glu Phe Ala Gln Met Gly Ala
    3560            3565                3570

Thr Asn Asn Thr Asp Leu Asp Ser Gly Arg Gly Arg Thr Val Arg
    3575            3580                3585

Glu Ser Ser Arg Pro Met Ser Ser Ser Arg Ala Gly Phe Val Glu
    3590            3595                3600

Ser Gln Gly Ala Gly Met Gln Val Leu Met Asp Ala Glu Leu Ala
    3605            3610                3615

Leu Glu Met Gly Ala Pro Ile Phe Ala Val Leu Ala Leu Thr Ser
    3620            3625                3630

Thr Ala Thr Asp Lys Gln Gly Arg Ser Ile Pro Ala Pro Gly Arg
    3635            3640                3645

Gly Ile Leu Thr Ser Ala Arg Glu Ser Ser Ser Gly Ala Ala Pro
    3650            3655                3660

Ser Pro Leu Leu Ser Leu Glu Arg Arg Arg Ala Gly Leu Lys Met
    3665            3670                3675

Glu Leu Glu Ala Leu Glu Ser Leu Asn Lys Gln Lys Ser Asp Ala
    3680            3685                3690

Glu Gly Glu Asp Ala Ala Phe Phe Glu Arg Leu Ile Gln Arg Arg
    3695            3700                3705

Arg Ala Ala Ala Leu Glu Thr Trp Gly Gln Gly Phe Phe Lys Asn
    3710            3715                3720

Asp Pro Ser Ile Ala Pro Leu Arg Gly Ala Leu Ala Val Tyr Gly
    3725            3730                3735

Leu Gly Val Asp Asp Leu Gly Val Ala Ser Phe His Gly Thr Ser
    3740            3745                3750

Thr Lys Leu Asn Asp Thr Asn Glu Ser Gly Val Leu Asn Lys Gln
    3755            3760                3765

Met Glu His Leu Gly Arg Ser Lys Gly Asn Val Leu Phe Val Val
    3770            3775                3780

Ala Gln Lys Tyr Leu Thr Gly His Pro Lys Gly Ala Ala Cys Ala
    3785            3790                3795

Trp Met Leu Asn Gly Leu Ile Gln Cys Met Asn Asp Ala Arg Val
    3800            3805                3810

Pro Gly Asn Arg Asn Leu Asp Asn Val Asp Val Lys Leu Gln Lys
    3815            3820                3825
```

| | | | | | | | | | | |
|---|---|---|---|---|---|---|---|---|---|---|
| Asn | Ser | Tyr | Leu | Val | Tyr | Pro | Asn | Glu | Pro | Val | Glu | Leu | Pro | Lys |
| | 3830 | | | | 3835 | | | | 3840 | |

Ile Glu Ala Ala Leu Leu Lys Ser Phe Gly Phe Gly Gln Ala Gly
    3845                    3850                  3855

Ala Glu Val Val Ile Val His Pro Asp Arg Leu Leu Ala Thr Leu
    3860                    3865                  3870

Ser Lys Asp Val Phe Asp Lys Tyr Ala Glu Thr Arg Ser Leu Arg
    3875                    3880                  3885

Glu Arg Arg Thr Phe Arg Thr Ser Gln Asn Val Met Thr Gly Val
    3890                    3895                  3900

Arg Lys Tyr Val Val Val Lys Glu Ala Pro Pro Tyr Pro Glu Glu
    3905                    3910                  3915

Leu Glu Glu Ala Val Tyr Leu Asp Pro Leu Ala Arg Ala Thr Tyr
    3920                    3925                  3930

Ser Ala Ala Ser Gly Thr Trp Glu Phe Arg Ser Ala Ala Gly Leu
    3935                    3940                  3945

Thr Ser Ser Gly Met Pro Arg Ile Ala Ala Gln Ala Ser Gly Ala
    3950                    3955                  3960

Ala Gln Val Pro Ala Gly Pro Thr Glu Thr Val Ala Pro Gln Gly
    3965                    3970                  3975

Leu Gln Val Ser Ala Lys Asp Arg Leu Arg Met Thr Leu Gln Glu
    3980                    3985                  3990

Gln Ala Glu Gly Met Ser Ser Asn Phe Gly Gly Ser Gly Val Gly
    3995                    4000                  4005

Val Gly Val Asp Val Glu Asn Val Ser Thr Phe Ala Asp Phe Ala
    4010                    4015                  4020

Gly Ser Lys Gln Asp Phe Ile Ala Arg Asn Phe Thr Glu Arg Glu
    4025                    4030                  4035

Ile Ala Tyr Cys Arg Ala Ala Ala Asp Pro Ala Ala Ser Phe Ala
    4040                    4045                  4050

Gly Arg Trp Ala Ala Lys Glu Ala Leu Val Lys Ala Leu Ser Ser
    4055                    4060                  4065

Leu Ala Pro Glu Gln Arg Pro Leu Trp Ser Gly Gly His Ala Pro
    4070                    4075                  4080

Leu Val Asp Ile Glu Ile Val Pro Asn Pro Ser Gly Ala Pro Val
    4085                    4090                  4095

Val Gln Leu His Gly His Pro Gln Gln Val Ser Glu Met Leu Ala
    4100                    4105                  4110

Val Asn Thr Leu Ser Val Ser Ile Ser His Thr Ala Asp Val Ala
    4115                    4120                  4125

Val Ala Asn Ala Val Val Arg Lys
    4130                    4135

<210> SEQ ID NO 3
<211> LENGTH: 990
<212> TYPE: DNA
<213> ORGANISM: Schizochytrium sp.

<400> SEQUENCE: 3

```
taagtaagaa caagtgcatg catacatacg caaatcttgc ttttatctcg atcgcgatcg      60
atcgatcgac cgagaagata taaatcagtc gatcaatcta aaattaatgt tcatgtttg     120
attgaaagaa gtttgtctaa gctcttgaga tacggtatac tcactcactg gtcggaggag    180
cgcgtgtggg gaaggcggag aaatgatgat gatgaagacg gtcttggctt ctgtggcagc    240
```

```
cgatgtcttg tcgatccacc cccccaaaaa caagaaagac caagacctca tgtgcatctt     300
tgtttcctct tttgtcggaa ctcactcgct ggtcggaata gcgcgtgtag ggaaggcggg     360
aaaatgtcaa agacggtctt ggcctctgtg cagccgatg tcttgtcgat caaacataaa     420
aagaaagagg gactaaaacc tcatgtgcat cttcgtttcc tcttttgttg atgtcgatcc     480
atgtcaggtg cgtgcatctt tgtttcctct ttcgttgatc catatcaggt gcgtgcattt     540
tgattccact ttctgtcgat ccatatcagg tgggtgcatt ttgattcctc tttctgtcga     600
tccacacgtg catgttagtt tccttatctc tccatttccc tcctgtccat ccactacctc     660
actgtatact cttcaccaag gatatcctcg actgtccaat ccgcgtcccc caatatcctc     720
gtctccgtcc ctgcctccca gcatatcctc tctaacccat tctatcctgg ccgcggtcg      780 tccagccagc cgccgctccg cgtcccttgc ccgcggcgaa gcggcgcatc cgcgcgggcg     840
gaacagtggg ttatgccggt ataacccact tgcgcgcggc gcgggaacag cggctcggaa     900
gcgtctgcaa gtgcggaaag gaaggagag gagaggggag gagagggagg agaggagaga     960
aaagcaagaa ggaaggaagg aaggaaggga                                      990

<210> SEQ ID NO 4
<211> LENGTH: 729
<212> TYPE: DNA
<213> ORGANISM: Schizochytrium sp.

<400> SEQUENCE: 4
cgggcgggag ggacacagcc aggcagtcag tcagtcagcc gcacagagag agcgcgcctg      60
cgagtcccgt ctggtctcgg aattgtatcc cgcgcagagc tcagaatcgc aggtcgatcg     120
atcgagcgat ggatccatcg ctctatccgt ccatcgatcc atcgcatcca tcgcatccat     180
cgcatccatc gttgcatcgc ttgcaccgcc cgcttgcatc gcgtgcgtgc gcaggcgggc     240
ggcggccacg acgcgaccga gagcggcgg gagtgcagac gccgccggcg cccgcggctg     300
cgtcgccgca ggaagaagga ggggggcgcg tgtttcccgc gggagggagg agggagggag     360
ggaggtggtt gggccaaaaa gggcggcctg gacaggcagg caggccggaa gcgacgccag     420
cgagcgaagg aagaggagag agccgcgcgg gcggccagcg cggggcgggc ggcagcaaac     480
ccgctactca gggtaaaaga cagacagctc ttcgagcgag cttgttcact tcgcggaagc     540
acgcgcgcag gcacgcaggc acgcaggcag catagcgagc agcagcagca tcgcgagcag     600
cattgcgaga ggaggcgctg accgccggcc tcgagcaaca aaagaagcag cagcagcagc     660
agcacgagca gcagcagcag cagcacgagc agcagcagca cgagcagcag cagcagcagc     720
agcaagatg                                                             729

<210> SEQ ID NO 5
<211> LENGTH: 371
<212> TYPE: PRT
<213> ORGANISM: Schizochytrium sp.

<400> SEQUENCE: 5

Ala Phe Gly Gly Gln Gly Ser Asp Trp Leu Ser Glu Leu Arg Ser Leu
1               5                   10                  15

Gln Glu Lys Gly Gln Thr Asn Val Arg Glu Thr Ile Glu Leu Ala Leu
            20                  25                  30

Asp Lys Leu Glu Asp Leu Val Lys Ala Glu Pro Trp Tyr Glu Glu His
        35                  40                  45

Gly Gly Cys Asp Ile Arg Ala Trp Leu Glu Ser Asp Asp Asn Val Pro
    50                  55                  60
```

```
Asn Phe Asp Leu Leu Arg Tyr Ala Pro Val Ser Phe Pro Leu Ile Phe
 65                  70                  75                  80

Leu Thr Gln Met Cys Asn Tyr Met Arg Val Leu Glu Lys Leu Gly Thr
             85                  90                  95

Cys His Glu Asp Ala Leu Gln Lys Gly Trp Val Lys Ala Ser Leu Gly
            100                 105                 110

His Ser Gln Gly Val Val Ser Ala Ala Val Ala Ala Ala Asn Thr
        115                 120                 125

Asp Arg Glu Leu Arg Asn Leu Val Val Ser Gly Leu Glu Tyr Met Ser
    130                 135                 140

Lys Val Gly Ile Ala Ala Gln Arg Thr Leu Asp Tyr Glu Leu Gly Arg
145                 150                 155                 160

Arg Asn Ala Gly Pro Glu Thr Pro Met Leu Ala Val Gln Gly Met Asp
                165                 170                 175

Glu Lys Val Leu Thr Lys Ala Phe Lys Ala Val Ser Leu Ser Asn
            180                 185                 190

Glu Lys Gln Ala Met Met Ala Lys Ile Ser Pro Thr Ala Ala Ala Ala
        195                 200                 205

Thr Ala Ala Pro Ala Ala Val Ser Asp Glu Asp Arg Phe Ser Ile Ala
210                 215                 220

Leu Arg Asn Gly His Asp Asp Phe Val Val Cys Gly Glu Pro Lys Asp
225                 230                 235                 240

Leu Arg Val Leu Arg Lys Val Ile Glu Lys Gln Ser Ala Glu Pro Gly
                245                 250                 255

Lys Glu Ala Gln Ala Arg Thr Pro Phe Ser Lys Arg Lys Pro Val Thr
            260                 265                 270

Gln Thr Thr Phe Leu Arg Met Thr Ala Val Phe His Ser Ala Leu Asn
        275                 280                 285

Lys Asp Ala Leu Ala Gln Ile Asn Thr Trp Ala Pro Glu Ser Ala Phe
290                 295                 300

Ser Lys Ala Phe Ala Gln Ala Ser Leu Arg Val Pro Val Phe Asp Thr
305                 310                 315                 320

Lys Ser Gly Ala Asn Leu Gln Asp Val Pro Ala Ala Asp Val Val Ala
                325                 330                 335

His Leu Thr Thr Asn Met Leu Thr Glu Arg Ala Asp Val Leu Val Ser
            340                 345                 350

Leu Arg Ala Ala Glu Thr Lys Thr Asp Ala Ser His Leu Leu Cys Phe
        355                 360                 365

Gly Pro Gly
    370

<210> SEQ ID NO 6
<211> LENGTH: 751
<212> TYPE: PRT
<213> ORGANISM: Schizochytrium sp.

<400> SEQUENCE: 6

Gln Ser Pro Glu Ala Val Pro Thr Ala Pro Glu Trp Ala Lys Lys Phe
1               5                   10                  15

Ala Pro Arg Ile Ala Val Arg Ala Gly Asp Gly Glu Arg Val Leu Met
            20                  25                  30

Thr Lys Phe Thr Ser Thr Leu Gly Arg Ala Pro Val Leu Met Ser Gly
        35                  40                  45

Met Thr Pro Thr Thr Ser Phe His Gly Val Asp Leu Val Ala Ala Ala
```

-continued

```
                50                  55                  60
Ser Asn Ala Gly Phe Asn Ala Glu Leu Ala Ala Gly Gly Leu Pro Thr
 65                  70                  75                  80

Pro Asp Ile Phe Lys Ser Lys Val Leu Glu Leu Ala Ser Lys Leu Asn
                 85                  90                  95

Pro Gly Val Gly Ile Ser Ile Asn Met Leu Tyr Leu Asn Ala Tyr Gln
            100                 105                 110

Trp Gly Phe Gln Phe Pro Leu Val Val Glu Leu Ala Lys Gln Gly Val
            115                 120                 125

Pro Ile Glu Ser Ile Thr Ile Gly Ala Gly Val Pro Ser Glu Asp Lys
        130                 135                 140

Ala Gly Asp Ile Phe Asp Gly Leu Gln Ser Ala Gly Ile Asn Leu Ile
145                 150                 155                 160

Ala Phe Lys Pro Gly Ser Lys Gln Ala Ile Lys Asp Val Cys Ala Leu
                165                 170                 175

Ala Ala Leu Arg Pro Ser Met Asn Val Met Leu Gln Trp Thr Ser Gly
            180                 185                 190

Arg Gly Gly Gly His His Ser Phe Glu Asp Phe His Glu Pro Leu Leu
            195                 200                 205

Ser Thr Tyr Glu Glu Ile Arg Ser His Asp Asn Ile Val Leu Val Ile
        210                 215                 220

Gly Ser Gly Phe Gly Asp Ala Gln Ser Val Leu Thr Tyr Leu Asp Gly
225                 230                 235                 240

Ser Trp Ser Gln Asn Glu Ile Phe Gly Arg Leu Ala Lys Met Pro Val
                245                 250                 255

Asp Gly Val Leu Phe Gly Ser Arg Cys Met Val Ala Leu Glu Ala Ala
            260                 265                 270

Thr Ala Pro Glu Val Lys Gln Leu Ile Val Asp Ala Glu Gly Leu Glu
        275                 280                 285

Asp Glu Leu Ser Trp Glu Lys Ser Tyr Glu Glu Val Ala Gly Gly Val
        290                 295                 300

Val Thr Val Lys Ser Glu Leu Gly Glu Pro Ile His Lys Ile Ala Thr
305                 310                 315                 320

Arg Gly Ile Leu Leu Trp Arg Glu Phe Asp Lys Arg Phe Phe Asp Gln
                325                 330                 335

Pro Arg Gly Glu Lys Arg Arg Asn Ala Ile Met Ser Ala Lys Asp Glu
            340                 345                 350

Ile Ile Ala Arg Leu Asn Ala Asp Phe Gln Lys Pro Tyr Phe Gly Arg
        355                 360                 365

Lys Ser Asp Gly Ser Thr Cys Asp Val Glu Glu Met Thr Tyr Ala Glu
        370                 375                 380

Val Leu Glu Arg Met Val Glu Leu Met His Val Lys Asn Gly Gly Asp
385                 390                 395                 400

Lys Ala Gly Arg Leu Ala Pro Thr Arg Trp Ile Asp Pro Thr Phe Cys
                405                 410                 415

Ser Arg Val Leu Leu Met Met Gln Arg Ala Ala Ala Arg Phe Ala Pro
            420                 425                 430

Lys Gly Lys Lys Thr Ala Val Val Pro Asp Asn Lys Leu Leu Lys
        435                 440                 445

Glu Asp Pro Asp Ala Ala Ile Ala Lys Phe Leu Asp Ala Ile Pro Ala
        450                 455                 460

Leu Arg Glu Ser Leu Met Ala Asp Asp Val Thr Tyr Phe Leu Asp
465                 470                 475                 480
```

```
Leu Cys Lys Val Pro Thr Arg Gly Lys Pro Val Asn Phe Ile Pro Val
                485                 490                 495
Val Asp Glu Asp Leu Gly Phe Trp Leu Lys Lys Asp Ser Leu Trp Tyr
            500                 505                 510
Ser Glu Gln Leu Asp Ala Val Pro Gly Arg Asp Pro Gly Arg Val Cys
            515                 520                 525
Ile Leu His Gly Pro Val Ala Ala Arg Phe Ser Thr Lys Val Asp Glu
            530                 535                 540
Pro Ile Ala Asp Ile Leu Gly Gly Ile His Ala Asp Ile Val Lys Ser
545                 550                 555                 560
Ile Lys Cys Asp Glu Ile Lys Val Ser Val Leu Ser Pro Gln Ser Leu
                565                 570                 575
His Asp Ala Ser Val Leu Arg Ile Ile Ser Glu Thr Pro Phe Leu Val
            580                 585                 590
Arg Gly Lys Ser Phe Val Pro Asn Pro Ile Gly Arg Val Val Lys Arg
            595                 600                 605
Glu Gly Phe Glu His Ser Ser Phe Gly Glu Asp Gly Ile Thr Val Gln
    610                 615                 620
Asp Pro Glu Arg Gly Leu Thr Val Ala Thr Val Ser Gln Val Gly Ser
625                 630                 635                 640
Ser Gly Thr Glu Ile Glu Phe Lys Val Phe Asp Lys Glu Ala Gly Ala
                645                 650                 655
Val Leu Lys Gln Thr Phe Thr Val Asp Leu Thr Ser Pro Arg Pro Leu
            660                 665                 670
Phe Gln Thr Glu Glu Asn Asn Leu Ala Ala Thr Lys Gln Leu Tyr Arg
            675                 680                 685
Ala Ala Trp Asp Cys Gln Asp Glu Tyr His Ala Gly Asp Thr Phe Thr
            690                 695                 700
Asp Glu Ile Thr Val Thr Ala Asp Asn Ile Glu Ala Phe Asn Leu Gly
705                 710                 715                 720
Thr Ser Asp Glu Tyr Ser Gly Ser Ala Glu Ala Pro Thr Asp Ile Ser
                725                 730                 735
Ile Met Ala Gly Trp Arg Pro Leu Ala Arg Ala Leu Phe Val Glu
            740                 745                 750

<210> SEQ ID NO 7
<211> LENGTH: 126
<212> TYPE: PRT
<213> ORGANISM: Schizochytrium sp.

<400> SEQUENCE: 7

Gly Tyr Glu Leu Phe Asp Glu Pro Ala Val Val Lys Ala Pro Ala Asp
1               5                   10                  15
Cys Thr Thr Tyr Ala Arg Gly Ser Arg Asp Ala Asn Pro Ile His Arg
            20                  25                  30
Glu Glu Ala Phe Ala Val Leu Ala Asp Leu Pro Asp Gly Lys Pro Ile
        35                  40                  45
Val His Gly Met Trp Thr Ala Cys Met Ala Arg Ala Arg Leu Glu Glu
    50                  55                  60
Ile Ala Ala Lys Gly Asp Leu Lys Arg Ile Val Ser Tyr Glu Ala Ser
65                  70                  75                  80
Phe Val Asp Met Val His Cys Ser Asp Glu Leu Val Val Thr Ala Lys
                85                  90                  95
Gln Thr Gly Val Lys Asn Gly Leu Met Leu Val Thr Val Ser Val Asn
```

```
                    100                 105                 110
Arg Thr Ser Asp Arg Ala Leu Val Met Thr Ala Arg Ala Glu
            115                 120                 125

<210> SEQ ID NO 8
<211> LENGTH: 451
<212> TYPE: PRT
<213> ORGANISM: Schizochytrium sp.

<400> SEQUENCE: 8

Glu Leu Glu Gln Pro Ser Thr Ala Tyr Leu Phe Thr Gly Gln Gly Ser
1               5                   10                  15

Ala Ser Lys Gly Met Gly Met Asp Arg Tyr Ala Ala Ser Ala Thr Val
            20                  25                  30

Arg Asn Val Trp Asp Arg Ala Glu Asp Tyr Leu Arg Ala Arg Phe Gly
        35                  40                  45

Phe Ser Ile Leu Gln Ile Val Arg Glu Asn Pro Lys Ser Phe Thr Val
    50                  55                  60

His Phe Gly Gly Pro Arg Gly Lys Ala Ile Arg Glu Asn Leu Arg Asn
65                  70                  75                  80

Leu Thr Ala Gln Asp Pro Ser Thr Gly Gln Asn Val Pro Leu Leu Pro
                85                  90                  95

Glu Ile Ser Ala Thr Thr Lys Ser Phe Thr Phe Asn Ser Pro Thr Gly
            100                 105                 110

Leu Leu Phe Ala Thr Gln Phe Ser Gln Pro Ala Leu Val Leu Val Gln
        115                 120                 125

Lys Ala Ala Phe Glu Glu Leu Arg Glu Ala Gly Leu Val Pro Glu Lys
    130                 135                 140

Ala Leu Phe Ala Gly His Ser Leu Gly Glu Tyr Ala Ala Leu Ala Gly
145                 150                 155                 160

Tyr Ala Asp Ser Leu Thr Ile Glu Asp Leu Val Glu Thr Val Phe Leu
                165                 170                 175

Arg Gly Met Val Met Gln Asn Ala Val Pro Arg Asp Ser Glu Gly Arg
            180                 185                 190

Ser Asn Tyr Ala Met Val Ala Ala Asn Pro Leu Arg Val Gly Arg Gly
        195                 200                 205

Phe Thr Pro Glu Met Leu Ser Glu Ile Val Asp Leu Ile Thr Glu Asn
    210                 215                 220

Glu Glu Met Gly Lys Pro Leu Leu Gln Ile Val Asn Phe Asn Val Arg
225                 230                 235                 240

Phe Thr Gln Tyr Val Val Ala Gly Glu Leu Leu Ala Leu Asp Ala Leu
                245                 250                 255

Ala Glu Ala Leu Asn Leu Ala Phe Ala Lys Gly Val Arg Asp Val Ala
            260                 265                 270

Ala Leu Ala Glu His Gly Ala Lys Thr Ala Gln Ala Ser Leu Ala Lys
        275                 280                 285

Arg Asn Gly Arg Ala Glu Pro Leu Lys Arg Gly Lys Ala Thr Ile Pro
    290                 295                 300

Leu Pro Gly Ile Asp Val Pro Phe His Ser Arg Lys Leu Leu Pro Gly
305                 310                 315                 320

Val Gly Ala Phe Arg Lys Leu Leu Ala Pro Arg Phe Ser Leu Gln Thr
                325                 330                 335

Met Glu Lys Ile Ile Asp Arg Leu Val Gly Asn Tyr Ile Pro Asn Val
            340                 345                 350
```

```
Thr Ala Glu Val Leu Ser Leu Asp Arg Ala Tyr Ala Glu Lys Val Gln
            355                 360                 365

Lys Val Thr Gly Ser Gln Pro Met Ala Glu Leu Leu Glu Asp Phe Asp
        370                 375                 380

Thr Ala Thr Asp Ala Glu Lys Val Arg Thr Leu Val Ile Glu Leu Leu
385                 390                 395                 400

Ala His Gln Phe Ala Met Pro Val Arg Trp Ile Glu Thr Gln Asp Leu
                405                 410                 415

Met Phe Gly Ser His Val Glu Arg Val Ile Glu Met Gly Pro Ser Ala
                420                 425                 430

Thr Leu Thr Ala Met Ala Lys Gln Thr Val Lys Ser Gly Ala Tyr Gly
            435                 440                 445

Asp Ala Glu
    450

<210> SEQ ID NO 9
<211> LENGTH: 151
<212> TYPE: PRT
<213> ORGANISM: Schizochytrium sp.

<400> SEQUENCE: 9

Ala Ala Lys Leu Lys Lys Ser Met Gly Asp Val Pro Ala Ser Thr Thr
1               5                   10                  15

Val Gln Ala Leu Ser Ala Gly Arg Ser Ala Val Gln Asn Glu Val Met
            20                  25                  30

Gly Glu Leu Ser Ala Glu Phe Lys Gly Ala Ile Pro Asp Asn Ala Gly
        35                  40                  45

Glu Met Pro Leu Ala Glu Leu Gly Gly Asn Leu Ser Ser Tyr Lys Asp
    50                  55                  60

Pro Gly Pro Val Thr Gln Lys Leu Val Ala Arg Thr Leu Ser Ala Ala
65                  70                  75                  80

Leu Pro Gly Gly Phe Gly Ala Asn Ala Ala Lys Asp Tyr Leu Gly Gln
                85                  90                  95

His Trp Gly Leu Gly Ala Gly Arg Thr Phe Ser Val Leu Leu His Ala
            100                 105                 110

Thr Thr Met Ala Pro Glu Lys Arg Leu Lys Ser Glu Glu Glu Gly Lys
        115                 120                 125

Gln Trp Leu Asp Asp Val Cys Lys Ser Tyr Gly Gln Asp Ala Gly Val
    130                 135                 140

Ser Leu Ser Pro Gly Gly Gly
145                 150

<210> SEQ ID NO 10
<211> LENGTH: 261
<212> TYPE: PRT
<213> ORGANISM: Schizochytrium sp.

<400> SEQUENCE: 10

Arg Val Met Leu Ala Ala Lys Phe Glu Lys Gly Phe Ala Asp Val Ala
1               5                   10                  15

Asp Ser Ala Thr Val Ala Ala Leu Ser Asn Gly Lys Ser Ala Val Gln
            20                  25                  30

Asn Glu Val Ala Gly Asp Phe Gly Ala Glu Phe Gly Val Glu Glu
        35                  40                  45

Ala Ala Gln Thr Pro Leu Ser Glu Leu Ala Gly Lys Val Gln Gly Ser
    50                  55                  60
```

```
Tyr Asn Gly Pro Gly Lys Val Leu Thr Arg Asp Val Asn Lys Leu Leu
 65                  70                  75                  80

Gly Gln Cys Leu Pro Gly Gly Phe Gly Ala Ser Ala Ala Arg Ser Tyr
                 85                  90                  95

Leu Ser Gly Asp Arg Met Leu Pro Ala Gly Arg Val Glu Ser Val Leu
            100                 105                 110

Ile His Gly Leu Cys Met Ala Pro Lys Gly Arg Leu Gly Ser Pro Glu
        115                 120                 125

Asp Ala Lys Ala Trp Leu Asp Ser Leu Cys Ser Ala Tyr Gly Ser Phe
130                 135                 140

Ala Gly Ile Thr Ile Pro Thr Pro Gly Ser Gly Gly Gly Ala Ala
145                 150                 155                 160

Met Gly Phe Ala Gly Gly Pro Gln Val Ser Ser Ala Glu Leu Ser Ala
                165                 170                 175

Leu Lys Ser Asp Val Gln Ala Met Val Glu Ser Gln Leu Asp Ala Leu
            180                 185                 190

Arg Arg Phe Leu Asp Ile Asp Pro Leu His Ala Asp Lys Leu Leu Glu
        195                 200                 205

Leu Glu Lys Gln Val Arg Ala Glu Thr Glu Ser Lys Leu Asp Ser Ile
210                 215                 220

His Ala Glu Met Thr Val Asp Phe Cys Glu Arg Val Gln Pro Gln Phe
225                 230                 235                 240

Asp Glu Asn Arg Val Arg Val Tyr Asp Ser Phe Trp Asn Trp Val Val
                245                 250                 255

Gln Asp Ala Met Gln
            260

<210> SEQ ID NO 11
<211> LENGTH: 201
<212> TYPE: PRT
<213> ORGANISM: Schizochytrium sp.

<400> SEQUENCE: 11

Val Thr Gly Ala Gly Ser Gly Ser Ile Gly Ala Glu Leu Val Lys Ser
  1               5                  10                  15

Leu Leu Glu Gly Gly Ala Thr Val Leu Ala Ala Ile Arg Thr Ala Arg
                 20                  25                  30

Ser Glu Ala Ala Leu Thr Lys Glu Tyr Ala Arg Phe Gln Ser Ile Tyr
             35                  40                  45

Lys Glu Phe Gly Ala Lys Asp Ser Lys Leu Tyr Leu Val Pro Cys Asn
 50                  55                  60

Cys Ala Ser Gln Gln Asp Met Lys Ser Leu Val Ser Tyr Thr Tyr Asp
 65                  70                  75                  80

Lys Leu Gly Leu Asp Val Asp Phe Val Val Pro Phe Ala Ala Ala Ala
                 85                  90                  95

Gln Gln Gly Lys Asp Ile Ser Ser Ile Asp Ala Ser Ser Glu Val Ser
            100                 105                 110

His Arg Met Met Met Thr Asn Val Val Arg Leu Leu Gly Ala Leu Lys
        115                 120                 125

Asp Ala Lys Thr Ser Arg Asp Ile Thr Thr Arg Pro Ala Met Val Leu
130                 135                 140

Ile Pro Cys Ser Pro Asn His Gly Glu Phe Gly Gln Asp Gly Leu Tyr
145                 150                 155                 160

Ala Glu Ser Lys Leu Gly Cys Glu Ala Leu Leu Asn Lys Trp Ser Ser
                165                 170                 175
```

Glu Gly Trp Gly Asp Tyr Leu Ser Leu Ala Ala Cys Val Ile Gly Trp
            180                 185                 190

Thr Arg Ser Ala Leu Met Gln His Asn
            195                 200

<210> SEQ ID NO 12
<211> LENGTH: 526
<212> TYPE: PRT
<213> ORGANISM: Schizochytrium sp.

<400> SEQUENCE: 12

Leu Asp Arg Asp Met Pro Val Glu Leu Ser Gly Leu Glu Glu Gly
1               5                   10                  15

Leu Gln Tyr Arg Asn Glu Leu Gly Ala Asp Cys Cys Asp Val Trp Gln
            20                  25                  30

Lys Pro Ser Asp Gly Gln Trp Met Met Arg Val Lys Lys Gly Ala Glu
            35                  40                  45

Val Ser Ile Ala Lys Ala Leu Lys Phe Asn Arg Asn Ile Ala Gly Gln
        50                  55                  60

Ile Pro Thr Gly Trp Asp Ala Arg Arg Phe Gly Leu Pro Glu Asp Ile
65                  70                  75                  80

Ala Thr Gly Val Asp Pro Val Thr Leu Tyr Thr Leu Val Ser Thr Val
            85                  90                  95

Glu Ala Leu Met Ala Ala Gly Leu Ser Asp Pro Tyr Glu Leu Tyr Gln
            100                 105                 110

Tyr Val His Val Ser Glu Val Gly Asn Thr Ser Gly Gly Met Gly
            115                 120                 125

Gly Met Arg Ser Leu Lys Arg Leu Phe His Gln Arg Ala Leu Asp Glu
        130                 135                 140

Asp Ile Pro Ser Asp Thr Leu Ala Glu Ser Phe Ile Asn Thr Met Pro
145                 150                 155                 160

Ala Trp Val Asn Met Leu Leu Met Ser Ser Gly Pro Ile Lys Thr
            165                 170                 175

Pro Val Gly Ala Cys Ala Thr Ala Ala Glu Ser Leu Asp Ile Gly Met
            180                 185                 190

Glu Thr Ile Leu Ser Gly Lys Ala Arg Val Val Ile Ala Gly Gly Tyr
            195                 200                 205

Asp Asp Phe Gly Glu Glu Gly Ser Tyr Glu Phe Ala Gln Met Gly Ala
        210                 215                 220

Thr Asn Asn Thr Asp Leu Asp Ser Gly Arg Gly Arg Thr Val Arg Glu
225                 230                 235                 240

Ser Ser Arg Pro Met Ser Ser Arg Ala Gly Phe Val Glu Ser Gln
            245                 250                 255

Gly Ala Gly Met Gln Val Leu Met Asp Ala Glu Leu Ala Leu Glu Met
            260                 265                 270

Gly Ala Pro Ile Phe Ala Val Leu Ala Leu Thr Ser Thr Ala Thr Asp
        275                 280                 285

Lys Gln Gly Arg Ser Ile Pro Ala Pro Gly Arg Gly Ile Leu Thr Ser
        290                 295                 300

Ala Arg Glu Ser Ser Ser Gly Ala Ala Pro Ser Pro Leu Leu Ser Leu
305                 310                 315                 320

Glu Arg Arg Arg Ala Gly Leu Lys Met Glu Leu Glu Ala Leu Glu Ser
            325                 330                 335

Leu Asn Lys Gln Lys Ser Asp Ala Glu Gly Glu Asp Ala Ala Phe Phe

-continued

```
                340                 345                 350
Glu Arg Leu Ile Gln Arg Arg Ala Ala Leu Glu Thr Trp Gly
        355                 360                 365

Gln Gly Phe Phe Lys Asn Asp Pro Ser Ile Ala Pro Leu Arg Gly Ala
        370                 375                 380

Leu Ala Val Tyr Gly Leu Gly Val Asp Asp Leu Gly Val Ala Ser Phe
385                 390                 395                 400

His Gly Thr Ser Thr Lys Leu Asn Asp Thr Asn Glu Ser Gly Val Leu
                405                 410                 415

Asn Lys Gln Met Glu His Leu Gly Arg Ser Lys Gly Asn Val Leu Phe
                420                 425                 430

Val Val Ala Gln Lys Tyr Leu Thr Gly His Pro Lys Gly Ala Ala Cys
                435                 440                 445

Ala Trp Met Leu Asn Gly Leu Ile Gln Cys Met Asn Asp Ala Arg Val
                450                 455                 460

Pro Gly Asn Arg Asn Leu Asp Asn Val Asp Val Lys Leu Gln Lys Asn
465                 470                 475                 480

Ser Tyr Leu Val Tyr Pro Asn Glu Pro Val Glu Leu Pro Lys Ile Glu
                485                 490                 495

Ala Ala Leu Leu Lys Ser Phe Gly Phe Gly Gln Ala Gly Ala Glu Val
                500                 505                 510

Val Ile Val His Pro Asp Arg Leu Leu Ala Thr Leu Ser Lys
                515                 520                 525

<210> SEQ ID NO 13
<211> LENGTH: 112
<212> TYPE: PRT
<213> ORGANISM: Schizochytrium sp.

<400> SEQUENCE: 13

Ser Lys Gln Asp Phe Ile Ala Arg Asn Phe Thr Glu Arg Glu Ile Ala
1               5                   10                  15

Tyr Cys Arg Ala Ala Asp Pro Ala Ala Ser Phe Ala Gly Arg Trp
                20                  25                  30

Ala Ala Lys Glu Ala Leu Val Lys Ala Leu Ser Ser Leu Ala Pro Glu
                35                  40                  45

Gln Arg Pro Leu Trp Ser Gly His Ala Pro Leu Val Asp Ile Glu
        50                  55                  60

Ile Val Pro Asn Pro Ser Gly Ala Pro Val Val Gln Leu His Gly His
65                  70                  75                  80

Pro Gln Gln Val Ser Glu Met Leu Ala Val Asn Thr Leu Ser Val Ser
                85                  90                  95

Ile Ser His Thr Ala Asp Val Ala Val Ala Asn Ala Val Val Arg Lys
                100                 105                 110
```

SCHIZOCHYTRIUM FATTY ACID SYNTHASE (FAS) AND PRODUCTS AND METHODS RELATED THERETO

CROSS-REFERENCE TO RELATED APPLICATIONS

This application claims priority under 35 U.S.C. § 119(e) from U.S. Provisional Application Ser. No. 60/544,692, filed Feb. 13, 2004. The entire disclosure of U.S. Provisional Application Ser. No. 60/544,692 is incorporated herein by reference.

FIELD OF THE INVENTION

This invention generally relates to a fatty acid synthase (FAS) from *Schizochytrium* and to products and methods related thereto.

BACKGROUND OF THE INVENTION

The de novo synthesis of short and medium chain saturated fatty acids from acetyl-CoA and malonyl-CoA is a complex process catalyzed by several enzyme activities. In most bacteria and in plants these activities are associated with discrete monofunctional polypeptides. In fungi and animals however, these activities are integrated into one or two multifunctional polypeptide chains. Fatty acids, in particular in the form of oils and fats, which are glycerol esters, play a major role in human nutrition because of their high energy content. Additionally, specific types of fatty acids (e.g., polyunsaturated fatty acids such as DHA) have a wide range of physiological effects. There is great interest in being able to manipulate specific types of fatty acids made in organisms that produce these fatty acids (e.g., in the form of oils and/or phospholipids).

SUMMARY OF THE INVENTION

One embodiment of the present invention relates to an isolated protein comprising an amino acid sequence selected from: (a) an amino acid sequence selected from the group consisting of: SEQ ID NO:2, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, an amino acid sequence consisting of positions 1-500 of SEQ ID NO:2, an amino acid sequence consisting of positions 450-1300 of SEQ ID NO:2, an amino acid sequence consisting of positions 1250-1700 of SEQ ID NO:2, an amino acid sequence consisting of positions 1575-2100 of SEQ ID NO:2, an amino acid sequence consisting of positions 2025-2850 of SEQ ID NO:2, an amino acid sequence consisting of positions 2800-3350 of SEQ ID NO:2, an amino acid sequence consisting of positions 3300-3900 of SEQ ID NO:2, an amino acid sequence consisting of positions 3900-4136 of SEQ ID NO:2, and a biologically active fragment thereof, and (b) an amino acid sequence that is at least about 45% identical to any of the amino acid sequences of (a) and having the biological activity of the amino acid sequence of (a). In other aspects of this embodiment, the isolated protein comprises an amino acid sequence that is at least about 60% identical, at least about 80% identical, or at least about 95% identical to any of the amino acid sequences of (a). In a preferred aspect of this embodiment, the protein comprises an amino acid sequence selected from: an amino acid sequence selected from the group consisting of: SEQ ID NO:2, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, an amino acid sequence consisting of positions 1-500 of SEQ ID NO:2, an amino acid sequence consisting of positions 450-1300 of SEQ ID NO:2, an amino acid sequence consisting of positions 1250-1700 of SEQ ID NO:2, an amino acid sequence consisting of positions 1575-2100 of SEQ ID NO:2, an amino acid sequence consisting of positions 2025-2850 of SEQ ID NO:2, an amino acid sequence consisting of positions 2800-3350 of SEQ ID NO:2, an amino acid sequence consisting of positions 3300-3900 of SEQ ID NO:2, an amino acid sequence consisting of positions 3900-4136 of SEQ ID NO:2, or biologically active fragments of any of these sequences. In an even more preferred embodiment, the protein comprises an amino acid sequence selected from: SEQ ID NO:2, SEQ ID NO:5, SEQ ID NO:6, SEQ ID NO:7, SEQ ID NO:8, SEQ ID NO:9, SEQ ID NO:10, SEQ ID NO:11, SEQ ID NO:12, and SEQ I NO:13.

In one aspect of this embodiment, the protein comprises any two or more amino acid sequences selected from the group consisting of: SEQ ID NO:2, SEQ ID NO:5, SEQ ID NO:6, SEQ ID NO:7, SEQ ID NO:8, SEQ ID NO:9, SEQ ID NO:10, SEQ ID NO:11, SEQ if NO:12, and SEQ ID NO:13. In another aspect, the protein comprises SEQ ID NO:5, SEQ ID NO:6, SEQ ID NO:7, SEQ ID NO:8, SEQ ID NO:9, SEQ ED NO:10, SEQ ID NO:11, SEQ ID NO:12, and SEQ ID NO:13. In yet another aspect, the isolated protein is from a Thraustochytriales microorganism and in a preferred embodiment, from a *Schizochytrium* microorganism.

Yet another embodiment of the present invention relates to an isolated nucleic acid molecule comprising a nucleic acid sequence encoding any of the above-identified proteins, or a nucleic acid sequence that is fully complementary thereto. Another embodiment of the present invention relates to a recombinant nucleic acid molecule comprising such an isolated nucleic acid molecule, operatively linked to a transcription control sequence. In one aspect, the transcription control sequence is a tissue-specific transcription control sequence. In another aspect, the recombinant nucleic acid molecule further comprises a targeting sequence. Yet another embodiment of the present invention relates to a recombinant cell that has been transformed with such a recombinant nucleic acid molecule.

Another embodiment of the present invention relates to a genetically modified microorganism for producing short chain fatty acids by a biosynthetic process, the microorganism being transformed with a recombinant nucleic acid molecule as described above.

Another embodiment of the present invention relates to a genetically modified plant for producing short chain fatty acids by a biosynthetic process, the plant being transformed with a recombinant nucleic acid molecule as described above.

Yet another embodiment of the present invention relates to a genetically modified microorganism for producing short chain fatty acids by a biosynthetic process. The microorganism comprises a nucleic acid molecule encoding a fatty acid synthase, wherein the nucleic acid molecule has been modified to increase the expression or biological activity of the fatty acid synthase. The fatty acid synthase comprises an amino acid sequence selected from: (a) an amino acid sequence selected from the group consisting of: SEQ ID NO:2, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, an amino acid sequence consisting of positions 1-500 of SEQ ID NO:2, an amino acid sequence consisting of positions 450-1300 of SEQ ID NO:2, an amino acid sequence consisting of positions 1250-1700 of SEQ ID NO:2, an amino acid sequence consisting of positions 1575-2100 of SEQ ID NO:2, an amino acid sequence consisting of positions 2025-2850 of SEQ ID NO:2, an amino acid sequence consisting of positions 2800-3350 of SEQ ID NO:2, an amino acid sequence consisting of positions 3300-3900 of SEQ ID NO:2, an amino acid sequence consisting of positions 3900-4136 of SEQ ID NO:2, and a biologically active fragment thereof; or (b) an amino acid sequence that is at least about 45% identical to any of the amino acid sequences of (a) and having the biological activity of the amino acid sequence of (a). In one embodiment, the nucleic acid molecule encoding a fatty acid synthase is an endogenous gene in the microorganism. In another embodiment, the microorganism has been transformed with a nucleic acid molecule encoding the fatty acid synthase. In yet another embodiment, the microorganism comprises an endogenous gene encoding the fatty acid synthase and has been transformed with a recombinant nucleic acid molecule encoding a fatty acid synthase. In this embodiment, one or both of the gene and the recombinant nucleic acid molecule has been modified to increase the expression or biological activity of the fatty acid synthase. Such genetically modified microorganisms can include Thraustochytriales microorganism, and in one aspect, a *Schizochytrium* microorganism.

Another embodiment of the invention relates to a biomass comprising the genetically modified microorganism described above, to a food product comprising such a biomass, or to a pharmaceutical product comprising such a biomass.

Another embodiment of the present invention relates to a method to produce short chain fatty acids by a biosynthetic process, comprising culturing in a fermentation medium a genetically modified microorganism as described above. Another embodiment of the present invention relates to a method to produce short chain fatty acids by a biosynthetic process, comprising growing a genetically modified plant that has been transformed with a recombinant nucleic acid molecule as described above.

Yet another embodiment of the present invention relates to an oligonucleotide, comprising at least 12 contiguous nucleotides of SEQ ID NO:1, SEQ ID NO:3, or SEQ ID NO:4, or a nucleic acid sequence fully complementary thereto.

Another embodiment of the present invention relates to a genetically modified microorganism with reduced production of short chain fatty acids, wherein the microorganism has been genetically modified to selectively attenuate a fatty acid synthase gene or portion thereof encoding a functional domain. The fatty acid synthase gene comprises a nucleic acid sequence selected from: (a) a nucleic acid sequence encoding SEQ ID NO:2; and (b) a nucleic acid sequence encoding an amino acid sequence that is at least about 45% identical to SEQ ID NO:2, wherein the protein having the amino acid sequence has a biological activity selected from the group consisting of acetyl-transferase (AT) activity; enoyl ACP reductase (ER) activity; dehydrase (DH) activity; malonyl/palmitoyl acyltransferase (M/PAT) activity; a first acyl carrier protein (ACP) activity; a second acyl carrier protein (ACP) activity; keto-acyl ACP reductase (KR) activity; keto-acyl ACP synthase (KS) activity; and phosphopantetheinyl transferase (PPT) activity. In one aspect, the fatty acid synthase gene comprises a nucleic acid sequence represented by SEQ ID NO:1. In another aspect, the microorganism has increased production of at least one polyunsaturated fatty acid (PUFA). The microorganism can include, but is not limited to, a Thraustochytriales microorganism, and particularly, a *Schizochytrium*. In one aspect, the fatty acid synthase gene has been modified in a regulatory region to reduce expression of the gene. In another aspect, the fatty acid synthase gene has been modified in the coding region to reduce the biological activity of one or more functional domains of the fatty acid synthase. In yet another aspect, the fatty acid synthase gene has been mutated by targeted homologous recombination with a nucleic acid sequence that hybridizes to the fatty acid synthase gene and includes a heterologous nucleic acid sequence that modifies the coding region of the fatty acid synthase gene to reduce the expression or activity of the fatty acid synthase encoded thereby.

Another embodiment of the invention relates to a biomass comprising the genetically modified microorganisms described directly above, wherein the microorganisms have reduced production of short chain fatty acids as compared to a wild-type microorganism of the same species. Also included in the invention are food products and pharmaceutical products comprising such a biomass.

Yet another embodiment of the present invention relates to a method for increasing the production of polyunsaturated fatty acids (PUFAs) in a biosynthetic process. The method includes the step of culturing under conditions effective to produce lipids comprising the PUFAs, genetically modified microorganisms as set forth directly above. Products comprising the lipids produced by such a method, including food products and pharmaceutical products, are also encompassed by the present invention.

BRIEF DESCRIPTION OF THE FIGURES OF THE INVENTION

FIG. 2B is a schematic representation of the events that are believed to occur and result in the stable inactivation of the FAS gene in *Schizochytrium*.

DETAILED DESCRIPTION OF THE INVENTION

Figure 1:
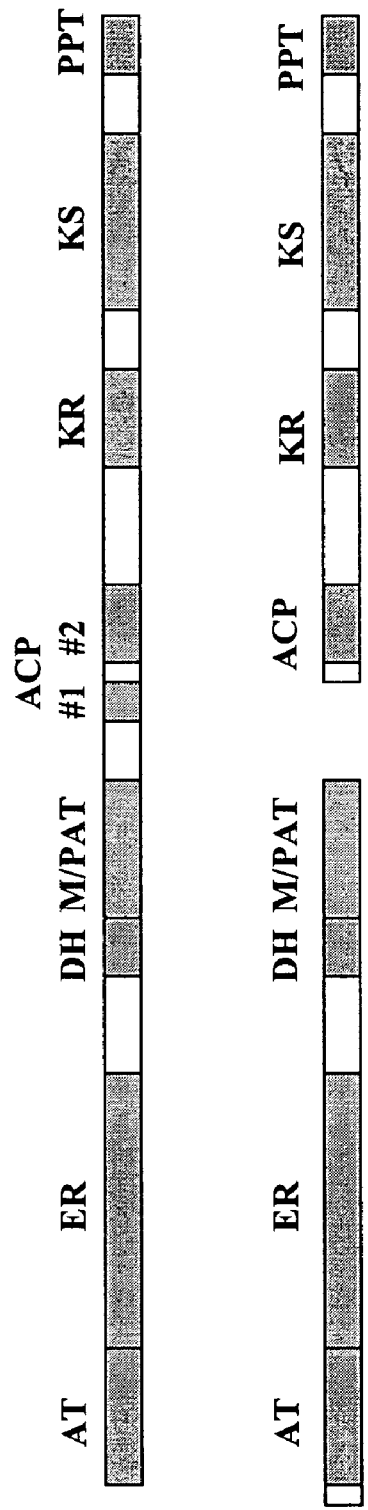
FIG. 1 is a schematic representation of the putative enzymatic domains present in the *Schizochytrium* FAS protein.

The present invention generally relates to a fatty acid synthase (FAS) from *Schizochytrium*, to biologically active fragments and homologues thereof, to a nucleic acid sequence encoding such FAS, fragments and homologues thereof, to the gene encoding *Schizochytrium* FAS, to host cells and organisms that recombinantly express the FAS, to host cells and organisms in which the expression and/or activity of the endogenous FAS has been attenuated, and to various methods for making and using any of these proteins, nucleic acid molecules, genes, host cells or organisms. The FAS protein of the present invention is a protein with multiple enzymatic domains that are homologous, in terms of both amino acid sequences and in linear domain organization, to the enzymatic domains encompassed by two proteins in fungi. The FAS domains in mammals are also found on one large protein, but the organization and the specific types of enzymatic activities of the domains are significantly different than the *Schizochytrium* and fungal FAS. Additionally, the amino acid sequence homology between the *Schizochytrium* FAS domains and those found in mammalian FAS is significantly less than between *Schizochytrium* and fungal FAS.

This discovery of a multi-functional protein provides a novel approach for the economic production of short chain fatty acids. For example, it is now possible to clone and express one gene with key sequential enzymatic functions that are found in at least two genes in other (non-mammalian) organisms, which will greatly facilitate the genetic modification of production organisms. In addition, it is possible to use the enzymatic domains of the *Schizochytrium* FAS gene individually or in various combinations to construct various recombinant/synthetic genes expressing, one or more of the domains.

More specifically, the present inventors have cloned a region of genomic DNA from *Schizochytrium* sp. ATCC 20888 that contains a single orf (open reading frame) that encodes a fatty acid synthase (FAS gene). The putative function of the enzyme, (i.e., synthesis of short chain saturated fatty acids such as C14:0 and C16:0), was verified by showing that strains in which the gene had been disrupted require supplementation with short chain fatty acids for survival. The FAS encoded by the *Schizochytrium* gene has some novel features. The organization of the domains in the protein is similar to that found in many fungi (e.g., baker's yeast). However, in all of the fungal enzymes characterized to date, the FAS is encoded in two subunits (i.e., two proteins), while the *Schizochytrium* FAS is one large protein. Based on homology to the fungal systems, it is likely that the *Schizochytrium* FAS uses acetyl-CoA and malonyl-CoA along with NADH and NADPH as substrates. The product is probably released as an acyl-CoA ester. As in yeast, the protein contains a phosphopantetheinyl transferase domain that is believed to activate an embedded acyl carrier protein domain. The *Schizochytrium* FAS is an 'all-in-one' protein for short chain saturated fatty acid synthesis.

As used herein, a short chain fatty acid is defined as a fatty acid having 18 or fewer carbons. The FAS system of the invention produces short chain fatty acids, which can include any short chain fatty acid, and typically fatty acids having 16, 14, or 12 carbons, and include saturated and monounsaturated fatty acids. For example, short chain fatty acids produced by a FAS system include, but are not limited to, short chain saturated fatty acids such as C14:0 and C16:0. The present invention encompasses the production of any product of the FAS system.

*Schizochytrium* is a marine microalga that has been developed as a commercial source of oil enriched in DHA. The DHA in *Schizochytrium* is the product of a highly specialized PUFA synthase (described in PCT Publication No. WO 00/42195 and PCT Publication No. WO 02/083870). Here the present inventors describe the FAS that is responsible for producing the other major fatty acids (C14:0 and C16:0) found in *Schizochytrium* oil. The products of the FAS of the present invention are of interest by themselves and as a major component of the DHA-enriched oil. Alteration of the activity of the FAS in *Schizochytrium* may influence the relative amounts of DHA and medium chain saturated fatty acids that accumulate in that oil, thereby altering its commercial value as a DHA-enriched oil.

Accordingly, the *Schizochytrium* FAS gene and its encoded product as described herein have several uses. First, subclones of the FAS genomic region can be used to make a knockout plasmid construct and to create mutants of *Schizochytrium* in which the FAS gene has been inactivated. Such constructs have already been produced by the inventors and are described herein (see Examples 2 and 3). These mutants may have utility in a variety of biochemical and genetic studies. In addition, attenuation of the expression and/or activity of the FAS gene in Thraustochytrids such as *Schizochytrium* is a particularly preferred embodiment of the invention, because reduction of FAS activity in Thraustochytrids is predicted to increase the accumulation of highly desirable long chain fatty acids in the organism. For example, one embodiment of the invention relates to an organism of the order, Thraustochytriales, in which the FAS gene expression is attenuated (resulting in reduced FAS activity), thereby increasing the accumulation of long chain fatty acids and particularly, polyunsaturated fatty acids (PUFAs), by the organism. According to the present invention, reference to an attenuated gene or protein is to a gene or protein that is not deleted or completely activated, but for which the expression and/or biological activity has been reduced (inhibited, down-regulated, decreased) as compared to the expression and/or biological activity of the wild-type gene or protein under normal conditions. Therefore, a FAS having attenuated expression or activity is still expressed and still has some biological activity (e.g., so that an organism expressing the FAS is viable), but the expression or biological activity is reduced as compared to the wild-type FAS.

In another embodiment, expression of this gene in heterologous systems (such as in the cytoplasm of plant cells) is expected to lead to the production and accumulation of short chain saturated fatty acids in those cells. This will provide a means to produce oils enriched in short chain fatty acids in commercial oil-seed crops. This would be an alternative method to the current use of chain-length specific thioesterases targeted to the plastids of plant cells. The end product of the *Schizochytrium* FAS is likely to be an ester of CoA, and therefore it would be compatible with oil and phospholipid synthesis in the plant cell cytoplasm.

Accordingly, one embodiment of the present invention relates to an isolated fatty acid synthase (FAS). As used herein, reference to an isolated protein, including an isolated FAS, is to a protein (including a polypeptide or peptide) that has been removed from its natural milieu (i.e., that has been subject to human manipulation) and can include purified proteins, partially purified proteins, recombinantly produced proteins, and synthetically produced proteins, for example. As such, "isolated" does not reflect the extent to which the protein has been purified. Preferably, an isolated FAS of the present invention is produced recombinantly. In addition, and by way of example, a "*Schizochytrium* FAS" refers to a FAS (generally including a homologue of a naturally occurring FAS) from a *Schizochytrium* or to a FAS protein that has been otherwise produced from the knowledge of the structure (e.g., sequence) and perhaps the function of a naturally occurring FAS from *Schizochytrium*. In other words, a *Schizochytrium* FAS includes any FAS that has substantially similar structure and function of a naturally occurring FAS from *Schizochytrium* or that is a biologically active (i.e., has biological activity) homologue of a naturally occurring FAS from *Schizochytrium* as described in detail herein. As such, a *Schizochytrium* FAS protein can include purified, partially purified, recombinant, mutated/modified and synthetic proteins. According to the present invention, the terms "modification" and "mutation" can be used interchangeably, particularly with regard to the modifications/mutations to the amino acid sequences of FAS (or nucleic acid sequences) described herein.

According to the present invention, a homologue of a FAS protein (i.e., a FAS homologue) includes FAS proteins in which at least one or a few, but not limited to one or a few, amino acids have been deleted (e.g., a truncated version of the protein, such as a peptide or fragment), inserted, inverted, substituted and/or derivatized (e.g., by glycosylation, phosphorylation, acetylation, myristoylation, prenylation, palmitation, farnasylation, amidation and/or addition of glycosylphosphatidyl inositol). In a preferred embodiment, a FAS homologue has measurable or detectable FAS enzymatic activity (i.e., has biological activity). Measurable or detectable FAS enzymatic activity can include the enzymatic activity of just one, two, three, etc., up to all ten of the functional domains in the FAS protein of the present invention (discussed in detail below). In another embodiment, a FAS homologue may or may not have measurable FAS functional (biological) activity, but is used for the preparation of antibodies or the development of oligonucleotides useful for identifying other FAS proteins. For example, the production of an antibody against FAS and production of probes and primers useful in the cloning of a FAS are useful for tracking the presence of FAS nucleic acids or proteins in genetically modified organisms or for identifying naturally occurring FAS homologues in other organisms (e.g., in other members of Thraustochytriales).

FAS homologues can be the result of natural allelic variation or natural mutation. FAS homologues of the present invention can also be produced using techniques known in the art including, but not limited to, direct modifications to the protein or modifications to the gene encoding the protein using, for example, classic or recombinant DNA techniques to effect random or targeted mutagenesis. A naturally occurring allelic variant of a nucleic acid encoding a FAS protein is a gene that occurs at essentially the same locus (or loci) in the genome as the gene which encodes the FAS protein of the present invention (e.g., SEQ ID NO:2), but which, due to natural variations caused by, for example, mutation or recombination, has a similar but not identical sequence. Natural allelic variants typically encode proteins having similar activity to that of the protein encoded by the gene to which they are being compared. One class of allelic variants can encode the same protein but have different nucleic acid sequences due to the degeneracy of the genetic code. Allelic variants can also comprise alterations in the 5' or 3' untranslated regions of the gene (e.g., in regulatory control regions). Allelic variants are well known to those skilled in the art. Homologues can be produced using techniques known in the art for the production of proteins including, but not limited to, direct modifications to the isolated, naturally occurring protein, direct protein synthesis, or modifications to the nucleic acid sequence encoding the protein using, for example, classic or recombinant DNA techniques to effect random or targeted mutagenesis.

Modifications in FAS homologues, as compared to the wild-type protein, increase, decrease, or do not substantially change, the basic biological activity of the FAS homologue as compared to the naturally occurring protein, FAS. In general, the biological activity or biological action of a protein refers to any function(s) exhibited or performed by the protein that is ascribed to the naturally occurring form of the protein as measured or observed in vivo (i.e., in the natural physiological environment of the protein) or in vitro (i.e., under laboratory conditions). Modifications of a protein, such as in a homologue or mimetic (discussed below), may result in proteins having the same biological activity as the naturally occurring protein, or in proteins having decreased or increased biological activity as compared to the naturally occurring protein. Modifications which result in a decrease in protein expression or a decrease in the activity of the protein, can be referred to as inactivation (complete or partial), down-regulation, or decreased action of a protein. Similarly, modifications which result in an increase in protein expression or an increase in the activity of the protein, can be referred to as amplification, overproduction, activation, enhancement, up-regulation or increased action of a protein.

According to one embodiment of the present invention, a biologically active FAS, including a biologically active homologue or fragment thereof, has at least one characteristic of biological activity of activity a wild-type, or naturally occurring, FAS protein described herein. A FAS biological activity includes the ability to catalyze the synthesis of short chain fatty acids, including by using acetyl-CoA and malonyl-CoA along with NADH and NADPH as substrates to produce a short chain fatty acid. More particularly, a FAS biological activity can include any one or more of the biological activities of the nine domains of FAS described herein. According to the present invention, a FAS protein of the present invention has at least one, and preferably two, and more preferably three, and more preferably four, and more preferably five, and more preferably six, and more preferably seven, and more preferably eight, and most preferably nine, biological activities. These biological activities are: (1) acetyl-transferase (AT) activity; (2) enoyl ACP reductase (ER) activity; (3) dehydratase (DH) activity; (4) malonyl/palmitoyl acyltransferase (M/PAT) activity; (5) a first acyl carrier protein (ACP) activity; (6) a second acyl carrier protein (ACP) activity; (7) keto-acyl ACP reductase (KR) activity; (8) keto-acyl ACP synthase (KS) activity; and (9) phosphopantetheinyl transferase (PPT) activity. General reference to FAS biological activity typically refers to all biological activities, but does not exclude reference to only one, two, three, four, five, six, seven or eight of the biological activities. Methods for measuring these various activities are known in the art.

Methods to measure protein expression levels according to this invention, include, but are not limited to: Western blot, immunoblot, enzyme-linked immunosorbant assay (ELISA), radioimmunoassay (RIA), immunoprecipitation, surface plasmon resonance, chemiluminescence, fluorescent polarization, phosphorescence, immunohistochemical analysis, matrix-assisted laser desorption/ionization time-of-flight (MALDI-TOF) mass spectrometry, microcytometry, microarray, microscopy, fluorescence activated cell sorting (FACS), and flow cytometry, as well as assays based on a property of the protein including but not limited to substrate binding. Binding assays are also well known in the art. For example, a BIAcore machine can be used to determine the binding constant of a complex between two proteins. The dissociation constant for the complex can be determined by monitoring changes in the refractive index with respect to time as buffer is passed over the chip (O'Shannessy et al. Anal. Biochem. 212:457-468 (1993); Schuster et al., Nature 365:343-347 (1993)). Other suitable assays for measuring the binding of one protein to another include, for example, immunoassays such as enzyme linked immunoabsorbent assays (ELISA) and radioimmunoassays (RIA), or determination of binding by monitoring the change in the spectroscopic or optical properties of the proteins through fluorescence, UV absorption, circular dichrosim, or nuclear magnetic resonance (NMR).

FIG. 1 is a schematic drawing showing the domain organization of the Schizochytrium FAS protein of the present invention as compared to the domain organization of the individual α and β subunit proteins of yeast FAS systems.

The complete Schizochytrium FAS-encoding sequence is a 12,408 nucleotide sequence (not including the stop codon), represented herein by SEQ ID NO:1, which encodes a 4136 amino acid sequence, represented herein as SEQ ID NO:2. Within the Schizochytrium FAS protein are nine domains as described above: (a) one acetyl-transferase (AT) domain; (b)

one enoyl ACP reductase (ER) domain; (c) one dehydrase (DH) domain; (d) one malonyl/palmitoyl acyltransferase (M/PAT) domain; (e) two acyl carrier protein (ACP) domains; (f) one keto-acyl ACP reductase (KR) domain; (g) one keto-acyl ACP synthase (KS) domain; and (h) one phosphopantetheinyl transferase (PPT) domain.

SEQ ID NO:2 was compared with known sequences in a standard protein BLAST search (BLAST 2.0 Basic BLAST homology search using blastp for amino acid searches, wherein the query sequence is filtered for low complexity regions by default (described in Altschul, S. F., Madden, T. L., Schäaffer, A. A., Zhang, J., Zhang, Z., Miller, W. & Lipman, D. J. (1997) "Gapped BLAST and PSI-BLAST: a new generation of protein database search programs." Nucleic Acids Res. 25:3389-3402, incorporated herein by reference in its entirety)). The BLAST search used the following parameters: low complexity filter Off, matrix=BLOSUM62, gap penalties are: Existence: 11, Extension 1. BLAST results of entire FAS protein revealed that the *Schizochytrium* FAS can be viewed in general, as a protein with homology to a head to tail fusion of fungal α and β FAS subunits. All of the domains currently identified in the two yeast proteins have counterparts in the *Schizochytrium* FAS. In addition, the *Schizochytrium* FAS has a second ACP domain. In all cases, the best matches in the BLAST results are fungi such as: *Saccharomyces cerevisiae, Candida albicans, Neurospora crassa, Saccharomyces kluyveri, Aspergillus nidulans* and *Yarrowia lipolytica*. At the amino acid level, the sequences with the greatest degree of homology to SEQ ID NO:2 were: (1) the *Candida albicans* FAS β-subunit (GenBank Accession No. P34731), which was 34% identical to amino acids 1-2100 of SEQ ID NO:2 (identity was actually over 2038 amino acids of this region of SEQ ID NO:2); and (2) *Candida albicans* FAS α-subunit (GenBank Accession No. P43098), which was 41% identical to amino acids 2101-4136 of SEQ ID NO:2 (identity was actually over 1864 amino acids of this region of SEQ ID NO:2). Several other yeast strains showed similar homology to this portion of *Schizochytrium* FAS. Since yeast FAS systems have only one ACP domain, whereas the *Schizochytrium* FAS described herein has two ACP domains, the homology to the yeast α-subunit is found from the second of the two ACPs in *Schizochytrium* through the end of the protein.

The first domain in the *Schizochytrium* FAS protein is an acetyl-transferase (AT) domain, also referred to herein as FAS-AT. This domain is contained within a region of SEQ ID NO:2 spanning from about position 1 to about position 500 of SEQ ID NO:2. The amino acid sequence containing the FAS-AT domain is represented herein as SEQ ID NO:5 (positions 45-415 of SEQ ID NO:2). BLAST results show that this domain has high homology to the first domain of several fungal FAS β-subunits. The fungal protein having the closest identity to this domain of the FAS protein of the present invention is a portion of a *Yarrowia lipolytica* FAS β-subunit (GenBank Accession No. P34229), which is 30% identical over 392 amino acids when compared to SEQ ID NO:5 (i.e., containing the AT domain of the FAS of the present invention). An AT generally refers to a class of enzymes that can carry out a number of distinct acyl transfer reactions. The fungal FAS β-subunit has been shown to have specifically acetyltransacylase activity, which is related to malonyl acyltransferase, except that it transfers an acetyl group which serves as the primer for fatty acid synthesis. In the AT domain, the active site motif is identified as GHS*XG, which in SEQ ID NO:2 is GHS*QG (positions 156-160 of SEQ ID NO:2), where S* (position 158 of SEQ ID NO:2) is the acyl group binding site.

The second domain in the *Schizochytrium* FAS protein is an enoyl reductase (ER) domain, also referred to herein as FAS-ER. This domain is contained within a region of SEQ ID NO:2 spanning from about position 450 to about position 1300 of SEQ ID NO:2. The amino acid sequence containing the FAS-ER domain is represented herein as SEQ ID NO:6 (positions 460-1210 of SEQ ID NO:2). BLAST results show that this domain has high homology to the second domain of several fungal FAS β-subunits. The fungal protein having the closest identity to this domain of the FAS protein of the present invention is a portion of a *Emericella nidulans* FAS β-subunit (GenBank Accession No. AAB41494.1), which is 46% identical over 561 amino acids when compared to SEQ ID NO:6 (i.e., containing the ER domain of the FAS of the present invention). An ER enzyme reduces the trans-double bond (introduced by the DH activity) in the fatty acyl-ACP, resulting in fully saturating those carbons.

The third domain in the *Schizochytrium* FAS protein is a dehydratase (DH) domain, also referred to herein as FAS-DH. This domain is contained within a region of SEQ ID NO:2 spanning from about position 1300 to about position 1700 of SEQ ID NO:2. The amino acid sequence containing the FAS-DH domain is represented herein as SEQ ID NO:7 (positions 1450-1575 of SEQ ID NO:2). BLAST results show that this domain has high homology to the third domain of several fungal FAS β-subunits. The fungal protein having the closest identity to this domain of the FAS protein of the present invention is the *Magnaporthe grisea* monoamine oxidase C (MaoC) protein (GenBank Accession No. EAA50359.1), which is 39% identical over 121 amino acids when compared to SEQ ID NO:7 (i.e., containing the DH domain of the FAS of the present invention). MaoC shares similarity with a family of proteins with a variety of functions, including the FAS β-keto-acyl dehydratase (DH) activity. This class of enzymes removes HOH from a β-keto acyl-ACP and leaves a trans double bond in the carbon chain.

The fourth domain in the *Schizochytrium* FAS protein is a malonyl/palmitoyl acyltransferase (M/PAT) domain, also referred to herein as FAS-M/PAT. This domain is contained within a region of SEQ ID NO:2 spanning from about position 1575 to about position 2100 of SEQ ID NO:2. The amino acid sequence containing the FAS-M/PAT domain is represented herein as SEQ ID NO:8 (positions 1575-2025 of SEQ ID NO:2). BLAST results show that this domain has high homology to the fourth domain of several fungal FAS β-subunits. The fungal protein having the closest identity to this domain of the FAS protein of the present invention is a portion of a *Neurospora crassa* protein (GenBank Accession No. EAA33229.1), which is 47% identical over 397 amino acids when compared to SEQ ID NO:8 (i.e., containing the M/PAT domain of the FAS of the present invention). In yeast FAS, FabD (malonyl-CoA:ACP acyltransferase) has been shown to have the dual functions of transferring the malonyl group from CoA to the FAS ACP domain, and also of transferring the fatty acid product of FAS (a palmitoyl group) from the FAS ACP to CoA. The active site motif of this protein is GHS*XG, which in the *Schizochytrium* FAS-M/PAT is GHS*LG (positions 1723-1727 of SEQ ID NO:2), where the S* (position 1725 of SEQ ID NO:2) is the position where the acyl group binds.

The fifth and sixth domains in the *Schizochytrium* FAS protein are acyl carrier protein (ACP) domains, also referred to herein as FAS-ACP. These domains are contained within a region of SEQ ID NO:2 spanning from about position 2025 to about position 2850 of SEQ ID NO:2. The amino acid sequence containing the first FAS-ACP domain (FAS-ACP1) is represented herein as SEQ ID NO:9 (positions 2140-2290 of SEQ ID NO:2). The amino acid sequence containing the second FAS-ACP domain (FAS-ACP2) is represented herein as SEQ ID NO:10 (positions 2325-2585 of SEQ ID NO:2). BLAST results show that these domains have high homology to the N-terminus of several yeast FAS α-subunits which have been designated in the literature as ACP domains. However, all fungal FAS proteins appear to have only one ACP domain, whereas the *Schizochytrium* FAS protein of the present invention has two ACP domains. The fungal protein having the closest identity to the first ACP domain of the FAS protein of the present invention is a portion of a *Neurospora crassa* protein (GenBank Accession No. EAA33230.1), which is 44% identical over 149 amino acids when compared to SEQ ID NO:9 (i.e., containing the first ACP domain of the FAS of the present invention). The fungal protein having the closest identity to the second ACP domain of the FAS protein of the present invention is a portion of a *Neurospora crassa* protein (GenBank Accession No. EAA33230.1), which is 36% identical over 262 amino acids when compared to SEQ ID NO:10 (i.e., containing the second ACP domain of the FAS of the present invention). By alignment with the yeast sequences, two putative phosphopanthelyation sites are identified in the ACP domains: the serine residues at positions 2160 (in FAS-ACP1) and 2353 (in FAS-ACP-2) of SEQ ID NO:2. A domain or protein having acyl carrier protein (ACP) biological activity (function) is characterized as being a small polypeptide (typically, 80 to 100 amino acids long), that functions as a carrier for growing fatty acyl chains via a thioester linkage to a covalently bound co-factor of the protein. They occur as separate units or as domains within larger proteins. ACPs are converted from inactive apo-forms to functional holo-forms by transfer of the phosphopantetheinyl moiety of CoA to a highly conserved serine residue of the ACP. Acyl groups are attached to ACP by a thioester linkage at the free terminus of the phosphopantetheinyl moiety.

The seventh domain in the *Schizochytrium* FAS protein is a keto-acyl ACP reductase (KR) domain, also referred to herein as FAS-KR. This domain is contained within a region of SEQ ID NO:2 spanning from about position 2800 to about position 3350 of SEQ ID NO:2. The amino acid sequence containing the FAS-KR domain is represented herein as SEQ ID NO:11 (positions 2900-3100 of SEQ ID NO:2). BLAST results show that this domain has high homology to the second domain of several fungal FAS α-subunits (FabG or β-keto-acyl ACP reductase). The fungal protein having the closest identity to this domain of the FAS protein of the present invention is a portion of a *Neurospora crassa* protein (GenBank Accession No. EAA33220.1), which is 50% identical over 205 amino acids when compared to SEQ ID NO:11 (i.e., containing the KR domain of the FAS of the present invention). As in the yeast FAS, a domain or protein having keto-acyl ACP reductase (KR) biological activity (function), is characterized as an enzyme that catalyzes the pyridine-nucleotide-dependent reduction of β-keto acyl forms of ACP. It is the first reductive step in the de novo fatty acid biosynthesis elongation cycle.

The eighth domain in the *Schizochytrium* FAS protein is a keto-acyl ACP synthase (KS) domain, also referred to herein as FAS-KS. This domain is contained within a region of SEQ ID NO:2 spanning from about position 3300 to about position 3900 of SEQ ID NO:2. The amino acid sequence containing the FAS-KS domain is represented herein as SEQ ID NO:12 (positions 3350-3875 of SEQ ID NO:2). BLAST results show that this domain has high homology to the third domain of several fungal FAS α-subunits, and particularly, FabB (β-keto-acyl ACP synthase). The fungal protein having the closest identity to this domain of the FAS protein of the present invention is a portion of a *Candida albicans* FAS α-subunit protein (GenBank Accession No. P43098), which is 55% identical over 548 amino acids when compared to SEQ ID NO:12 (i.e., containing the KS domain of the FAS of the present invention). The active site cysteine of this domain has been identified at position 3530 of SEQ ID NO:2. According to the present invention, a domain or protein having (KS) biological activity (function) is characterized as an enzyme that carries out the initial step of the FAS elongation reaction cycle. The acyl group destined for elongation is linked to a cysteine residue at the active site of the enzyme by a thioester bond. In the multi-step reaction, the acyl-enzyme undergoes condensation with malonyl-ACP to form -keto-acyl-ACP, $CO_2$ and free enzyme. The KS plays a key role in the elongation cycle and in many systems has been shown to possess greater substrate specificity than other enzymes of the reaction cycle.

The ninth domain in the *Schizochytrium* FAS protein is a phosphopantetheinyl transferase (PPT domain), also referred to herein as FAS-PPT. This domain is contained within a region of SEQ ID NO:2 spanning from about position 3900 to about position 4136 of SEQ ID NO:2. The amino acid sequence containing the FAS-PPT domain is represented herein as SEQ ID NO:13 (positions 4025-4136 of SEQ ID NO:2). BLAST results show that this domain has high homology to the C-terminal domain of several fungal FAS α-subunits, and particularly, to AcpS (holo-ACP synthase, also known as 4-phosphopantetheinyl transferase). The fungal protein having the closest identity to this domain of the FAS protein of the present invention is a portion of a Schizosaccharomyces pombe FAS α-subunit protein (GenBank Accession No. BAB6203 1.1), which is 46% identical over 110 amino acids when compared to SEQ ID NO:13 (i.e., containing the PPT domain of the FAS of the present invention). A PPT domain is required for the attachment of a phosphopantetheine cofactor to produce the active, holo-ACP.

In one embodiment, a FAS protein (e.g., including homologues of the FAS isolated from *Schizochytrium* and described in detail herein) includes proteins that have at least one of: (a) acetyl-transferase (AT) activity; (b) enoyl ACP reductase (ER) activity; (c) dehydratase (DH) activity; (d) malonyl/palmitoyl acyltransferase (M/PAT) activity; (e) acyl carrier protein (ACP) activity; (f) keto-acyl ACP reductase (KR) activity; (g) keto-acyl ACP synthase (KS) activity; and (h) phosphopantetheinyl transferase (PPT) activity. In one embodiment of the invention, an isolated FAS comprises an amino acid sequence selected from: (a) an amino acid sequence selected from: SEQ ID NO:2, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, an amino acid sequence consisting of positions 1-500 of SEQ ID NO:2, an amino acid sequence consisting of positions 450-1300 of SEQ ID NO:2, an amino acid sequence consisting of positions 1250-1700 of SEQ ID NO:2, an amino acid sequence consisting of positions 1575-2100 of SEQ ID NO:2, an amino acid sequence consisting of positions 2025-2850 of SEQ ID NO:2, an amino acid sequence consisting of positions 2800-3350 of SEQ ID NO:2, an amino acid sequence consisting of positions 3300-3900 of SEQ ID NO:2, an amino acid sequence consisting of positions 3900-4136 of SEQ ID NO:2, or biologically active fragments of any of these sequences or any combinations of these sequences; or, (b) an amino acid sequence that is at least about 45% identical to any of these sequences, wherein the amino acid sequence has the biological activity of the reference sequence (biological activities of these sequences are described above).

In one aspect of the invention, as discussed above a FAS protein comprises an amino acid sequence that is at least about 45% identical to any of the above-described amino acid sequences representing the full-length FAS of the invention (i.e., SEQ ID NO:2), a region containing a biologically active domain of the FAS of the invention (i.e., a region of SEQ ID NO:2 defined by positions numbers above), or a biologically active domain of the FAS of the invention (i.e., any one of SEQ ID NOs:5-13), over the full length of that protein, region, or domain. In another aspect, a FAS protein of the invention comprises an amino acid sequence that is at least 50% identical to any of the above-identified protein, regions or domains, and in another aspect at least about 55%, and in another aspect at least about 60%, and in another aspect at least about 65%, and in another aspect at least about 70%, and in another aspect at least about 75%, and in another aspect at least about 80%, and in another aspect at least about 85%, and in another aspect at least about 90%, and in another aspect at least about 95% identical, and in another aspect at least about 96% identical, and in another aspect at least about 97% identical, and in another aspect at least about 98% identical, and in another aspect at least about 99% identical, to the amino acid sequence defining any of the above-identified protein, regions or domains. Preferably, a FAS protein of the present invention comprises at least one, two, three, four, five, six, seven, eight, or all nine biological activities of a FAS protein of the invention selected from: (a) acetyl-transferase (AT) activity; (b) enoyl ACP reductase (ER) activity; (c) dehydratase (DH) activity; (d) malonyl/palmitoyl acyltransferase (M/PAT) activity; (e) acyl carrier protein (ACP) activity; (f) keto-acyl ACP reductase (KR) activity; (g) keto-acyl ACP synthase (KS) activity; and (h) phosphopantetheinyl transferase (PPT) activity.

In one embodiment of the present invention, a FAS homologue according to the present invention has an amino acid sequence that is less than about 100% identical to any of the above-identified amino acid sequences for a full-length FAS protein, or a region or domain thereof according to the present invention. In another aspect of the invention, a FAS homologue according to the present invention has an amino acid sequence that is less than about 99% identical to any of the above-identified amino acid sequences, and in another embodiment, is less than is less than 98% identical to any of the above-identified amino acid sequences, and in another embodiment, is less than 97% identical to any of the above-identified amino acid sequences, and in another embodiment, is less than 96% identical to any of the above-identified amino acid sequences, and in another embodiment, is less than 95% identical to any of the above-identified amino acid sequences, and in another embodiment, is less than 94% identical to any of the above-identified amino acid sequences, and in another embodiment, is less than 93% identical to any of the above-identified amino acid sequences, and in another embodiment, is less than 92% identical to any of the above-identified amino acid sequences, and in another embodiment, is less than 91% identical to any of the above-identified amino acid sequences, and in another embodiment, is less than 90% identical to any of the above-identified amino acid sequences, and so on, in increments of whole integers.

As used herein, unless otherwise specified, reference to a percent (%) identity refers to an evaluation of homology which is performed using: (1) a BLAST 2.0 Basic BLAST homology search using blastp for amino acid searches and blastn for nucleic acid searches with standard default parameters, wherein the query sequence is filtered for low complexity regions by default (described in Altschul, S. F., Madden, T. L., Schäffer, A. A., Zhang, J., Zhang, Z., Miller, W. & Lipman, D. J. (1997) "Gapped BLAST and PSI-BLAST: a new generation of protein database search programs." Nucleic Acids Res. 25:3389-3402, incorporated herein by reference in its entirety); (2) a BLAST 2 alignment (using the parameters described below); (3) and/or PSI-BLAST with the standard default parameters (Position-Specific Iterated BLAST. It is noted that due to some differences in the standard parameters between BLAST 2.0 Basic BLAST and BLAST 2, two specific sequences might be recognized as having significant homology using the BLAST 2 program, whereas a search performed in BLAST 2.0 Basic BLAST using one of the sequences as the query sequence may not identify the second sequence in the top matches. In addition, PSI-BLAST provides an automated, easy-to-use version of a "profile" search, which is a sensitive way to look for sequence homologues. The program first performs a gapped BLAST database search. The PSI-BLAST program uses the information from any significant alignments returned to construct a position-specific score matrix, which replaces the query sequence for the next round of database searching. Therefore, it is to be understood that percent identity can be determined by using any one of these programs.

Two specific sequences can be aligned to one another using BLAST 2 sequence as described in Tatusova and Madden, (1999), "Blast 2 sequences—a new tool for comparing protein and nucleotide sequences", FEMS Microbiol Lett. 174: 247-250, incorporated herein by reference in its entirety. BLAST 2 sequence alignment is performed in blastp or blastn using the BLAST 2.0 algorithm to perform a Gapped BLAST search (BLAST 2.0) between the two sequences allowing for the introduction of gaps (deletions and insertions) in the resulting alignment. For purposes of clarity herein, a BLAST 2 sequence alignment is performed using the standard default parameters as follows.

For blastn, using 0 BLOSUM62 matrix:
   Reward for match=1
   Penalty for mismatch=−2
   Open gap (5) and extension gap (2) penalties
   gap x_dropoff (50) expect (10) word size (11) filter (on)

For blastp, using 0 BLOSUM62 matrix:
   Open gap (11) and extension gap (1) penalties
   gap x_dropoff(50) expect (10) word size (3) filter (on).

A FAS protein can also include proteins having an amino acid sequence comprising at least 10 contiguous amino acid residues of any of the above-identified amino acid sequences (i.e., 10 contiguous amino acid residues having 100% identity with 10 contiguous amino acids of the reference amino acid sequence). In another aspect, a homologue of a FAS amino acid sequence includes amino acid sequences comprising at least 20, or at least about 30, or at least about 40, or at least about 50, or at least about 75, or at least about 100, or at least about 115, or at least about 130, or at least about 150, or at least about 200, or at least about 250, or at least about 300, or at least about 350, or at least about 400, or at least about 500, or at least about 600, or at least about 700, or at least about 800, or at least about 900, or at least about 1000, or at least about 1100, or at least about 1200, and so on, in increments of 10 amino acids, up to at least about 4130 contiguous amino acid residues of the amino acid sequence represented by SEQ ID NO:2. A FAS homologue can include proteins encoded by a nucleic acid sequence comprising at least about 30, or at least about 60, or at least about 90, or at least about 150, or at least about 225, or at least about 300, or at least about 750, or at least about 900, or at least about 1050, or at least about 1200, or at least about 1500, or at least about 1800, or at least about 2100, or at least about 2400, or at least about 2700, or at least about 3000, and so on, in increments of 30 nucleotides, up to at least about 12,400 contiguous nucleotides of the nucleic acid sequence represented by SEQ ID NO:1. In a preferred embodiment, a FAS homologue has measurable FAS biological activity (i.e., has biological activity), as described above, including any one or more of the biological activities described for a FAS of the present invention.

According to the present invention, the term "contiguous" or "consecutive", with regard to nucleic acid or amino acid sequences described herein, means to be connected in an unbroken sequence. For example, for a first sequence to comprise 30 contiguous (or consecutive) amino acids of a second sequence, means that the first sequence includes an unbroken sequence of 30 amino acid residues that is 100% identical to an unbroken sequence of 30 amino acid residues in the second sequence. Similarly, for a first sequence to have "100% identity" with a second sequence means that the first sequence exactly matches the second sequence with no gaps between nucleotides or amino acids.

In another embodiment, a FAS protein, including a FAS homologue, includes a protein having an amino acid sequence that is sufficiently similar to a natural FAS amino acid sequence that a nucleic acid sequence encoding the homologue is capable of hybridizing under moderate, high or very high stringency conditions (described below) to (i.e., with) a nucleic acid molecule encoding the natural FAS (i.e., to the complement of the nucleic acid strand encoding the natural FAS amino acid sequence). Preferably, a homologue of a FAS protein is encoded by a nucleic acid molecule comprising a nucleic acid sequence that hybridizes under moderate, high or very high stringency conditions to the complement of a nucleic acid sequence that encodes a protein comprising SEQ ID NO:2, SEQ ID NO:5, SEQ ID NO:6, SEQ ID NO:7, SEQ ID NO:8, SEQ ID NO:9, SEQ ID NO:10, SEQ ID NO:11, SEQ ID NO:12 or SEQ ID NO:13. Even more preferably, a homologue of a FAS protein is encoded by a nucleic acid molecule comprising a nucleic acid sequence that hybridizes under moderate, high or very high stringency conditions to the complement of the nucleic acid sequence represented by SEQ ID NO:1.

A nucleic acid sequence complement of nucleic acid sequence encoding a FAS of the present invention refers to the nucleic acid sequence of the nucleic acid strand that is complementary to the strand which encodes FAS. It will be appreciated that a double stranded DNA which encodes a given amino acid sequence comprises a single strand DNA and its complementary strand having a sequence that is a complement to the single strand DNA. As such, nucleic acid molecules of the present invention can be either double-stranded or single-stranded, and include those nucleic acid molecules that form stable hybrids under stringent hybridization conditions with a nucleic acid sequence that encodes the amino acid sequence of SEQ ID NO:2, for example, and/or with the complement of the nucleic acid sequence that encodes an amino acid sequence of SEQ ID NO:2. Methods to deduce a complementary sequence are known to those skilled in the art. It should be noted that since nucleic acid sequencing technologies are not entirely error-free, the sequences presented herein, at best, represent apparent sequences of a FAS protein of the present invention.

As used herein, reference to hybridization conditions refers to standard hybridization conditions under which nucleic acid molecules are used to identify similar nucleic acid molecules. Such standard conditions are disclosed, for example, in Sambrook et al., *Molecular Cloning: A Laboratory Manual*, Cold Spring Harbor Labs Press, 1989. Sambrook et al., ibid., is incorporated by reference herein in its entirety (see specifically, pages 9.31-9.62). In addition, formulae to calculate the appropriate hybridization and wash conditions to achieve hybridization permitting varying degrees of mismatch of nucleotides are disclosed, for example, in Meinkoth et al., 1984, *Anal. Biochem.* 138, 267-284; Meinkoth et al., ibid., is incorporated by reference herein in its entirety.

More particularly, moderate stringency hybridization and washing conditions, as referred to herein, refer to conditions which permit isolation of nucleic acid molecules having at least about 70% nucleic acid sequence identity with the nucleic acid molecule being used to probe in the hybridization reaction (i.e., conditions permitting about 30% or less mismatch of nucleotides). High stringency hybridization and washing conditions, as referred to herein, refer to conditions which permit isolation of nucleic acid molecules having at least about 80% nucleic acid sequence identity with the nucleic acid molecule being used to probe in the hybridization reaction (i.e., conditions permitting about 20% or less mismatch of nucleotides). Very high stringency hybridization and washing conditions, as referred to herein, refer to conditions which permit isolation of nucleic acid molecules having at least about 90% nucleic acid sequence identity with the nucleic acid molecule being used to probe in the hybridization reaction (i.e., conditions permitting about 10% or less mismatch of nucleotides). As discussed above, one of skill in the art can use the formulae in Meinkoth et al., ibid. to calculate the appropriate hybridization and wash conditions to achieve these particular levels of nucleotide mismatch. Such conditions will vary, depending on whether DNA:RNA or DNA:DNA hybrids are being formed. Calculated melting temperatures for DNA:DNA hybrids are 10° C. less than for DNA:RNA hybrids. In particular embodiments, stringent hybridization conditions for DNA:DNA hybrids include hybridization at an ionic strength of 6×SSC (0.9 M Na$^+$) at a temperature of between about 20° C. and about 35° C. (lower stringency), more preferably, between about 28° C. and about 40° C. (more stringent), and even more preferably, between about 35° C. and about 45° C. (even more stringent), with appropriate wash conditions. In particular embodiments, stringent hybridization conditions for DNA:RNA hybrids include hybridization at an ionic strength of 6×SSC (0.9 M Na$^+$) at a temperature of between about 30° C. and about 45° C., more preferably, between about 38° C. and about 50° C., and even more preferably, between about 45° C. and about 55° C., with similarly stringent wash conditions. These values are based on calculations of a melting temperature for molecules larger than about 100 nucleotides, 0% formamide and a G+C content of about 40%. Alternatively, $T_m$ can be calculated empirically as set forth in Sambrook et al., supra, pages 9.31 to 9.62. In general, the wash conditions should be as stringent as possible, and should be appropriate for the chosen hybridization conditions. For example, hybridization conditions can include a combination of salt and temperature conditions that are approximately 20-25° C. below the calculated $T_m$ of a particular hybrid, and wash conditions typically include a combination of salt and temperature conditions that are approximately 12-20° C. below the calculated $T_m$ of the particular hybrid. One example of hybridization conditions suitable for use with DNA:DNA hybrids includes a 2-24 hour hybridization in 6×SSC (50% formamide) at about 42° C., followed by washing steps that include one or more washes at room temperature in about 2×SSC, followed by additional washes at higher temperatures and lower ionic strength (e.g., at least one wash as about 37° C. in about 0.1×-0.5×SSC, followed by at least one wash at about 68° C. in about 0.1×-0.5×SSC).

FAS proteins also include expression products of fusions (e.g., fusion proteins, for example, used to overexpress soluble, active forms of the recombinant protein), of mutagenized genes (such as genes having codon modifications to enhance gene transcription and translation), and of truncated genes (such as genes having membrane binding domains removed to generate soluble forms of a membrane protein, or genes having signal sequences removed which are poorly tolerated in a particular recombinant host). It is noted that FAS and protein homologues of the present invention include proteins which do not have any FAS activity or more preferably, that have attenuated FAS activity. Such proteins are useful, for example, for the production of antibodies or for production of genetically modified organisms that lack the ability to produce one or more short chain fatty acids.

The minimum size of a protein and/or homologue of the present invention is a size sufficient to have FAS biological activity or, when the protein is not required to have such activity, sufficient to be useful for another purpose associated with a FAS protein of the present invention, such as for the production of antibodies that bind to a naturally occurring FAS. As such, the minimum size of a FAS or homologue of the present invention is a size suitable to form at least one epitope that can be recognized by an antibody, and is typically at least 8 amino acids in length, and preferably 10, and more preferably 15, and more preferably 20, and more preferably 25, and even more preferably 30 amino acids in length, and up to 4136 amino acids in length, in increments of any whole integer from 1 to 4136, with preferred sizes depending on whether full-length, multivalent (i.e., fusion protein having more than one domain, each of which has a function), or functional portions of such proteins are desired. There is no limit, other than a practical limit, on the maximum size of such a protein in that the protein can include a portion of a FAS protein (including FAS homologues) or a full-length FAS.

Similarly, the minimum size of a nucleic acid molecule of the present invention is a size sufficient to encode a protein having FAS activity (including the activity of one or more domains of a FAS of the present invention), sufficient to encode a protein comprising at least one epitope which binds to an antibody, or sufficient to form a probe or oligonucleotide primer that is capable of forming a stable hybrid with the complementary sequence of a nucleic acid molecule encoding a natural FAS (e.g., under low, moderate or high stringency conditions). As such, the size of the nucleic acid molecule encoding such a protein can be dependent on nucleic acid composition and percent homology or identity between the nucleic acid molecule and complementary sequence as well as upon hybridization conditions per se (e.g., temperature, salt concentration, and formamide concentration). The minimal size of a nucleic acid molecule that is used as an oligonucleotide primer or as a probe is typically at least about 12 to about 15 nucleotides in length if the nucleic acid molecules are GC-rich and at least about 15 to about 18 bases in length if they are AT-rich. There is no limit, other than a practical limit, on the maximal size of a nucleic acid molecule of the present invention, in that the nucleic acid molecule can include a portion of a FAS encoding sequence, a nucleic acid sequence encoding a full-length FAS (including a FAS gene), or multiple genes, or portions thereof.

The present invention also includes a fusion protein that includes a FAS-containing domain (including a homologue or functional domain of a FAS) attached to one or more fusion segments. Suitable fusion segments for use with the present invention include, but are not limited to, segments that can: enhance a protein's stability; provide other desirable biological activity; and/or assist with the purification of a FAS protein (e.g., by affinity chromatography). A suitable fusion segment can be a domain of any size that has the desired function (e.g., imparts increased stability, solubility, action or biological activity; and/or simplifies purification of a protein). Fusion segments can be joined to amino and/or carboxyl termini of the FAS-containing domain of the protein and can be susceptible to cleavage in order to enable straight-forward recovery of a FAS protein. Fusion proteins are preferably produced by culturing a recombinant cell transformed with a fusion nucleic acid molecule that encodes a protein including the fusion segment attached to either the carboxyl and/or amino terminal end of a FAS-containing domain.

In one embodiment of the present invention, any of the amino acid sequences described herein can be produced with from at least one, and up to about 20, additional heterologous amino acids flanking each of the C- and/or N-terminal ends of the specified amino acid sequence. The resulting protein or polypeptide can be referred to as "consisting essentially of" the specified amino acid sequence. According to the present invention, the heterologous amino acids are a sequence of amino acids that are not naturally found (i.e., not found in nature, in vivo) flanking the specified amino acid sequence, or that are not related to the function of the specified amino acid sequence, or that would not be encoded by the nucleotides that flank the naturally occurring nucleic acid sequence encoding the specified amino acid sequence as it occurs in the gene, if such nucleotides in the naturally occurring sequence were translated using standard codon usage for the organism from which the given amino acid sequence is derived. Similarly, the phrase "consisting essentially of", when used with reference to a nucleic acid sequence herein, refers to a nucleic acid sequence encoding a specified amino acid sequence that can be flanked by from at least one, and up to as many as about 60, additional heterologous nucleotides at each of the 5' and/or the 3' end of the nucleic acid sequence encoding the specified amino acid sequence. The heterologous nucleotides are not naturally found (i.e., not found in nature, in vivo) flanking the nucleic acid sequence encoding the specified amino acid sequence as it occurs in the natural gene or do not encode a protein that imparts any additional function to the protein or changes the function of the protein having the specified amino acid sequence.

FAS proteins as described herein can be isolated from a various microorganisms including members of the order Thraustochytriales. For example, preferred microorganisms from which a FAS protein of the present invention may be derived include microorganisms from a genus including, but not limited to: *Thraustochytrium, Labyrinthuloides, Japonochytrium*, and *Schizochytrium*. Preferred species within these genera include, but are not limited to: any *Schizochytrium* species, including *Schizochytrium aggregatum, Schizochytrium limacinum, Schizochytrium minutum*; any *Thraustochytrium* species (including former *Ulkenia* species such as *U. visurgensis, U. amoeboida, U. sarkariana, U. profunda, U. radiata, U. minuta* and *Ulkenia* sp. BP-5601), and including *Thraustochytrium striatum, Thraustochytrium aureum, Thraustochytrium roseum*; and any *Japonochytrium* species. Particularly preferred strains of Thraustochytriales include, but are not limited to: *Schizochytrium* sp. (S31) (ATCC 20888); *Schizochytrium* sp. (S8)(ATCC 20889); *Schizochytrium* sp. (LC-RM)(ATCC 18915); *Schizochytrium* sp. (SR21); *Schizochytrium aggregatum* (Goldstein et Belsky)(ATCC 28209); *Schizochytrium limacinum* (Honda et Yokochi)(IFO 32693); *Thraustochytrium* sp. (23B)(ATCC 20891); *Thraustochytrium striatum* (Schneider)(ATCC 24473); *Thraustochytrium aureum* (Goldstein)(ATCC 34304); *Thraustochytrium roseum* (Goldstein)(ATCC 28210); and *Japonochytrium* sp. (L1)(ATCC 28207).

According to the present invention, the terms/phrases "Thraustochytrid", "Thraustochytriales microorganism" and "microorganism of the order Thraustochytriales" can be used interchangeably and refer to any members of the order Thraustochytriales, which includes both the family Thraustochytriaceae and the family Labyrinthulaceae. The terms "Labyrinthulid" and "Labyrinthulaceae" are used herein to specifically refer to members of the family Labyrinthulaceae. To specifically reference Thraustochytrids that are members of the family Thraustochytriaceae, the term "Thraustochytriaceae" is used herein. Thus, for the present invention, members of the Labyrinthulids are considered to be included in the Thraustochytrids.

Developments have resulted in frequent revision of the taxonomy of the Thraustochytrids. Taxonomic theorists generally place Thraustochytrids with the algae or algae-like protists. However, because of taxonomic uncertainty, it would be best for the purposes of the present invention to consider the strains described in the present invention as Thraustochytrids to include the following organisms: Order: Thraustochytriales; Family: Thraustochytriaceae (Genera: *Thraustochytrium, Schizochytrium, Japonochytrium, Aplanochytrium,* or *Elina*) or Labyrinthulaceae (Genera *Labyrinthula, Labyrinthuloides,* or *Labyrinthomyxa*). Also, the following genera are sometimes included in either family Thraustochytriaceae or Labyrinthulaceae: *Althornia, Corallochytrium, Diplophyrys,* and *Pyrrhosorus*), and for the purposes of this invention are encompassed by reference to a Thraustochytrid or a member of the order Thraustochytriales. It is recognized that at the time of this invention, revision in the taxonomy of Thraustochytrids places the genus *Labyrinthuloides* in the family of Labyrinthulaceae and confirms the placement of the two families Thraustochytriaceae and Labyrinthulaceae within the Stramenopile lineage. It is noted that the Labyrinthulaceae are sometimes commonly called labyrinthulids or labyrinthula, or labyrinthuloides and the Thraustochytriaceae are commonly called thraustochytrids, although, as discussed above, for the purposes of clarity of this invention, reference to Thraustochytrids encompasses any member of the order Thraustochytriales and/or includes members of both Thraustochytriaceae and Labyrinthulaceae. Recent taxonomic changes are summarized below.

Strains of certain unicellular microorganisms disclosed herein are members of the order Thraustochytriales. Thraustochytrids are marine eukaryotes with an evolving taxonomic history. Problems with the taxonomic placement of the Thraustochytrids have been reviewed by Moss (in "*The Biology of Marine Fungi*", Cambridge University Press p. 105 (1986)), Bahnweb and Jackle (ibid. p. 131) and Chamberlain and Moss (BioSystems 21:341 (1988)).

For convenience purposes, the Thraustochytrids were first placed by taxonomists with other colorless zoosporic eukaryotes in the Phycomycetes (algae-like fungi). The name Phycomycetes, however, was eventually dropped from taxonomic status, and the Thraustochytrids were retained in the Oomycetes (the biflagellate zoosporic fungi). It was initially assumed that the Oomycetes were related to the heterokont algae, and eventually a wide range of ultrastructural and biochemical studies, summarized by Barr (Barr. Biosystems 14:359 (1981)) supported this assumption. The Oomycetes were in fact accepted by Leedale (Leedale. Taxon 23:261 (1974)) and other phycologists as part of the heterokont algae. However, as a matter of convenience resulting from their heterotrophic nature, the Oomycetes and Thraustochytrids have been largely studied by mycologists (scientists who study fungi) rather than phycologists (scientists who study algae).

From another taxonomic perspective, evolutionary biologists have developed two general schools of thought as to how eukaryotes evolved. One theory proposes an exogenous origin of membrane-bound organelles through a series of endosymbioses (Margulis, 1970, Origin of Eukaryotic Cells. Yale University Press, New Haven); e.g., mitochondria were derived from bacterial endosymbionts, chloroplasts from cyanophytes, and flagella from spirochaetes. The other theory suggests a gradual evolution of the membrane-bound organelles from the non-membrane-bounded systems of the prokaryote ancestor via an autogenous process (Cavalier-Smith, 1975, Nature (Lond.) 256:462-468). Both groups of evolutionary biologists however, have removed the Oomycetes and Thraustochytrids from the fungi and place them either with the chromophyte algae in the kingdom Chromophyta (Cavalier-Smith BioSystems 14:461 (1981)) (this kingdom has been more recently expanded to include other protists and members of this kingdom are now called Stramenopiles) or with all algae in the kingdom Protoctista (Margulis and Sagen. Biosystems 18:141 (1985)).

With the development of electron microscopy, studies on the ultrastructure of the zoospores of two genera of Thraustochytrids, *Thraustochytrium* and *Schizochytrium*, (Perkins, 1976, pp. 279-312 in "Recent Advances in Aquatic Mycology" (ed. E. B. G. Jones), John Wiley & Sons, New York; Kazama. Can. J. Bot. 58:2434 (1980); Barr, 1981, Biosystems 14:359-370) have provided good evidence that the Thraustochytriaceae are only distantly related to the Oomycetes. Additionally, genetic data representing a correspondence analysis (a form of multivariate statistics) of 5-S ribosomal RNA sequences indicate that Thraustochytriales are clearly a unique group of eukaryotes, completely separate from the fungi, and most closely related to the red and brown algae, and to members of the Oomycetes (Mannella et al. Mol. Evol. 24:228 (1987)). Most taxonomists have agreed to remove the Thraustochytrids from the Oomycetes (Bartnicki-Garcia. p. 389 in "Evolutionary Biology of the Fungi" (eds. Rayner, A. D. M., Brasier, C. M. & Moore, D.), Cambridge University Press, Cambridge).

In summary, employing the taxonomic system of Cavalier-Smith (Cavalier-Smith. BioSystems 14:461 (1981); Cavalier-Smith. Microbiol Rev. 57:953 (1993)), the Thraustochytrids are classified with the chromophyte algae in the kingdom Chromophyta (Stramenopiles). This taxonomic placement has been more recently reaffirmed by Cavalier-Smith et al. using the 18s rRNA signatures of the Heterokonta to demonstrate that Thraustochytrids are chromists not Fungi (Cavalier-Smith et al. Phil. Tran. Roy. Soc. London Series Bio-Sciences 346:387 (1994)). This places the Thraustochytrids in a completely different kingdom from the fungi, which are all placed in the kingdom Eufungi.

Currently, there are 71 distinct groups of eukaryotic organisms (Patterson. Am. Nat. 154:S96 (1999)) and within these groups four major lineages have been identified with some confidence: (1) Alveolates, (2) Stramenopiles, (3) a Land Plant-green algae-Rhodophyte_Glaucophyte ("plant") clade and (4) an Opisthokont clade (Fungi and Animals). Formerly these four major lineages would have been labeled Kingdoms but use of the "kingdom" concept is no longer considered useful by some researchers.

As noted by Armstrong, Stramenopile refers to three-parted tubular hairs, and most members of this lineage have flagella bearing such hairs. Motile cells of the Stramenopiles (unicellular organisms, sperm, zoospores) are asymmetrical having two laterally inserted flagella, one long, bearing three-parted tubular hairs that reverse the thrust of the flagellum, and one short and smooth. Formerly, when the group was less broad, the Stramenopiles were called Kingdom Chromista or the heterokont (=different flagella) algae because those groups consisted of the Brown Algae or Phaeophytes, along with the yellow-green Algae, Golden-brown Algae, Eustigmatophytes and Diatoms. Subsequently some heterotrophic, fungal-like organisms, the water molds, and labyrinthulids (slime net amoebas), were found to possess similar motile cells, so a group name referring to photosynthetic pigments or algae became inappropriate. Currently, two of the families within the Stramenopile lineage are the Labyrinthulaceae and the Thraustochytriaceae. Historically, there have been numerous classification strategies for these unique microorganisms and they are often classified under the same order (i.e., Thraustochytriales). Relationships of the members in these groups are still developing. Porter and Leander have developed data based on 18S small subunit ribosomal DNA indicating the thraustochytrid-labyrinthulid clade in monophyletic. However, the clade is supported by two branches; the first contains three species of *Thraustochytrium* and *Ulkenia profunda*, and the second includes three species of *Labyrinthula*, two species of *Labyrinthuloides* and *Schizochytrium aggregatum*.

The taxonomic placement of the Thraustochytrids as used in the present invention is therefore summarized below:

Kingdom: Chromophyta (Stramenopiles)

Phylum: Heterokonta

Order: Thraustochytriales (Thraustochytrids)

Family: Thraustochytriaceae or Labyrinthulaceae

Genera: *Thraustochytrium, Schizochytrium, Japonochytrium, Aplanochytrium, Elina, Labyrinthula, Labyrinthuloides,* or *Labyrinthulomyxa*

Some early taxonomists separated a few original members of the genus *Thraustochytrium* (those with an amoeboid life stage) into a separate genus called *Ulkenia*. However it is now known that most, if not all, Thraustochytrids (including *Thraustochytrium* and *Schizochytrium*), exhibit amoeboid stages and as such, *Ulkenia* is not considered by some to be a valid genus. As used herein, the genus *Thraustochytrium* will include *Ulkenia*.

Despite the uncertainty of taxonomic placement within higher classifications of Phylum and Kingdom, the Thraustochytrids remain a distinctive and characteristic grouping whose members remain classifiable within the order Thraustochytriales.

Further embodiments of the present invention include nucleic acid molecules that encode a FAS protein. An isolated nucleic acid molecule of the present invention includes a nucleic acid molecule comprising a nucleic acid sequence encoding any of the isolated FAS proteins, including a FAS homologue or fragment, described above.

In one embodiment, such nucleic acid molecules include isolated nucleic acid molecules that hybridize under moderate stringency conditions, and even more preferably under high stringency conditions, and even more preferably under very high stringency conditions with the complement of a nucleic acid sequence encoding a naturally occurring FAS protein (i.e., including naturally occurring allelic variants encoding a FAS protein). Preferably, an isolated nucleic acid molecule encoding a FAS protein of the present invention comprises a nucleic acid sequence that hybridizes under moderate, high, or very high stringency conditions to the complement of a nucleic acid sequence that encodes any of the proteins described above. In one embodiment, an isolated nucleic acid molecule comprises a nucleic acid sequence that hybridizes under moderate, high or very high stringency conditions to the complement of a nucleic acid sequence represented by SEQ ID NO:1. Such conditions have been described in detail above.

In accordance with the present invention, an isolated nucleic acid molecule is a nucleic acid molecule that has been removed from its natural milieu (i.e., that has been subject to human manipulation) and can include DNA, RNA, or derivatives of either DNA or RNA, including cDNA. As such, "isolated" does not reflect the extent to which the nucleic acid molecule has been purified. An isolated FAS nucleic acid molecule of the present invention can be isolated from its natural source or produced using recombinant DNA technology (e.g., polymerase chain reaction (PCR) amplification, cloning) or chemical synthesis. Isolated FAS nucleic acid molecules can include, for example, FAS genes, natural allelic variants of FAS genes, FAS coding regions or portions thereof, and FAS coding and/or regulatory regions modified by nucleotide insertions, deletions, substitutions, and/or inversions in a manner such that the modifications do not substantially interfere with the nucleic acid molecule's ability to encode a FAS protein of the present invention or to form stable hybrids under stringent conditions with natural gene isolates. An isolated FAS nucleic acid molecule can include degeneracies. As used herein, nucleotide degeneracies refers to the phenomenon that one amino acid can be encoded by different nucleotide codons. Thus, the nucleic acid sequence of a nucleic acid molecule that encodes a FAS protein of the present invention can vary due to degeneracies. It is noted that an isolated FAS nucleic acid molecule of the present invention is not required to encode a protein having FAS activity. A FAS nucleic acid molecule can encode a truncated, mutated or inactive protein, for example. Such nucleic acid molecules and the proteins encoded by such nucleic acid molecules are useful in as probes and primers for the identification of other FAS proteins.

According to the present invention, reference to a FAS gene includes all nucleic acid sequences related to a natural (i.e. wild-type) FAS gene, such as regulatory regions that control production of the FAS encoded by that gene (such as, but not limited to, transcription, translation or post-translation control regions) as well as the coding region itself. The present inventors provide herein the 5' untranslated region of the FAS gene of the present invention (represented herein by SEQ ID NO:4), as well as the 3' untranslated region (represented herein by SEQ ID NO:3). The use of these regions of the FAS gene to regulate the expression and/or biological activity of a FAS-encoding nucleic acid molecule, such as an endogenous FAS gene, or to regulate the expression or activity of a heterologous nucleic acid molecule (i.e., a molecule encoding a different protein) is encompassed by the present invention. In addition, the regulation of the expression or activity of a FAS gene or protein according to the present invention also encompasses the use of any regulatory sequence or protein, including heterologous regulatory sequences and proteins (i.e., those that are not naturally associated with the FAS gene or protein) to regulate the expression and/or biological activity of FAS. Such uses will be described below.

In another embodiment, a FAS gene can be a naturally occurring allelic variant that includes a similar but not identical sequence to the nucleic acid sequence encoding a given FAS protein. Allelic variants have been previously described above. The phrases "nucleic acid molecule" and "gene" can be used interchangeably when the nucleic acid molecule comprises a gene as described above.

A FAS nucleic acid molecule homologue (i.e., encoding a FAS homologue) can be produced using a number of methods known to those skilled in the art (see, for example, Sambrook et al.). For example, nucleic acid molecules can be modified using a variety of techniques including, but not limited to, by classic mutagenesis and recombinant DNA techniques (e.g., site-directed mutagenesis, chemical treatment, restriction enzyme cleavage, ligation of nucleic acid fragments and/or PCR amplification), or synthesis of oligonucleotide mixtures and ligation of mixture groups to "build" a mixture of nucleic acid molecules and combinations thereof. Another method for modifying a recombinant nucleic acid molecule encoding a FAS is gene shuffling (i.e., molecular breeding) (See, for example, U.S. Pat. No. 5,605,793 to Stemmer; Minshull and Stemmer; 1999, *Curr. Opin. Chem. Biol.* 3:284-290; Stemmer, 1994, *P.N.A.S. USA* 91:10747-10751, all of which are incorporated herein by reference in their entirety). This technique can be used to efficiently introduce multiple simultaneous changes in the FAS activity. Nucleic acid molecule homologues can be selected by hybridization with a FAS gene or by screening the function of a protein encoded by a nucleic acid molecule (e.g., enzymatic activity).

One embodiment of the present invention relates to an oligonucleotide, comprising at least 12 contiguous nucleotides of SEQ ID NO:1, and a nucleic acid sequence fully complementary thereto. The minimal size of a nucleic acid molecule that is used as an oligonucleotide primer or as a probe is typically at least about 12 to about 15 nucleotides in length if the nucleic acid molecules are GC-rich and at least about 15 to about 18 bases in length if they are AT-rich. There is no limit, other than a practical limit, on the maximal size of an oligonucleotide probe or primer of the present invention, in that the probe or primer can include any portion of a FAS gene of the invention that is suitable for the intended use, with probes typically being larger than primers. As such, an oligonucleotide of the invention can include any length fragment between about 12 and about 12,408 nucleotides or even larger probes, in whole integers (e.g., 12, 13, 14, 15, 16 . . . 12,407, 12,408).

One embodiment of the present invention includes a recombinant nucleic acid molecule, which includes at least one isolated nucleic acid molecule of the present invention inserted into any nucleic acid vector (e.g., a recombinant vector) which is suitable for cloning, sequencing, and/or otherwise manipulating the nucleic acid molecule, such as expressing and/or delivering the nucleic acid molecule into a host cell to form a recombinant cell. Such a vector contains heterologous nucleic acid sequences, that is nucleic acid sequences that are not naturally found adjacent to nucleic acid molecules of the present invention, although the vector can also contain regulatory nucleic acid sequences (e.g., promoters, untranslated regions) which are naturally found adjacent to nucleic acid molecules of the present invention (discussed in detail below). The vector can be either RNA or DNA, either prokaryotic or eukaryotic, and typically is a virus or a plasmid. The vector can be maintained as an extrachromosomal element (e.g., a plasmid) or it can be integrated into the chromosome. The entire vector can remain in place within a host cell, or under certain conditions, the plasmid DNA can be deleted, leaving behind the nucleic acid molecule of the present invention. The integrated nucleic acid molecule can be under chromosomal promoter control, under native or plasmid promoter control, or under a combination of several promoter controls. Single or multiple copies of the nucleic acid molecule can be integrated into the chromosome. The vector can be designed for tissue-specific expression in the host cell, such as by using tissue-specific promoters. Several recombinant nucleic acid molecules useful in the present invention, including several recombinant vectors, are described in detail in the Examples.

Typically, a recombinant molecule includes a nucleic acid molecule of the present invention operatively linked to one or more transcription control sequences (e.g., promoters, operators, repressors, enhancers, terminators). As used herein, the phrase "recombinant molecule" or "recombinant nucleic acid molecule" primarily refers to a nucleic acid molecule or nucleic acid sequence operatively linked to a transcription control sequence, but can be used interchangeably with the phrase "nucleic acid molecule", when such nucleic acid molecule is a recombinant molecule as discussed herein. According to the present invention, the phrase "operatively linked" refers to linking a nucleic acid molecule to a transcription control sequence in a manner such that the molecule is able to be expressed when transformed (i.e., transformed, transduced, transfected, or conjugated) into a host cell. Transcription control sequences are sequences which control the initiation, elongation, or termination of transcription. Particularly important transcription control sequences are those which control transcription initiation, such as promoter, enhancer, operator and repressor sequences. Suitable transcription control sequences include any transcription control sequence that can function in at least one of the recombinant cells useful for expressing a FAS protein of the present invention. A variety of such transcription control sequences are known to those skilled in the art. Preferred transcription control sequences include those which function in Thraustochytriales microorganisms, bacterial, fungal (e.g., yeast), or plant cells. Other preferred transcription control sequences are for plants and include those that promote gene expression in specific tissues (e.g., leaves, stems, roots, flowers, seeds) and can be referred to herein as tissue-specific transcription control sequences. Such sequences are well known in the art.

In one embodiment of the invention, a suitable transcription control sequence includes the regulatory sequences that are naturally found in the FAS gene of the present invention. For example, regulatory sequences of a *Schizochytrium* FAS, which include a FAS promoter, are found in nucleotides represented herein by SEQ ID NO:3 (3' untranslated region) or in nucleotides represented herein by SEQ ID NO:4 (5' untranslated region). In another embodiment, any regulatory sequence can be used which increases (enhances, upregulates), allows/maintains or decreases (attenuates, downregulates, reduces) the expression and/or biological activity of an endogenous and/or recombinant FAS gene or protein of the present invention. Regulatory sequences, including promoter sequences, for a variety of host organisms are known in the art and all are encompassed for use in the present invention.

Recombinant molecules of the present invention, which can be either DNA or RNA, can also contain additional regulatory sequences, such as transcription regulatory sequences, translation regulatory sequences, origins of replication, and other regulatory sequences that are compatible with the recombinant cell. In one embodiment, a recombinant molecule of the present invention, including those which are integrated into the host cell chromosome, also contains signal (targeting) (i.e., signal segment nucleic acid sequences) to enable an expressed FAS to be secreted from the cell that produces the protein or targeted to a particular organelle or membrane. For example, in one embodiment, suitable signal segments include a signal segment that is naturally associated with a FAS of the present invention or any heterologous signal segment capable of directing the secretion of a FAS protein according to the present invention. In another embodiment, a recombinant molecule of the present invention comprises a signal sequence to enable an expressed FAS protein to be delivered to and inserted into the membrane of a host cell. In another embodiment, a recombinant molecule of the present invention comprises a signal sequence which specifically targets the delivery of a FAS to specific sub-cellular organelles or compartments, such as the endoplasmic reticulum, the chloroplast, the chromoplast, other plastids, or the cytoplasm.

One or more recombinant molecules of the present invention can be used to produce an encoded product (e.g., a FAS protein) of the present invention. In one embodiment, an encoded product is produced by expressing a nucleic acid molecule as described herein under conditions effective to produce the protein. A preferred method to produce an encoded protein is by transforming a host cell with one or more recombinant molecules to form a recombinant cell. Suitable host cells to transform include, but are not limited to, any microalgal cell, including a Thraustochytriales microorganism, or any bacterial cell, fungal (e.g., yeast) cell, other microbial cell, or plant cell that can be transformed. Host cells can be either untransformed cells or cells that are already transformed with at least one nucleic acid molecule.

Preferred host cells for use in the present invention include any microorganism cell or plant cell which is suitable for expression of a FAS protein of the present invention, including, but not limited to: (1) plants, including, but not limited to, crop plants (e.g., canola—*Brassica napus*, rice, corn, flax, safflower, soy, sunflower, rapeseed, linseed); (2) fungi, including, but not limited to, *Phycomyces* sp., *Neurospora* sp., *Mucor* sp. (e.g., *Mucor circinelloides*), *Blakeslea* sp., *Mortierella* sp. (e.g., *Mortierella alpina*), *Rhodotorula* sp., *Lipomyces* sp. (e.g., *Lipomyces starkeyi*), *Cryptococcus* sp. (e.g., *Cryptococcus curvatus*, aka *Apiotricum curvatum*), *Cunninghamella* sp. (e.g., *Cunninghamella echinulata*), *Yarrowia* sp. (e.g., *Yarrowia lipolytica*) and yeast (e.g., *Saccharomyces* sp. (e.g., *Saccharomyces cerevisiae*), *Phaffia rhodozyma*, *Xanthophyllomyces dendrohous*, *Candida* sp. (e.g., *Candida utilus*); (3) algae, including but not limited to, green algae (e.g., *Haematococcus pluvialus*, *Chlorococcum*, *Spongiococcum*, *Neospongiococcum*, *Dunaliella*), *Crypthecodinium cohnii*, *Porphyridium cruentum*, *Phaeodactylum tricornicum*, *Nannochloropsis oculata*, *Isochrysis galbana*, *Chlorella* sp.; (4) bacteria, including, but not limited to, blue-green (e.g., *Spirulina*, *Synechococcus*, *Synechocystis*), *Escherichia coli*, *Flavobacterium*, *Paracoccus*, *Erwinia*, *Agrobacterium*, *Rhodococcus*, *Mycobacterium*, *Streptomyces*, *Thodococcus*, *Nocardia*, *Pseudomonas*; and (5) members of the order, Thraustochytriales, including but not limited to: *Thraustochytrium* sp. (e.g., including former Ulkenia species such as *U. visurgensis*, *U. amoeboida*, *U. sarkariana*, *U. profunda*, *U. radiata*, *U. minuta* and *Ulkenia* sp. BP-5601, and including *Thraustochytrium striatum*, *Thraustochytrium aureum*, and *Thraustochytrium roseum*); *Labyrinthuloides*, *Japonochytrium* (e.g., *Japonochytrium* sp.), and *Schizochytrium* (e.g., *Schizochytrium* sp., *Schizochytrium aggregatum*, *Schizochytrium limacinum*, *Schizochytrium minutum*).

According to the present invention, the term "transformed" or "transformation" is used to refer to any method by which an exogenous nucleic acid molecule (i.e., a recombinant nucleic acid molecule) can be inserted into the cell. In microbial systems, the term "transformation" is used to describe an inherited change due to the acquisition of exogenous nucleic acids by the microorganism and can be essentially synonymous with the term "transfection", which is more commonly used in reference to the similar process in animal cells. The term "transformation" is preferably used herein to refer to the introduction of nucleic acid molecules into microbial cells, such as bacteria and yeast, or into plant cells. Therefore, transformation techniques include, but are not limited to, transfection, electroporation, microinjection, lipofection, biolistic methods (particle bombardment), adsorption, *Agrobacterium*-mediated transformation, infection and protoplast fusion. Methods of transforming prokaryotic and eukaryotic host cells are well known in the art. See, e.g., Maniatis et al., *Molecular Cloning: A Laboratory Manual*, Cold Spring Harbor, N.Y. (1982), Sambrook et al., *Molecular Cloning: A Laboratory Manual*, Cold Spring Harbor, N.Y. (1989), incorporated herein by reference in its entirety. A preferred method for transforming members of the order Thraustochytriales is described in U.S. patent application Ser. No. 10/124,807, filed Apr. 16, 2002, incorporated by reference in its entirety.

Numerous methods for plant transformation have been developed, including biological and physical transformation protocols. See, for example, Miki et al., "Procedures for Introducing Foreign DNA into Plants" in *Methods in Plant Molecular Biology and Biotechnology*, Glick, B. R. and Thompson, J. E. Eds. (CRC Press, Inc., Boca Raton, 1993) pp. 67-88. In addition, vectors and in vitro culture methods for plant cell or tissue transformation and regeneration of plants are available. See, for example, Gruber et al., "Vectors for Plant Transformation" in *Methods in Plant Molecular Biology and Biotechnology*, Glick, B. R. and Thompson, J. E. Eds. (CRC Press, Inc., Boca Raton, 1993) pp. 89-119.

The most widely utilized method for introducing an expression vector into plants is based on the natural transformation system of *Agrobacterium*. See, for example, Horsch et al., *Science* 227:1229 (1985). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., *Crit. Rev. Plant. Sci.* 10:1 (1991). Descriptions of *Agrobacterium* vector systems and methods for *Agrobacterium*-mediated gene transfer are provided by numerous references, including Gruber et al., supra, Miki et al., supra, Moloney et al., *Plant Cell Reports* 8:238 (1989), and U.S. Pat. Nos. 4,940,838 and 5,464,763, each of which is incorporated herein by reference in its entirety.

A generally applicable method of plant transformation is microprojectile-mediated transformation wherein DNA is carried on the surface of microprojectiles. The expression vector is introduced into plant tissues with a biolistic device that accelerates the microprojectiles to speeds sufficient to penetrate plant cell walls and membranes. Sanford et al., *Part. Sci. Technol.* 5:27 (1987), Sanford, J. C., *Trends Biotech.* 6:299 (1988), Sanford, J. C., *Physiol. Plant* 79:206 (1990), Klein et al., *Biotechnology* 10:268 (1992), each of which is incorporated herein by reference in its entirety.

Another method for physical delivery of DNA to plants is sonication of target cells. Zhang et al., *Bio/Technology* 9:996 (1991). Alternatively, liposome or spheroplast fusion have been used to introduce expression vectors into plants. Deshayes et al., *EMBO J.*, 4:2731 (1985), Christou et al., *Proc Natl. Acad. Sci. USA* 84:3962 (1987), each of which is incorporated herein by reference in its entirety. Direct uptake of DNA into protoplasts using $CaCl_2$ precipitation, polyvinyl alcohol or poly-L-ornithine have also been reported. Hain et al., *Mol. Gen. Genet.* 199:161 (1985) and Draper et al., *Plant Cell Physiol.* 23:451 (1982), each of which is incorporated herein by reference in its entirety. Electroporation of protoplasts and whole cells and tissues have also been described. Donn et al., In Abstracts of VIIth International Congress on Plant Cell and Tissue Culture IAPTC, A2-38, p. 53 (1990); D'Halluin et al., *Plant Cell* 4:1495-1505 (1992) and Spencer et al., *Plant Mol. Biol.* 24:51-61 (1994), each of which is incorporated herein by reference in its entirety.

In one embodiment, an isolated FAS protein of the present invention is produced by culturing a cell that expresses the protein under conditions effective to produce the protein, and recovering the protein. A preferred cell to culture is a recombinant cell of the present invention. Effective culture conditions include, but are not limited to, effective media, bioreactor, temperature, pH and oxygen conditions that permit protein production. An effective medium refers to any medium in which a cell is cultured to produce a FAS protein of the present invention. Such medium typically comprises an aqueous medium having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes, and Petri plates. Culturing can be carried out at a temperature, pH and oxygen content appropriate for a recombinant cell. Such culturing conditions are within the expertise of one of ordinary skill in the art.

Depending on the vector and host system used for production, resultant proteins of the present invention may either remain within the recombinant host cell; be secreted into the culture medium; be secreted into a space between two cellular membranes, such as the periplasmic space in *E. coli*; or be retained on the outer surface of a cell membrane. The phrase "recovering the protein" refers to collecting the whole culture medium containing the protein and need not imply additional steps of separation or purification. Proteins of the present invention can be purified, if desired, using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization. If proteins of the present invention are purified, they are preferably retrieved in "substantially pure" form. As used herein, "substantially pure" refers to a purity that allows for the effective use of the protein as a biocatalyst or other reagent.

To produce significantly high yields of short chain fatty acids by the methods of the present invention, a microorganism or plant (or part of a plant, e.g., seeds, pollen, embryos, flowers, fruits, shoots, leaves, roots, stems, explants, etc.) can be genetically modified to increase the action of the FAS protein of the present invention, and preferably, to enhance production of the FAS protein, and thereby, a short chain fatty acid endproduct.

In a preferred embodiment of the invention, a microorganism that contains an endogenous FAS protein of the invention (e.g., *Schizochytrium*) is genetically modified to increase or reduce the expression and activity of the FAS protein. Without being bound by theory, the present inventors believe that attenuation of the expression or activity of the endogenous FAS protein in Thraustochytrids such as *Schizochytrium* will increase the accumulation of the highly desirable polyunsaturated fatty acids (PUFAs) by the organism, the synthesis of which proceeds using the PUFA polyketide synthase (PKS) system, which shares some of the same substrates with the FAS system (this PUFA PKS system is described in detail in PCT Publication No. WO 02/083870, published Oct. 24, 2002, which is incorporated herein by reference in its entirety). Therefore, decreasing the expression or activity of the FAS in the microorganism will increase the production of PUFAs.

As used herein, a genetically modified microorganism, such as a genetically modified bacterium, protist, microalga, fungus, or other microbe, and particularly, any member of the genera of the order Thraustochytriales (e.g., a *Thraustochytrid*) described herein (e.g., *Schizochytrium, Thraustochytrium, Japonochytrium, Labyrinthuloides*), has a genome which is modified (i.e., mutated or changed) from its normal (i.e., wild-type or naturally occurring) form such that the desired result is achieved (i.e., increased or modified FAS expression and/or activity, production of a desired product using the FAS protein, or decreased or modified FAS expression and/or activity). Genetic modification of a microorganism can be accomplished using classical strain development and/or molecular genetic techniques. Such techniques are generally disclosed for microorganisms, for example, in Sambrook et al., 1989, supra, incorporated by reference herein in its entirety. A genetically modified microorganism can include a microorganism in which nucleic acid molecules have been inserted, deleted or modified (i.e., mutated; e.g., by insertion, deletion, substitution, and/or inversion of nucleotides), in such a manner that such modifications provide the desired effect within the microorganism.

Preferred microorganism host cells to modify according to the present invention include, but are not limited to, any bacteria, protist, microalga, fungus, or protozoa. In one aspect, preferred microorganisms to genetically modify include, but are not limited to, any microorganism of the order Thraustochytriales. Particularly preferred host cells for use in the present invention could include microorganisms from a genus including, but not limited to: *Thraustochytrium, Labyrinthuloides, Japonochytrium*, and *Schizochytrium*. Preferred species within these genera include, but are not limited to: any *Schizochytrium* species, including *Schizochytrium aggregatum, Schizochytrium limacinum, Schizochytrium minutum*; any *Thraustochytrium* species (including former *Ulkenia* species such as *U. visurgensis, U. amoeboida, U. sarkariana, U. profunda, U. radiata, U. minuta* and *Ulkenia* sp. BP-5601), and including *Thraustochytrium striatum, Thraustochytrium aureum, Thraustochytrium roseum*; and any *Japonochytrium* species. Particularly preferred strains of Thraustochytriales include, but are not limited to: *Schizochytrium* sp. (S31) (ATCC 20888); *Schizochytrium* sp. (S8)(ATCC 20889); *Schizochytrium* sp. (LC-RM)(ATCC 18915); *Schizochytrium* sp. (SR21); *Schizochytrium* aggregatum (Goldstein et Belsky)(ATCC 28209); *Schizochytrium limacinum* (Honda et Yokochi)(IFO 32693); *Thraustochytrium* sp. (23B)(ATCC 20891); *Thraustochytrium striatum* (Schneider)(ATCC 24473); *Thraustochytrium aureum* (Goldstein)(ATCC 34304); *Thraustochytrium roseum* (Goldstein)(ATCC 28210); and *Japonochytrium* sp. (L1)(ATCC 28207). Other examples of suitable host microorganisms for genetic modification include, but are not limited to, yeast including *Saccharomyces cerevisiae, Saccharomyces carlsbergensis*, or other yeast such as *Candida, Kluyveromyces*, or other fungi, for example, filamentous fungi such as *Aspergillus, Neurospora, Penicillium*, etc. Bacterial cells also may be used as hosts. This includes *Escherichia coli*, which can be useful in fermentation processes. Alternatively, a host such as a *Lactobacillus* species or *Bacillus* species can be used as a host.

As used herein, a genetically modified plant can include any genetically modified plant including higher plants and particularly, any consumable plants or plants useful for producing a desired product of the present invention (e.g., short chain fatty acids or any other lipid product). Such a genetically modified plant has a genome which is modified (i.e., mutated or changed) from its normal (i.e., wild-type or naturally occurring) form such that the desired result is achieved (i.e., increased or modified FAS expression and/or activity and/or production of a desired product using the FAS protein). Genetic modification of a plant can be accomplished using classical strain development and/or molecular genetic techniques. Methods for producing a transgenic plant, wherein a recombinant nucleic acid molecule encoding a desired amino acid sequence is incorporated into the genome of the plant, are known in the art and have been described briefly above. A preferred plant to genetically modify according to the present invention is preferably a plant suitable for consumption by animals, including humans.

Preferred plants to genetically modify according to the present invention (i.e., plant host cells) include, but are not limited to any higher plants, and particularly consumable plants, including crop plants and especially plants used for their oils. Such plants can include, for example: canola, soybeans, rapeseed, linseed, corn, safflowers, flax, sunflowers, tobacco, rice, tomatoes and carrots. Other preferred plants include those plants that are known to produce compounds used as pharmaceutical agents, flavoring agents, neutraceutical agents, functional food ingredients or cosmetically active agents or plants that are genetically engineered to produce these compounds/agents.

According to the present invention, a genetically modified microorganism or plant includes a microorganism or plant that has been modified using recombinant technology. As used herein, genetic modifications that result in a decrease in gene expression, in the function of the gene, or in the function of the gene product (i.e., the protein encoded by the gene) can be referred to as inactivation (complete or partial), attenuation, deletion, interruption, blockage or down-regulation of a gene. For example, a genetic modification in a gene which results in a decrease in the function of the protein encoded by such gene, can be the result of a complete deletion of the gene (i.e., the gene does not exist, and therefore the protein does not exist), a mutation in the gene which results in incomplete or no translation of the protein (e.g., the protein is not expressed), or a mutation in the gene or introduction of a regulatory sequence or protein into the host which decreases, attenuates or abolishes the expression and/or the natural function of the protein (e.g., a protein is expressed which has decreased or no enzymatic activity or action). In the present invention, genetic modifications that decrease the expression or activity of a FAS are preferably not complete inactivations, as such mutations are lethal in microorganisms. Preferably, such modifications reduce or attenuate, but do not entirely delete, the expression or function of a FAS protein. Genetic modifications that result in an increase in gene expression or function can be referred to as amplification, overproduction, overexpression, activation, enhancement, addition, or up-regulation of a gene.

In one embodiment of the present invention, a genetic modification of a microorganism or plant increases or decreases the expression and/or activity of a FAS protein of the present invention. Such a genetic modification includes any type of modification and specifically includes modifications made by recombinant technology and/or by classical mutagenesis. It should be noted that reference to increasing the action (activity) of FAS refers to any genetic modification in the microorganism or plant in question and/or in the recombinant nucleic acids containing the FAS-encoding DNA with which the organism is transformed that results in increased functionality of the protein and can include higher activity of the protein (e.g., specific activity or in vivo enzymatic activity), reduced inhibition or degradation of the protein, and overexpression of the protein. For example, gene copy number can be increased, expression levels can be increased by use of a promoter that gives higher levels of expression than that of the native promoter, or a gene can be altered by genetic engineering or classical mutagenesis to increase the action of an enzyme. In one aspect, FAS activity or expression can be modified by modifying a nucleic acid or protein that interacts with a FAS gene or protein and normally modulates the expression or activity of the FAS gene or protein. Such a modification can be achieved by recombinant or classical mutational techniques.

Similarly, reference to decreasing the action (activity) of a FAS protein refers to any genetic modification in the microorganism or plant in question and/or in the recombinant nucleic acids containing the FAS-encoding DNA (including FAS regulatory regions or inhibitors thereof) with which the organism is transformed that results in decreased functionality of the enzymes and includes decreased activity of the enzymes (e.g., specific activity), increased inhibition or degradation of the enzymes and a reduction or elimination of expression of the enzyme. For example, the action of FAS of the present invention can be decreased by blocking or reducing the production of the protein, "knocking out" all or a portion of the gene encoding the protein, reducing FAS activity, or inhibiting the activity of FAS (any one, two or more of the biological activities of a FAS of the invention). Blocking or reducing the production of an enzyme can include placing the gene encoding the protein under the control of a heterologous promoter that requires the presence of an inducing compound in the growth medium. By establishing conditions such that the inducer becomes depleted from the medium, the expression of the gene encoding the protein (and therefore, of protein synthesis) could be turned off or on as desired. Blocking or reducing the activity of a protein could also include using an excision technology approach similar to that described in U.S. Pat. No. 4,743,546, incorporated herein by reference in its entirety. To use this approach, the gene encoding the protein of interest is cloned between specific genetic sequences that allow specific, controlled excision of the gene from the genome. Excision could be prompted by, for example, a shift in the cultivation temperature of the culture, as in U.S. Pat. No. 4,743,546, or by some other physical or nutritional signal. PCT Publication No. WO 02/083869, published Oct. 24, 2002, describes methods for inactivation of genes in Thraustochytriales, and is incorporated herein by reference in its entirety.

In one embodiment of the present invention, it is contemplated that a mutagenesis program could be combined with a selective screening process to obtain microorganisms of interest. The mutagenesis methods could include, but are not limited to: chemical mutagenesis, gene shuffling, switching regions of the genes encoding specific enzymatic domains, or mutagenesis restricted to specific regions of those genes, as well as other methods. For example, high throughput mutagenesis methods could be used to influence or optimize production of the desired fatty acids or other lipid products. Such methods could be combined with selective (i.e., targeted or directed) modification of the FAS by molecular biology techniques. For example, one could use selective modification techniques to modify a microorganism, for example, by introduction of a recombinant nucleic acid molecule encoding the FAS protein of the invention into any suitable host cell, including host cells comprising an endogenous FAS, and then use mutagenesis technologies to optimize fatty acid production and to create strains having improved fatty acid synthesis activity or to select for microorganisms with other improved or desired qualities. Screening methods are also useful for identifying other organisms having homologous FAS genes to the FAS of *Schizochytrium*. Homologous FAS genes identified in such organisms can be used in methods similar to those described herein.

In one embodiment of the present invention, a genetically modified microorganism or plant includes a microorganism or plant that has an enhanced ability to synthesize fatty acids in general or an enhanced ability to synthesize specific short chain fatty acids. According to the present invention, "an enhanced ability to synthesize" a product refers to any enhancement, or up-regulation, in a pathway related to the synthesis of the product such that the microorganism or plant produces an increased amount of the product compared to the wild-type microorganism or plant, cultured or grown, under the same conditions. In one embodiment of the present invention, enhancement of the ability of a microorganism or plant to synthesize short chain fatty acids is accomplished by amplification of the expression of the FAS gene. Amplification of the expression of FAS can be accomplished in any suitable host cell (e.g., a Thraustochytriales cell, a bacterial cell, a yeast cell, a plant cell), for example, by introduction of a recombinant nucleic acid molecule encoding the FAS gene, or by modifying regulatory control over a native FAS gene, in the case of Thraustochytriales.

According to the present invention, "selective modification" of an organism or nucleic acid molecule refers to a targeted, or directed, modification, where the modification to be made is predetermined and designed, for example, by knowledge of the gene structure of the FAS of the present invention. For example, selective modification of an organism can be achieved by introduction (e.g., overexpression) of a recombinant nucleic acid molecule encoding a FAS protein, or by targeted modification of an endogenous gene, such as by homologous recombination. Selective modification is distinguished from random mutagenesis techniques, where in the latter process, the mutation is randomly generated by a non-target-specific method and the desired phenotype is subsequently selected through screening of mutants for the phenotype. Selective modification techniques and classical random mutagenesis and screening techniques can be combined in the present invention to produce a variety of genetically modified organisms.

Therefore, it is an embodiment of the present invention to provide a microorganism or plant that is transformed with a recombinant nucleic acid molecule comprising a nucleic acid sequence encoding FAS of the present invention. Preferred recombinant nucleic acid molecules comprising such a nucleic acid sequence include recombinant nucleic acid molecules comprising any of the FAS nucleic acid sequences previously described herein. It is one embodiment of the present invention to provide a microorganism or plant which is transformed with a genetically modified recombinant nucleic acid molecule comprising a nucleic acid sequence encoding a mutant, or homologue, FAS. Protein homologues have been described in detail herein.

It is another embodiment of the present invention to provide a genetically modified microorganism for producing a fatty acid by a biosynthetic process, wherein the microorganism comprises a nucleic acid molecule encoding a FAS protein of the present invention and wherein the nucleic acid molecule encoding the FAS protein has been modified to increase the expression or biological activity of the FAS. The FAS can be any FAS described herein, including homologues and biologically active fragments as described herein. In one aspect of the invention, the microorganism has an endogenous FAS (e.g., a member of Thraustochytriales), and the endogenous gene is modified to increase the expression or activity of the FAS (e.g., by introducing a promoter that gives higher levels of expression than that of the native promoter, by genetically mutating the endogenous gene to increase the activity of the enzyme, etc.). In another embodiment, the microorganism is genetically modified by transformation with a recombinant nucleic acid molecule encoding a FAS of the invention. Such a microorganism can be any suitable host microorganism and in one embodiment, is a Thraustochytriales microorganism (e.g., a *Schizochytrium*), such that the microorganism comprises both an endogenous FAS and a recombinant FAS. The FAS proteins in this scenario need not be identical, since one or both of the endogenous and recombinant FAS proteins can be modified as compared to a wild-type *Schizochytrium* FAS disclosed herein to produce a FAS homologue. For example, one or both of the endogenous or recombinant FAS-encoding nucleic acid molecules can be modified to increase the expression or activity of the FAS proteins.

Accordingly, one embodiment of the invention is a biomass comprising any of the microorganisms described herein comprising a nucleic acid molecule encoding a FAS of the present invention that has been modified to increase the expression or biological activity of the FAS as described above. As used herein, a biomass refers to a population of microbial cells that have been harvested from a fermentation or culture process. Various fermentation parameters for inoculating, growing and recovering microfloral biomasses are discussed in detail in U.S. Pat. No. 5,130,242, incorporated herein by reference in its entirety. The biomass harvested from a fermentation run can be dried (e.g., spray drying, tunnel drying, vacuum drying, or a similar process) and used in any food, pharmaceutical or other desired product. Alternatively, the harvested and washed biomass can be used directly (without drying) in various products. To extend its shelf life, the wet biomass can be acidified (approximate pH=3.5-4.5) and/or pasteurized or flash heated to inactivate enzymes and then canned, bottled or packaged under a vacuum or non-oxidizing atmosphere (e.g., $N_2$ or $CO_2$).

One embodiment of the present invention is a method to produce a short chain fatty acid by a biosynthetic process, comprising culturing in a fermentation medium a genetically modified microorganism that has increased expression or biological activity of a FAS protein as described above. For example, the microorganism can have increased expression or biological activity of any FAS proteins described herein, including homologues and enzymatically active portions thereof. The FAS protein can be an endogenous FAS protein and/or a recombinant FAS protein according to the invention. The microorganism is cultured or grown in a suitable medium, under conditions effective to produce the desired fatty acid or other lipid product. An appropriate, or effective, medium refers to any medium in which a genetically modified microorganism of the present invention, when cultured, is capable of producing the desired product. Such a medium is typically an aqueous medium comprising assimilable carbon, nitrogen and phosphate sources. Such a medium can also include appropriate salts, minerals, metals and other nutrients. Microorganisms of the present invention can be cultured in conventional fermentation bioreactors. The microorganisms can be cultured by any fermentation process which includes, but is not limited to, batch, fed-batch, cell recycle, and continuous fermentation. Preferred growth conditions for potential host microorganisms according to the present invention are well known in the art. The desired products produced by the genetically modified microorganism can be recovered from the fermentation medium using conventional separation and purification techniques. For example, the fermentation medium can be filtered or centrifuged to remove microorganisms, cell debris and other particulate matter, and the product can be recovered from the cell-free supernatant by conventional methods, such as, for example, ion exchange, chromatography, extraction, solvent extraction, membrane separation, electrodialysis, reverse osmosis, distillation, chemical derivatization and crystallization. Alternatively, microorganisms producing the desired product, or extracts and various fractions thereof, can be used without removal of the microorganism components from the product, such as in a biomass of the invention.

One embodiment of the present invention is a method to produce short chain fatty acids by growing or culturing a genetically modified plant of the present invention as previously described herein. Such a method includes the step of culturing in a fermentation medium or growing in a suitable environment, such as soil, a plant having a genetic modification to increase the action of FAS. Preferably, the genetic modification includes transformation or transfection of the plant with a recombinant nucleic acid molecule that expresses a protein having FAS biological activity. Such a protein can include any of the FAS proteins described herein, including any homologue of a naturally occurring FAS having biological activity.

In the method for production of short chain fatty acids of the present invention, a plant that has a genetic modification to increase the action of FAS is cultured in a fermentation medium or grown in a suitable medium such as soil for production of the FAS. An appropriate, or effective, fermentation medium has been discussed in detail above. A suitable growth medium for higher plants includes any growth medium for plants, including, but not limited to, soil, sand, any other particulate media that support root growth (e.g. vermiculite, perlite, etc.) or Hydroponic culture, as well as suitable light, water and nutritional supplements which optimize the growth of the higher plant. The genetically modified plants of the present invention are engineered to produce significant quantities of short chain fatty acids through increased action of the FAS protein of the present invention. The short chain fatty acids can be recovered through purification processes which extract these products from the plant. In a preferred embodiment, the fatty acids are recovered by harvesting the plant or plant fraction (e.g., oils). In this embodiment, the plant or plant fraction can be consumed in its natural state or further processed into consumable products.

Another embodiment of the invention relates to a genetically modified microorganism with a reduced ability to produce short chain fatty acids (resulting in reduced amounts of short chain fatty acid production in the microorganism), wherein the microorganism has been genetically modified to selectively delete, but more preferably attenuate (inhibit, reduce the expression or activity of, etc., without actually deleting or completely inactivating the gene or its protein product) a FAS gene or portion thereof encoding a functional domain. In a preferred embodiment, the microorganism is a microalga, and in a more preferred embodiment, is a Thraustochytriales microorganism (e.g., a *Schizochytrium*). The FAS gene can be modified by modification to the coding region of the FAS gene or to a regulatory region of the FAS gene, such that expression and/or biological activity of the FAS gene is reduced, and preferably inhibited so that the microorganism has reduced production of short chain fatty acids and more preferably, increased production of long chain fatty acids, and particularly, of polyunsaturated fatty acids (PUFAs). In one embodiment the FAS gene is partially or completely deleted or inactivated, including by replacing the gene with a non-FAS nucleic acid sequence, such as by gene disruption through homologous recombination. In this aspect, the FAS gene is mutated or inactivated (or deleted) by targeted homologous recombination with a nucleic acid sequence that hybridizes to the FAS gene that includes a heterologous nucleic acid sequence that disrupts the coding region of the FAS gene.

Production of a microorganism that has reduced FAS expression or activity has commercial benefits, as described above. Microorganisms that contain the FAS of the present invention include members of Thraustochytriales, which are known to be valuable organisms for the production of lipids containing high levels of polyunsaturated fatty acids (PUFAs), including highly unsaturated fatty acids such as omega-3 fatty acids. Polyunsaturated fatty acids (PUFAs) are critical components of membrane lipids in most eukaryotes (Lauritzen et al., *Prog. Lipid Res.* 40 1 (2001); McConn et al., *Plant J.* 15, 521 (1998)) and are precursors of certain hormones and signaling molecules (Heller et al., *Drugs* 55, 487 (1998); Creelman et al., *Annu. Rev. Plant Physiol. Plant Mol. Biol.* 48, 355 (1997)). According to the present invention, a preferred PUFA is a long chain PUFA, which is defined as a PUFA having eighteen carbons or more. PUFAs include any omega-3 or omega-6 polyunsaturated fatty acids with three or more double bonds. Omega-3 PUFAs are polyethylenic fatty acids in which the ultimate ethylenic bond is three carbons from and including the terminal methyl group of the fatty acid and include, for example, docosahexaenoic acid C22:6(n-3) (DHA) and omega-3 docosapentaenoic acid C22:5(n-3) (DPAn-3). Omega-6 PUFAs are polyethylenic fatty acids in which the ultimate ethylenic bond is six carbons from and including the terminal methyl group of the fatty acid and include, for example, arachidonic acid C20:4(n-6) (ARA), C22:4(n-6), omega-6 docosapentaenoic acid C22:5(n-6) (DPAn-6) and dihomogammalinolenic acid C20:3(n-6)(dihomo GLA). Members of Thraustochytriales, such as *Schizochytrium*, accumulate large quantities of triacylglycerols rich in PUFAs. Since these lipid products are useful in a variety of food and other commercial products, it would be useful to enhance the ability of microorganisms to preferentially produce the PUFAs. The present invention provides one method by which this goal can be achieved (i.e., by attenuation of the competing FAS system).

Accordingly, another embodiment of the invention relates to a biomass comprising genetically modified microorganism (e.g., a microorganism of the order Thraustochytriales (e.g., *Schizochytrium, Thraustochytrium*)) that have reduced short chain fatty acid synthesis and more preferably, increased PUFA synthesis, as compared to a wild-type microorganism of the same species, as described above. It is to be understood that organisms other than Thraustochytriales may be discovered which contain a FAS protein having homology and most or all of the biological activities of the full length FAS described herein. Such microorganisms can also be modified to reduce the expression or activity of the FAS system, particularly if such microorganisms are also useful for producing PUFAs.

Fatty acids produced in accordance with the methods of the present invention are typically produced as lipids. As used herein, the term "lipid" includes phospholipids (PL); free fatty acids; esters of fatty acids; triacylglycerols (TAG); diacylglycerides; phosphatides; sterols and sterol esters; carotenoids; xanthophylls (e.g., oxycarotenoids); hydrocarbons; and other lipids known to one of ordinary skill in the art. The term "fatty acid" (including as the term is used in "polyunsaturated fatty acid" and "PUFA") includes not only the free fatty acid form, but other forms as well, such as the triacyglycerol (TAG) form and the phospholipids (PL) form.

A food product, as used herein, includes any food ingredient (e.g., a food product that is part of another food product, such as an oil), and also includes, but is not limited to: fine bakery wares, bread and rolls, breakfast cereals, processed and unprocessed cheese, condiments (ketchup, mayonnaise, etc.), dairy products (milk, yogurt), puddings and gelatine desserts, carbonated drinks, teas, powdered beverage mixes, processed fish products, fruit-based drinks, chewing gum, hard confectionery, frozen dairy products, processed meat products, nut and nut-based spreads, pasta, processed poultry products, gravies and sauces, potato chips and other chips or crisps, chocolate and other confectionery, soups and soup mixes, soya based products (milks, drinks, creams, whiteners), vegetable oil-based spreads, and vegetable-based drinks. Other products include dietary supplements, a pharmaceutical formulation (e.g., a pharmaceutical product), humanized animal milk, and infant formulas. Suitable pharmaceutical formulations or products include, but are not limited to, an anti-inflammatory formulation, a chemotherapeutic agent, an active excipient, an osteoporosis drug, an anti-depressant, an anti-convulsant, an anti-*Heliobactor pylori* drug, a drug for treatment of neurodegenerative disease, a drug for treatment of degenerative liver disease, an antibiotic, a cholesterol lowering formulation, and products used to treat a condition selected from the group consisting of: chronic inflammation, acute inflammation, gastrointestinal disorder, cancer, cachexia, cardiac restenosis, neurodegenerative disorder, degenerative disorder of the liver, blood lipid disorder, osteoporosis, osteoarthritis, autoimmune disease, preeclampsia, preterm birth, age related maculopathy, pulmonary disorder, and peroxisomal disorder.

Therefore, another embodiment of the present invention relates to a method for producing lipids, and preferably PUFAs, from a biosynthetic process, comprising culturing under conditions effective to produce the lipids genetically modified microorganisms (e.g., of the order Thraustochytriales) as previously described herein, wherein the microorganisms have been genetically modified to selectively increase or decrease (depending on the goal) a FAS gene as described above. The lipids can be recovered using any one of a variety of recovery techniques known in the art or the entire microorganism or extracts thereof can be recovered. One aspect of the invention relates to a method for recovering lipids from a biosynthetic process, comprising recovering lipids from a culture of genetically modified microorganisms (e.g., of the order Thraustochytriales), wherein the microorganisms have been genetically modified to selectively increase or decrease a FAS gene as described above. Techniques for recovery of lipids from the culture are known in the art and include, but are not limited to, ion exchange, chromatography, extraction, solvent extraction, phase separation, membrane separation, electrodialysis, reverse osmosis, distillation, chemical derivatization and crystallization.

Another embodiment of the present invention is a method for producing short chain fatty acids using an isolated FAS, including a homologue of a FAS as described herein. The method can be operated in batch or continuous mode using a stirred tank, a plug-flow column reactor or other apparatus known to those skilled in the art.

In one embodiment, the FAS is bound to a solid support, i.e., an immobilized enzyme. As used herein, a FAS bound to a solid support (i.e., an immobilized FAS) includes immobilized isolated FAS, immobilized cells which contain a FAS (including immobilized and genetically modified Thraustochytriales, bacterial, fungal (e.g., yeast), microalgal, or plant cells), stabilized intact cells and stabilized cell/membrane homogenates. Stabilized intact cells and stabilized cell/membrane homogenates include cells and homogenates from naturally occurring microorganisms expressing FAS or from genetically modified microorganisms or plants as disclosed elsewhere herein. Thus, although methods for immobilizing FAS are discussed below, it will be appreciated that such methods are equally applicable to immobilizing cells and in such an embodiment, the cells can be lysed.

A variety of methods for immobilizing an enzyme are disclosed in Industrial Enzymology 2nd Ed., Godfrey, T. and West, S. Eds., Stockton Press, New York, N.Y., 1996, pp. 267-272; Immobilized Enzymes, Chibata, I. Ed., Halsted Press, New York, N.Y., 1978; Enzymes and Immobilized Cells in Biotechnology, Laskin, A. Ed., Benjamin/Cummings Publishing Co., Inc., Menlo Park, California, 1985; and Applied Biochemistry and Bioengineering, Vol. 4, Chibata, I. and Wingard, Jr., L. Eds, Academic Press, New York, N.Y., 1983, which are incorporated herein in their entirety.

Briefly, a solid support refers to any solid organic supports, artificial membranes, biopolymer supports, or inorganic supports that can form a bond with FAS (or cell) without significantly affecting the activity of isolated FAS. Exemplary organic solid supports include polymers such as polystyrene, nylon, phenol-formaldehyde resins, acrylic copolymers (e.g., polyacrylamide), stabilized intact whole cells, and stabilized crude whole cell/membrane homogenates. Exemplary biopolymer supports include cellulose, polydextrans (e.g., Sephadex®), agarose, collagen and chitin. Exemplary inorganic supports include glass beads (porous and nonporous), stainless steel, metal oxides (e.g., porous ceramics such as $ZrO_2$, $TiO_2$, $Al_2O_3$, and NiO) and sand. Preferably, the solid support is selected from the group consisting of stabilized intact cells and/or crude cell homogenates. Preparation of such supports requires a minimum of handling and cost. Additionally, such supports provide excellent stability of the enzyme.

Stabilized intact cells and/or cell/membrane homogenates can be produced, for example, by using bifunctional crosslinkers (e.g., glutaraldehyde) to stabilize cells and cell homogenates. In both the intact cells and the cell membranes, the cell wall and membranes act as immobilizing supports. In such a system, integral membrane proteins are in the "best" lipid membrane environment. Whether starting with intact cells or homogenates, in this system the cells are either no longer "alive" or "metabolizing", or alternatively, are "resting" (i.e., the cells maintain metabolic potential and active FAS, but under the culture conditions are not growing); in either case, the immobilized cells or membranes serve as biocatalysts.

FAS can be bound to a solid support by a variety of methods including adsorption, cross-linking (including covalent bonding), and entrapment. Adsorption can be through van der Waal's forces, hydrogen bonding, ionic bonding, or hydrophobic binding. Exemplary solid supports for adsorption immobilization include polymeric adsorbents and ion-exchange resins. Solid supports in a bead form are particularly well-suited. The particle size of an adsorption solid support can be selected such that the immobilized enzyme is retained in the reactor by a mesh filter while the substrate (e.g., the precursor or substrate used as a starting material to produce the desired fatty acid) is allowed to flow through the reactor at a desired rate. With porous particulate supports it is possible to control the adsorption process to allow FAS or genetically modified microorganism cells to be embedded within the cavity of the particle, thus providing protection without an unacceptable loss of activity.

Cross-linking of a FAS to a solid support involves forming a chemical bond between a solid support and a FAS. It will be appreciated that although cross-linking generally involves linking a FAS to a solid support using an intermediary compound, it is also possible to achieve a covalent bonding between the enzyme and the solid support directly without the use of an intermediary compound. Cross-linking commonly uses a bifunctional or multifunctional reagent to activate and attach a carboxyl group, amino group, sulfur group, hydroxy group or other functional group of the enzyme to the solid support. The term "activate" refers to a chemical transformation of a functional group which allows a formation of a bond at the functional group. Exemplary amino group activating reagents include water-soluble carbodiimides, glutaraldehyde, cyanogen bromide, N-hydroxysuccinimide esters, triazines, cyanuric chloride, and carbonyl diimidazole. Exemplary carboxyl group activating reagents include water-soluble carbodiimides, and N-ethyl-5-phenylisoxazolium-3-sulfonate. Exemplary tyrosyl group activating reagents include diazonium compounds. And exemplary sulfhydryl group activating reagents include dithiobis-5,5'-(2-nitrobenzoic acid), and glutathione-2-pyridyl disulfide. Systems for covalently linking an enzyme directly to a solid support include Eupergit®, a polymethacrylate bead support available from Rohm Pharma (Darmstadt, Germany), kieselguhl (Macrosorbs), available from Sterling Organics, kaolinite available from English China Clay as "Biofix" supports, silica gels which can be activated by silanization, available from W. R. Grace, and high-density alumina, available from UOP (Des Plaines, Ill.).

Entrapment can also be used to immobilize FAS. Entrapment of FAS involves formation of, inter alia, gels (using organic or biological polymers), vesicles (including microencapsulation), semipermeable membranes or other matrices. Exemplary materials used for entrapment of an enzyme include collagen, gelatin, agar, cellulose triacetate, alginate, polyacrylamide, polystyrene, polyurethane, epoxy resins, carrageenan, and egg albumin. Some of the polymers, in particular cellulose triacetate, can be used to entrap the enzyme as they are spun into a fiber. Other materials such as polyacrylamide gels can be polymerized in solution to entrap the enzyme. Still other materials such as polyglycol oligomers that are functionalized with polymerizable vinyl end groups can entrap enzymes by forming a cross-linked polymer with UV light illumination in the presence of a photosensitizer.

The present invention also includes isolated (i.e., removed from their natural milieu) antibodies, or antigen binding fragments thereof, that are capable of selectively binding to a FAS protein of the present invention (e.g., FAS antibodies). The phrase "selectively binds" refers to the specific binding of one protein to another (e.g., an antibody, fragment thereof, or binding partner to an antigen), wherein the level of binding, as measured by any standard assay (e.g., an immunoassay), is statistically significantly higher than the background control for the assay. For example, when performing an immunoassay, controls typically include a reaction well/tube that contain antibody or antigen binding fragment alone (i.e., in the absence of antigen), wherein an amount of reactivity (e.g., non-specific binding to the well) by the antibody or antigen binding fragment thereof in the absence of the antigen is considered to be background. Binding can be measured using a variety of methods standard in the art including enzyme immunoassays (e.g., ELISA), immunoblot assays, etc.). Antibodies of the present invention can be polyclonal or monoclonal, functional equivalents such as antibody fragments and genetically-engineered antibodies, including single chain antibodies or chimeric antibodies, including bi-specific antibodies that can bind to more than one epitope.

Generally, in the production of an antibody, a suitable experimental animal, such as, for example, but not limited to, a rabbit, a sheep, a hamster, a guinea pig, a mouse, a rat, or a chicken, is exposed to an antigen against which an antibody is desired. Typically, an animal is immunized with an effective amount of antigen that is injected into the animal. An effective amount of antigen refers to an amount needed to induce antibody production by the animal. The animal's immune system is then allowed to respond over a pre-determined period of time. The immunization process can be repeated until the immune system is found to be producing antibodies to the antigen. In order to obtain polyclonal antibodies specific for the antigen, serum is collected from the animal that contains the desired antibodies (or in the case of a chicken, antibody can be collected from the eggs). Such serum is useful as a reagent. Polyclonal antibodies can be further purified from the serum (or eggs) by, for example, treating the serum with ammonium sulfate.

Monoclonal antibodies may be produced according to the methodology of Kohler and Milstein (*Nature* 256:495-497, 1975). For example, B lymphocytes are recovered from the spleen (or any suitable tissue) of an immunized animal and then fused with myeloma cells to obtain a population of hybridoma cells capable of continual growth in suitable culture medium. Hybridomas producing the desired antibody are selected by testing the ability of the antibody produced by the hybridoma to bind to the desired antigen.

Genetically engineered antibodies of the invention include those produced by standard recombinant DNA techniques involving the manipulation and re-expression of DNA encoding antibody variable and/or constant regions. Particular examples include, chimeric antibodies, where the $V_H$ and/or $V_L$ domains of the antibody come from a different source to the remainder of the antibody, and CDR grafted antibodies (and antigen binding fragments thereof), in which at least one CDR sequence and optionally at least one variable region framework amino acid is (are) derived from one source and the remaining portions of the variable and the constant regions (as appropriate) are derived from a different source. Construction of chimeric and CDR-grafted antibodies are described, for example, in European Patent Applications: EP-A 0194276, EP-A 0239400, EP-A 0451216 and EP-A 0460617.

The following examples are provided for the purpose of illustration and are not intended to limit the scope of the present invention.

EXAMPLES

Example 1

The following example describes the cloning and characterization of the *Schizochytrium* FAS proteins of the invention.

Briefly, a cDNA library was prepared from mRNA isolated from *Schizochytrium* cells as described in Metz et al., Science 293, pp 290-292 (2001). Approximately 8,500 clones were randomly chosen and sequenced from the 5' end using a vector-derived primer. A search of this database using various FAS proteins as queries revealed the presence of many homologues. When the database was queried using the yeast FAS subunits (a and b), over 40 sequences were found with significant homology. Most of these *Schizochytrium* sequences could be assembled into a single large (~4000 bp) contig. When individual cDNA sequences were used as queries in a BLAST search (tblastn) the best matches were, in most cases, to the FAS subunits of fungal organisms. In these organisms the Type I FAS is composed of two subunits (a and b), each carrying a distinct set of enzymatic domains. One anomaly of the cDNA sequence data was that all but one of the matches were to the "a" subunit. Using the sequence tags as a guide, the inventors cloned the corresponding regions of genomic DNA encoding those cDNA-derived sequences. As the project proceeded, the reason for the anomalous representation of the subunits in the cDNA library became clear. The FAS in *Schizochytrium* is encoded by a single large gene. The FAS Orf contains 12,408 bp and encodes a protein with a deduced molecular mass of 444,884 Daltons. No evidence for introns could be found, either by analysis of the genomic sequence itself or by comparison to available cDNA sequences. Blast and Pfam results plus motif analyses were used to establish a preliminary structure and functional identification of the domains of this Type I protein. Both in terms of amino acid sequence and in the sequential organization, the *Schizochytrium* FAS resembles a fusion of the head (N-terminus) of the fungal FAS a subunit to the tail (C-terminus) of the b subunit.

The DNA fragments containing the *Schizochytrium* FAS open reading frame were cloned from a lambda library of genomic DNA. Standard methods were used to produce that library as well as PCR derived probes (based on sequences obtained from cDNA clones) for isolation of the respective DNA fragments. The Orf encoding the FAS gene was sequenced using a combination of subcloning and primer walking.

The complete *Schizochytrium* FAS-encoding sequence is a 12,408 nucleotide sequence (not including the stop codon), represented herein by SEQ ID NO:1, which encodes a 4136 amino acid sequence, represented herein as SEQ ID NO:2. Within the *Schizochytrium* FAS protein are nine domains as described above: (a) one acetyl-transferase (AT) domain (SEQ ID NO:5); (b) one enoyl ACP reductase (ER) domain (SEQ ID NO:6); (c) one dehydrase (DH) domain (SEQ ID NO:7); (d) one malonyl/palmitoyl acyltransferase (M/PAT) domain (SEQ ID NO:8); (e) two acyl carrier protein (ACP) domains (SEQ ID NO:9 and (SEQ ID NO:10); (f) one ketoacyl ACP reductase (KR) domain (SEQ ID NO:11); (g) one keto-acyl ACP synthase (KS) domain (SEQ ID NO:12); and (h) one phosphopantetheinyl transferase (PPT) domain (SEQ ID NO:13).

FIG. 1 is a schematic representation of the putative enzymatic domains present in the *Schizochytrium* FAS protein based on the identification, cloning and sequencing of this protein by the present inventors, followed by analysis of the sequences. The size and positions of the putative domains relative to the entire protein, and the identification of the functions of those domains, are based on Pfam analyses results and on homology to the well-characterized FAS (α and β subunits) of baker's yeast (*Saccharomyces cerevisiae*) (references 1, 2 & 3). The domain organization and sizes relative to the overall protein sizes of the yeast FAS (α and β subunits) are shown for comparison.

Abbreviations: (AT) acetyl-transferase; (ER) enoyl ACP reductase; (DH) dehydrase (DH); (M/PAT) malonyl/palmitoyl acyltransferase; (ACP #1) the first acyl carrier protein; (ACP #2) the second acyl carrier protein; (R) keto-acyl ACP reductase; (KS) keto-acyl ACP synthase; and (PPT) phosphopantetheinyl transferase.

REFERENCES

1. Mohamed et al., *J Biol Chem*. 1988 Sep. 5; 263(25): 12315-25.
2. Chirala et al., *J Biol Chem*. 1987 Mar. 25; 262(9):4231-40.
3. Fichtlscherer et al., *Eur J Biochem*. May 2000; 267(9): 2666-71.

Example 2

The following example describes the targeted inactivation of the *Schizochytrium* FAS gene.

The *Schizochytrium* FAS gene was inactivated by targeted inactivation, using technology that is described in PCT Publication No. WO 02/083869, published Oct. 24, 2002. PCT Publication No. WO 02/083869 is incorporated herein by reference in its entirety.

Figure 2A:
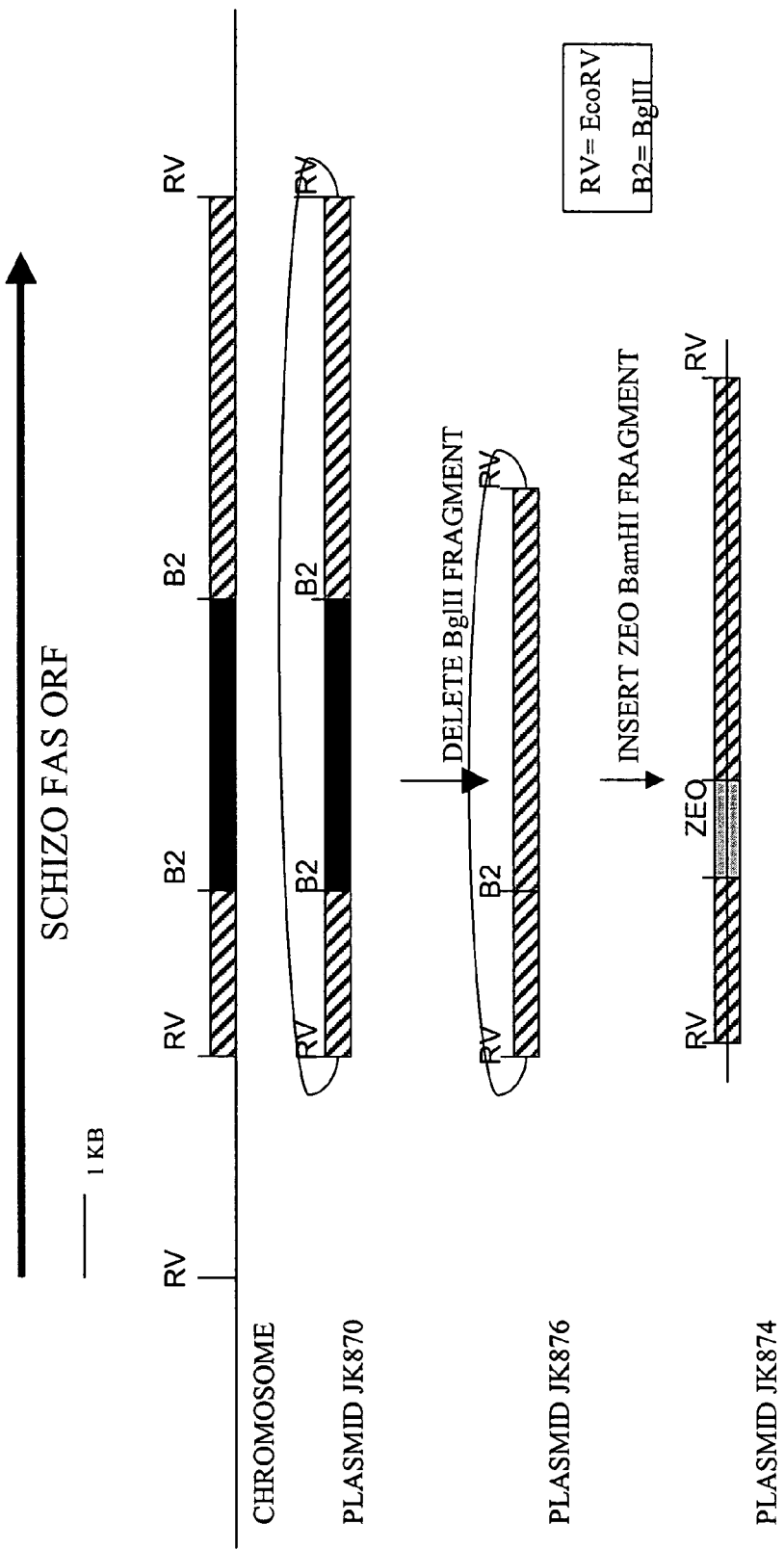
FIG. 2A is a schematic representation of the construction of a plasmid used for targeted inactivation of the *Schizochytrium* FAS gene.

FIG. 2A diagrams the construction of a plasmid used for targeted inactivation of the *Schizochytrium* FAS gene. The straight line represents the region of the *Schizochytrium* chromosome containing the FAS gene. The arrow above the line indicates the position of the open reading frame (Orf) that encodes the FAS protein. The boxed area on the line (both striped and solid) represents the portion of the chromosome cloned into the plasmid; JK870. Digestion of JK870 with the restriction enzyme BglII, followed by dilution and ligation, resulted in recovery of plasmid JK876, in which the BglII fragment (solid box) has been deleted. A fragment of DNA containing the ble gene (encoding a protein that confers resistance to Zeocin™) along with the α-tubulin promoter region and a SV40 terminator region (see below), isolated from the plasmid pTUBZEO11-2, by digestion with BamHI, is then cloned into the BglII site of JK876 to generate the plasmid JK874.

FIG. 2B diagrams the events that are believed to occur and result in the stable inactivation of the FAS gene in *Schizochytrium*. The plasmid JK874 is introduced into whole cells of *Schizochytrium* (either the 20888 strain, or the cell wall deficient strain—AC66) via particle bombardment (as described in PCT Publication No. WO 02/083869, ibid.). The initial selection for transformed cells (i.e., having the Zeocin™ resistance gene from plasmid JK874 introduced into the chromosome in a functional manner) was made on agar plates with growth medium containing Zeocin™ and supplemented with free saturated fatty acids (i.e., C16:0) solubilized with β-cyclodextrin. Colonies that grow under these selective conditions were transferred to a new plate in a grid-like array. The transformants were then tested for their ability to grow without fatty acid supplementation by transferring cells from the colonies to a plate containing Zeocin™ but lacking the fatty acid. The colonies that are Zeocin™ resistant and require supplementation with 16:0 fatty acids for growth were presumed to have had the FAS gene inactivated via a homologous recombination event. Those colonies that did not show reversion to 16:0 prototrophy were presumed to have integrated the Zeocin™ resistance gene cassette into the FAS region via a double crossover event as diagramed. The stability of the phenotype (requirement for supplementation with 16:0 fatty acid for growth) indicates a portion of the FAS Orf has been replaced with the DNA conferring Zeocin™ resistance. The integration into the FAS portion of the chromosome was then confirmed via a PCR reaction as diagramed. In this manner, FAS knock-outs in both *Schizochytrium* strains ATCC 20888 and AC66 were obtained.

Example 3

The following example describes in vitro fatty acid synthesis assays in strains in which the *Schizochytrium* FAS system of the invention has been inactivated.

Figure 3:
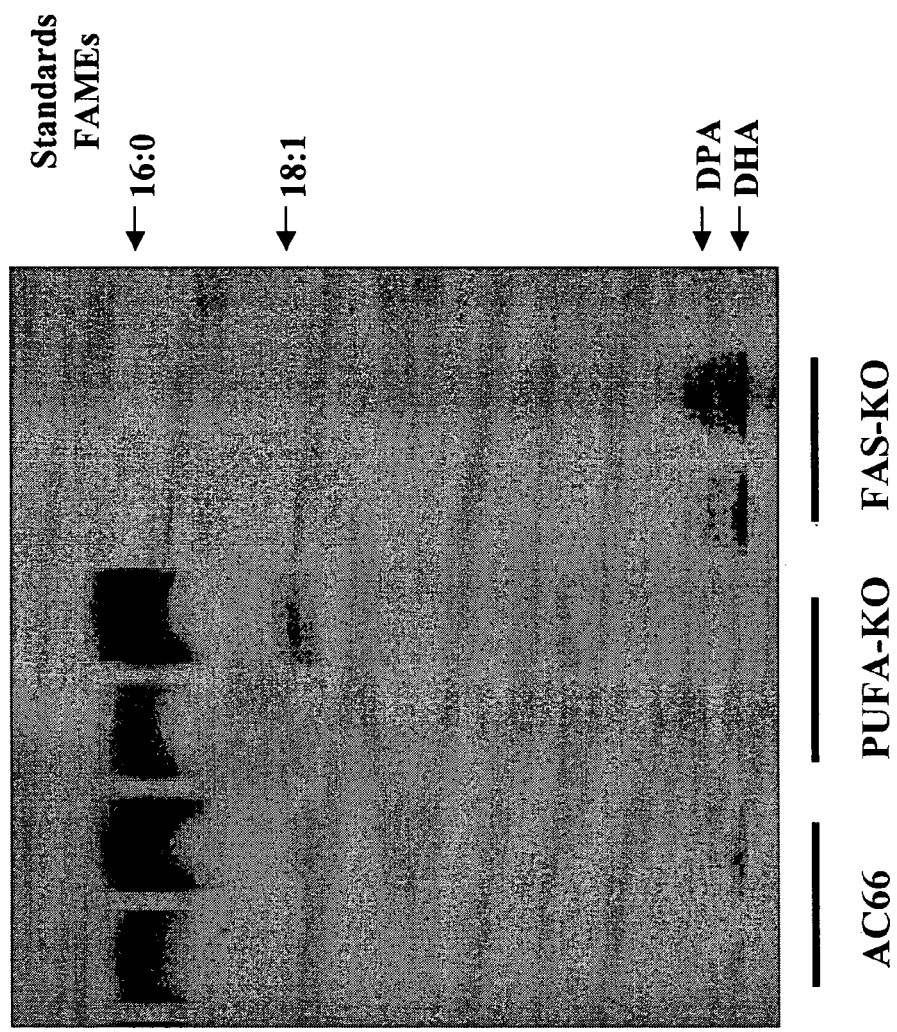
FIG. 3 is a digitized image of the synthesis of fatty acids from [1-$^{14}$C]-malonyl-CoA in cell free homogenates from a cell wall deficient strain of *Schizochytrium* (AC66) and mutants of that strain in which either the PUFA polyketide synthase orfC gene (PUFA-KO) or the FAS gene (FAS-KO) have been inactivated.

FIG. 3 shows the synthesis of fatty acids from [1-$^{14}$C]-malonyl-CoA in cell free homogenates from a cell wall deficient strain of *Schizochytrium* (AC66) and mutants of that strain in which either the PUFA polyketide synthase orfC gene (PUFA-KO) or the FAS gene (FAS-KO) (see FIGS. 2A and 2B above) have been inactivated. Cells were disrupted by sonication in 100 mM phosphate buffer, pH 7.2 containing 2 mM DTT, 1 mM EDTA and 10% glycerol. Aliquots of the homogenates were supplemented with 10 μM acetyl-CoA, 100 μM [1-$^{14}$C]-malonyl-CoA, 2 mM NADH and 2 mM NADPH and incubated for 30 min at 30° C. Fatty acids in the reaction mixture were converted to methyl esters, extracted into hexane and separated by AgNO$_3$ thin layer chromatography (TLC) (solvent: hexane/diethyl ether/HOAc 70/30/2 by vol). Radioactivity on the TLC plates was detected using a Molecular Dynamics phosphorimaging system. Migration distances of fatty acid methyl ester standards (16:0, 18:1, DPA n-6, and DHA) are indicated to the right side of the diagram.

Assays of the homogenate of the AC66 parent strain reveal the presence of radiolabeled bands that co-migrate with the 16:0-, 18:1- and DHA-methyl ester standards. In the PUFA-KO mutant strain, the radiolabeled band that co-migrates with the DHA methyl ester standard is greatly reduced (or lacking). In the FAS-KO strain, radiolabeled bands that co-migrate with the 16:0- and 18:1-methyl ester standards (as well as another band) are greatly reduced (or lacking). These data indicate that inactivation of the FAS gene results in the loss of the ability to synthesize short chain saturated fatty acids and suggest that 18:1 is derived from products of the FAS. The data also show that synthesis of DHA and DPA in *Schizochytrium* is not dependent on products of the FAS system.

Each publication cited herein is incorporated herein by reference in its entirety.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. A genetically modified Thraustochytriales microorganism with reduced production of short chain fatty acids, wherein the microorganism's fatty acid synthase gene or portion thereof encoding a functional domain has been genetically modified, to selectively attenuate a fatty acid synthase gene wherein the fatty acid synthase gene comprises a nucleic acid sequence selected from the group consisting of:
   a) a nucleic acid sequence encoding SEQ ID NO:2; and
   b) a nucleic acid sequence encoding an amino acid sequence that is at least 85% identical to SEQ ID NO:2, wherein the protein having the amino acid sequence has a biological activity selected from the group consisting of acetyl-transferase (AT) activity; enoyl ACP reductase (ER) activity; dehydrase (DH) activity; malonyl/palmitoyl acyltransferase (M/PAT) activity; a first acyl carrier protein (ACP) activity; a second acyl carrier protein (ACP) activity; keto-acyl ACP reductase (KR) activity; keto-acyl ACP synthase (KS) activity; and phosphopantetheinyl transferase (PPT) activity.

2. The genetically modified microorganism of claim 1, wherein the fatty acid synthase is encoded from a nucleic acid sequence represented by SEQ ID NO: 1.

3. The genetically modified microorganism of claim 1, wherein the microorganism has increased production of at least one polyunsaturated fatty acid (PUFA).

4. The genetically modified microorganism of claim 1, wherein the fatty acid synthase gene has been modified in a regulatory region to reduce expression of the gene.

5. The genetically modified microorganism of claim 1, wherein the fatty acid synthase gene has been modified in the coding region to reduce the biological activity of one or more functional domains of the fatty acid synthase.

6. The genetically modified microorganism of claim 1, wherein the fatty acid synthase gene has been mutated by targeted homologous recombination with a nucleic acid sequence that hybridizes to the fatty acid synthase gene and includes a heterologous nucleic acid sequence that modifies the coding region of the fatty acid synthase gene to reduce the expression or activity of the fatty acid synthase encoded thereby.

7. A biomass comprising genetically modified microorganisms as set forth in claim 1, wherein the microorganisms have reduced production of short chain fatty acids as compared to a wild-type microorganism of the same species.

8. A food product or a pharmaceutical product comprising the biomass according to claim 7.

9. A method for increasing the production of polyunsaturated fatty acids (PUFAs) in a biosynthetic process, comprising culturing under conditions effective to produce lipids comprising the PUFAs, the genetically modified microorganisms according to claim 1.

10. A genetically modified Thraustochytriales microorganism with reduced production of short chain fatty acids, wherein the microorganism's fatty acid synthase gene or portion thereof encoding a functional domain has been genetically modified, to selectively attenuate a fatty acid synthase gene wherein the fatty acid synthase gene comprises a nucleic acid sequence encoding SEQ ID NO: 2.

* * * * *